US008735371B2

(12) United States Patent
Carthew et al.

(10) Patent No.: US 8,735,371 B2
(45) Date of Patent: May 27, 2014

(54) COMPOSITIONS AND METHODS FOR ALTERING RNAI

(71) Applicant: Northwestern University, Evanston, IL (US)

(72) Inventors: Richard William Carthew, Evanstion, IL (US); Young Sik Lee, Seoul (KR); Dinari Harris, Wheaton, MD (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/668,441

(22) Filed: Nov. 5, 2012

(65) Prior Publication Data

US 2013/0131145 A1 May 23, 2013

Related U.S. Application Data

(63) Continuation of application No. 11/641,937, filed on Dec. 19, 2006, now Pat. No. 8,318,688.

(60) Provisional application No. 60/751,596, filed on Dec. 19, 2005.

(51) Int. Cl.
*A61K 48/00* (2006.01)
*C07H 21/02* (2006.01)
*C07H 21/04* (2006.01)

(52) U.S. Cl.
USPC ............................ 514/44; 536/23.1; 536/24.5

(58) Field of Classification Search
CPC ............... C12N 15/111; C12N 15/113; C12N 2310/14; C12N 2310/141
See application file for complete search history.

(56) References Cited

U.S. PATENT DOCUMENTS

| | | | |
|---|---|---|---|
| 6,348,311 | B1 | 2/2002 | Kastan et al. |
| 2003/0157577 | A1 | 8/2003 | Fukushima |
| 2004/0002492 | A1 | 1/2004 | Murray Smith et al. |
| 2004/0014701 | A1 | 1/2004 | O'Connor et al. |
| 2005/0054657 | A1 | 3/2005 | Smith et al. |
| 2005/0148020 | A1 | 7/2005 | Kastan et al. |
| 2005/0260652 | A1 | 11/2005 | Ruvkun et al. |
| 2007/0077553 | A1 | 4/2007 | Bentwich |

FOREIGN PATENT DOCUMENTS

WO 2005054494 6/2005

OTHER PUBLICATIONS

Andersson M.G. et al., "Suppression of RNA interference by adenovirus virus associated RNA." Journal of Virology, 2005, vol. 79(15):9556-9565.

Carthew, "Gene silencing by double-stranded RNA," Curr Opin Cell Biol, 2001, 13:244-248.
Carthew, "Gene regulation by microRNAs," Current Opinion in Genetics & Development, 2006, 16:203-208.
Chen and Carbone, "p53 as a target for anti-cancer immunotherapy," Mol Med Today, 1997, 3:160-167.
Chiang et al., "The Hermansky-Pudlak Syndrome 1 (HPS1) and HPS4 Proteins Are Components of Two Complexes, BLOC-3, and BLOC-4, Involved in the Biogenesis of Lysosome-related Organelles," J Biol Chem, 2003, 278:20332-20337.
Duxbury et al., "RNA interference: A mammalian SID-1 homologue enhances siRNA uptake and gene silencing efficacy in human cells," Biochemical and Biophysical Research Communications, 2005, 331:459-463.
Elbashir et al., "Functional anatomy of siRNAs for mediating efficient RNAi in *Drosphila melanogaster* embryo lysate," The EMBO Journal, 2001, 20(23):6877-6888.
Feng et al., "Mouse pale ear (ep) is homologous to human Hermansky-Pudlak syndrome and contains a rare 'AT-AC' intron," Human Molecular Genetics, 1997, 6(5):793-797.
Goit et al., "A Protein Interaction Map of *Drosophila melanogaster*,"Science, 2003, 302-1727-1736.
Grishok et al., "Genes and Mechanisms Related to RNA Interference Regulate Expression of the Small Temporal RNAs that Control *C. elegans* Developmental Timing," Cell, 2001, 106:23-34.
Hannon, "RNA interference," Nature, 2002, 418:244-251.
Hanson et al., "Role of adenosine 3',5'-cyclic monophosphate (cAMP) in enhancing the efficacy of siRNA-mediated gene silencing in neuroblastoma cells," Oncogene, 2005, 24:4149-4154.
Huizing et al., "Hermanski-Pudlak Syndrome and Related Disorders of Organelle Formation," Traffic, 2000, 1:823-835.
Hutvagner et al., "A microRNA in a Multiple-Turnover RNAi Enzyme Complex," Science, 2002, 297:2056-2060.
Kataoka et al., "Developmental roles and molecular characterization of a *Drosophila* homologue of *Arabidopsis argonautel*, the founder of a novel gene superfamily," Genes to Cells, 2001, 6:313-325.
Kennedy et al., "A conserved siRNA-degrading RNase negatively regulates RNA interference in *C. elegans*," Nature, 2004, 427:645-649.
Lau et al., "Suppression of HIV-1 infection by a small molecule inhibitor of the ATM kinase," Nature Cell Biology, 2005, 7(5):493-500.
Lee et al., "Silencing by small RNAs is linked to endosomal trafficking," Nature Cell Biology, 2009, 11:1150-1156.

(Continued)

*Primary Examiner* — Amy Bowman
(74) *Attorney, Agent, or Firm* — Casimir Jones, S.C.

(57) ABSTRACT

The present invention relates to compositions and methods for altering (e.g., enhancing) RNAi. In particular, the present invention provides systems and methods for identifying regulators of RNAi. For example, the present invention provides RNAi regulators (e.g., HPS1 and HPS4) and methods of altering (e.g., inhibiting) these regulators in order to alter (e.g., enhance) RNAi. The present invention also provides methods of identifying inhibitors (e.g., small molecule, nucleic acid (e.g., siRNA), and antibody) of RNAi regulators and methods of using the same (e.g., to enhance RNAi). Compositions and methods of the present invention find use in research (e.g., functional genomics), therapeutic (e.g., drug discovery and delivery) and clinical applications.

7 Claims, 31 Drawing Sheets

(56) References Cited

OTHER PUBLICATIONS

Lu et al., "Adenovirus V AI noncoding RNA can inhibit small interfering RNA and MicroRNA biogenesis." Journal of Virology, 2004, 78(23):12868-12876.

Martina et al., "BLOC-3, a Protein Complex Containing the Hermansky-Pudlak Syndrome Gene Products HPS1 and HPS4," J Biol Chem, 2003, 278(31):29376-29384.

Nahreini et al., "Altering Cellular Signaling Pathways Enhance Gene Silencing Activity of shRNA, shRNA.Ribozyme, and shRNA.Antisense in Neuroblastoma Cells," Cellular and Molecular Neurobiology, 2004, 24:781-792.

Nakahara and Carthew, "Expanding roles for miRNAs and siRNAs in cell regulation," Curr Opin Cell Biol, 2004, 16:127-133.

Nazarian et al., "Biogenesis of lysomsome-related organelles complex 3 (BLOC-3): A complex containing the Hermansky-Pudlak syndrome (HPS) proteins HPS1 ad HPS4," PNAS, 2003, 100:8770-8775.

Novina and Sharp, "The RNAi revolution," Nature, 2004, 430:161-164.

Oh et al., "Positional cloning of a gene for Hermansky-Pudlak syndrome, a disorder of cytoplasmic organelles," Nat Genetics, 1996, 14:300-306.

Pellino et al., "ATP modulates siRNA interactions with endognous human Dicer complex," RNA, 2005, 11:1719-1724.

Pham et al., "A Dicer-2-Dependent 80S Complex Cleaves Targeted mRNAs during RNAi in *Drosophila*," Cell, 2004, 117:83-94.

Simmer et al., "Loss of the Putative RNA-Directed RNA Polymerase RRF-3 Makes *C. elegans* Hypersensitive to RNAi," Curr Biol, 2002, 12:1317-1319.

Sontheimer and Carthew, "Silence from within: Endogenous siRNAs and miRNAs," Cell, 2005, 122:9-12.

Sullivan and Ganem, "A Virus-Encoded Inhibitor That Blocks RNA Interference in Mammalian Cells," J Virol, 2005, 79(12):7371-7379.

Suzuki et al., "Hermansky-Pudlak syndrome is caused by mutations in HPS4, the human homolog of the mouse light-ear gene," Nature Genetics, 2002, 30:321-324.

FIG. 6
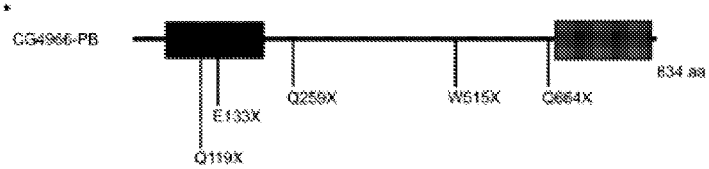
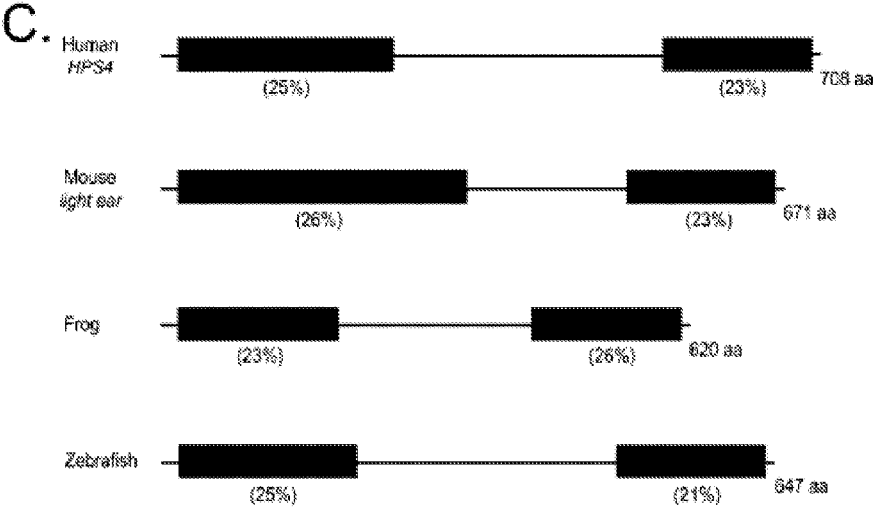

FIG. 14
SEQ ID NO.:1
Drosophila HPS4 cDNA sequences isoform RB

```
ACTAAGGTATGGCAGCGCCGTAAGTTCCTCTGCAAAGAAAAATAAAAACTAATGAATAAAATGAAGCAGAAATAAAGT
GCAATAATCTTCCGACAACGAGAGGTTACAAGTGCAATACACAATGGCTGCAAAGGAGACGATGATTGTGTTTGTCTA
CGACACAGAGTGTCTCACAGACGAGGCGGATGATCCCATATCGGCGGTGCTCTACTTCCATCCAAGCTGGGTGTCCGA
CTCCCAGAAGGTGGCTCTGTGTGGTCAGCTTATGGGCACGTCGTATTTCCTCAAGGATTGCTTCTTTAATCCCCGCAT
CCTGGCGCTGCAGAATGGAAAATTTGTGCTGAAGGAATTCGGTCGTTTTATTCTGGCAATTGGCACTGATCGAAATAT
TGGAGATCAACTGTTGGAACATCGTGCTGATCTGCTGAGTTCCCTGCTCAAGTTTTTCCACCGTGACGTCCAGACATT
GTATGCCCAGTATGCTGCACCGCCCGCCCTGAACCGCCGGAATCTCAGCGAGAAACTGTACCACATCTTTGAAACATA
TCTGCCGATGCTGCAGCGCAACGGAAATACATTTCAAAATGTGCCGAGGCTGCGAATGCCAAAGACGGCCAGTCATAT
ATTCCTGGAGGCTATACAAACGTTGCAAAGTTGCCAGCAGACAAAGGGAATACTTGGCGGAGCGATTCTGTACCACAA
CAAGGTGGTTGCCTCGCAACTGAGCGATATGGTGACCAAGCATCTTGTACTCACCGATCCTCTGCACATCCGCACTGC
GGCCGAGCAAGTGACCAACCATCCTGAGTTCCACATACCCAACGGCGTTCAGATGCTGGTGGTTTATTTGGAGCATAT
GCAGTACCGCCAGTTAGCTGGCGAGGCACAGCGCGCCCAGAACCTGCAGATGAACACAGCTCAGCTCACCCAAAATGG
TATGCCGTTTCAGTATGCCAAGCGTAAGATAAAGCGGGACAAGTCGCTCATTTTTACCCATATACCCGAGGAGGAGCA
CGCCCCGGAGCAGCAGGGAGCAGTTGAACAGCTACCACCAGCCAGGCCCAAATCTATGCGACCCACCCACCTGCCGTT
GCGTATAAAAAGCATGCAGAGCAAAGAGCTACCGGAGTCTGGCATTGCATCAATAAATTTCGACGAAACCGATTCCTA
TCCGCAGTTCATTGGACGAACCAGCGTTTGCAATACTCCAATGACCGAGAACAAGGTACTGCCGGTGGCCAATGTTAT
GTCCATTTGCGCAAATCCCGAAGATGAGGGCAAAGAGGAGGATATTCACAATTCCAATGGCAAGACACATTCGCGTCG
AAATTCTCTAAAAGTGGATGTGGAGAAATTCTTTCAAAACTTCATTAGCAATCCAAACAAACAGCTCACACGACGCAA
ATCATCTGCAGACCTGCAGGATGCACTTCGCGCCATCTCCAAGAAACTGAATAATTTTACGCATGGCCTCAAAACCGA
TGTGAATCGAAATGGAAGCGGTAATGGTGATGTCTCTTCGGATTCGCCAGATTTCATAGAGGACGATGATAAGATTAC
TTCGCGGACCATCAGCGATCCCACCTATCCGGTATTCAACACTAACGGCCAGCAGATCTCGCGCAGTTTGTTTCAGCA
ATTTCTGGATCAGTATCGTAAATTGTGGGGTGTTGCTAGTGAGCAGGCGCACGAGGATGCCGAGCTAGCCGCTCTGGT
AGCCGAGTTCCAGGAGTTCAACGCCGAGATCCAAAAGCTCGACGAGCACATGAGACAGCAAGCAGCGGAAGCATCGTC
TGCCGATAGGAATCTCAACGTTTCCGCAGCCAAAACTCCGCTGGACAAGCGATCCATGACGCTGCCATTGAAATCAGC
AGGAGAATCTACTTTCGGAGAGCGTGCGTCCGGACGCAGTGGAGCTGGTGGAGTACCACTAACACCCCTGATGGCCAA
ACTATCTGTTCTGGCTCTAAGCGAAACAACGCCCATCGAGATACAAACTCCGCTGACAACCAGTAAGGTTTTCCCACG
GCGAAGTTCACTGAAGTGCGAGGATGCAGTGGATGCATTGGCTGCCTTGACCACAGCCCCTGCTCAACCTCCGGGTCC
AATTCAACCAGATGGCTTGCAAAGAACTGAACTCTATATATGCGGACAGCAGAATATGACCTTATTATTGCTCATGGA
GGAGGGTACTTGTCAACAACAGCAGGTTGTGCAGAAGATGTTCGACATTTGTGTGGCCAAGTTCCCGCACATGGAATC
TCAACTGAATCAAACCTTAAATGTAAATGTGGAGGGCGACAATCGCGACGGGAGCAACTATAGCTTCATGTGCGTGGA
CTCCAAGTGGGATGTTCTGCAGCGGAATGGCCCTTGGAATCCCCTAGAGCTTAATATCCTCGAGAGCATGCACTCGAT
ACATTCCAGTGGTCATCATCTTACAGATTTGATCTTGACATCCAACGACTCCGTTTATTATGGCCATAAGAATGGAAG
GACCGAGTTCTTCTACAAGGAACCTACCCATCAGATCAATGGCATACCACCGCCCTCGGATCCGATTGGCAATATACA
ATCCCGCGCCAAGTCGCGACTGGAACGTGATCATTCCTACATGCTGTTCTAGGCTGTGCAATGGATCGTATATTATAA
ACATATTTAAATACTCGCATGCTTAGCCAAAAACAGATAATGTAATCGGGGACACCAGATAGTCTGGGTCCCCGAAGA
ATAGCCAACTTAATGCCATCCACTGTTATTTCATTTGCGATCTCTGGCTGATTCCTTCGTGAGTCTTTTCTTTTGTAT
AGTGGTTAGATAATGATTCCATATCATATACAATGCAAACCAAGGGAACTCAATTTTAAACGATCTAAATTTTACTTC
GACTTTTATACAACAAATTTATAAGAAACATTGCCGACCTTTTTTACCGCCATTCAATGGACTCACGAAGGAAACCAA
AAGAATTTTAGATATGCCGCTTACAGCCAGCGAAATATTAAGCCTTGTTTGAATTTTCACTTGATTGATGTAAAGTAC
AAAAAATGTTTTAAGCTTTGTTTACAATGTCCAGCACTGTTGTTTAATTTATAAGCTTGTATCCTATACAATTATTTA
ATCATTTTGCATTTGCTTTGACCGAAAAGATGCGACATTTTGCACTGATTTCGAGAGCCAAAGAATTTAAATCAAGGT
TTTTAATTGTAAATATACATTATACAAAATTAGATTCATTTAAATGGAATAATGTGTAACTAACCTAAAATTCACACA
GATTCCGTTCTGTCCAGTTGCAAACATAAACCTATCTTAGCTGTTTCTCATTATCAAAGATTAAGCGCTTTGTGCCAA
TTTAAATGCAGGATAAATGCTTAAAATAAACCGTCAAATATGTAGGAACGTG
```

FIG. 15
SEQ ID NO.:2
Drosophila HPS4 cDNA sequences: isoform RA

```
CGCTATTGGCTTGTTGACTTATCAGAATCGTCGGTCGTTAAATGTGATAAGGAGCCACGATGCAGCGCTAGACTTGGA
AGCACCGAAATCCACTAGATTTCAGGAGCAATGTTTCGGGATTGGCGCAAAACCAAGCACAAGCGATGGCAGAAGGTG
CAGCAGAAGCAGCAGACCTCAATCCTCACCGAAAGGGAGACGATGATTGTGTTTGTCTACGACACAGAGTGTCTCACA
GACGAGGCGGATGATCCCATATCGGCGGTGCTCTACTTCCATCCAAGCTGGGTGTCCGACTCCCAGAAGGTGGCTCTG
TGTGGTCAGCTTATGGGCACGTCGTATTTCCTCAAGGATTGCTTCTTTAATCCCCGCATCCTGGCGCTGCAGAATGGA
AAATTTGTGCTGAAGGAATTCGGTCGTTTTATTCTGGCAATTGGCACTGATCGAAATATTGGAGATCAACTGTTGGAA
CATCGTGCTGATCTGCTGAGTTCCCTGCTCAAGTTTTTCCACCGTGACGTCCAGACATTGTATGCCCAGTATGCTGCA
CCGCCCGCCCTGAACCGCCGGAATCTCAGCGAGAAACTGTACCACATCTTTGAAACATATCTGCCGATGCTGCAGCGC
AACGGAAATACATTTCAAAATGTGCCGAGCTGCGAATGCCAAAGACGGCCAGTCATATATTCCTGGAGGCTATACAA
ACGTTGCAAAGTTGCCAGCAGACAAAGGGAATACTTGGCGGAGCGATTCTGTACCACAACAAGGTGGTTGCCTCGCAA
CTGAGCGATATGGTGACCAAGCATCTTGTACTCACCGATCCTCTGCACATCCGCACTGCGGCCGAGCAAGTGACCAAC
CATCCTGAGTTCCACATACCCAACGGCGTTCAGATGCTGGTGGTTTATTTGGAGCATATGCAGTACCGCCAGTTAGCT
GGCGAGGCACAGCGCGCCCAGAACCTGCAGATGAACACAGCTCAGCTCACCCAAAATGGTATGCCGTTTCAGTATGCC
AAGCGTAAGATAAAGCGGGACAAGTCGCTCATTTTTACCCATATACCCGAGGAGGAGCACGCCCCGGAGCAGCAGGGA
GCAGTTGAACAGCTACCACCAGCCAGGCCCAAATCTATGCGACCCACCCACCTGCCGTTGCGTATAAAAAGCATGCAG
AGCAAAGAGCTACCGGAGTCTGGCATTGCATCAATAAATTTCGACGAAACCGATTCCTATCCGCAGTTCATTGGACGA
ACCAGCGTTTGCAATACTCCAATGACCGAGAACAAGGTACTGCCGGTGGCCAATGTTATGTCCATTTGCGCAAATCCC
GAAGATGAGGGCAAAGAGGAGGATATTCACAATTCCAATGGCAAGACACATTCGCGTCGAAATTCTCTAAAAGTGGAT
GTGGAGAAATTCTTTCAAAACTTCATTAGCAATCCAAACAAACAGCTCACACGACGCAAATCATCTGCAGACCTGCAG
GATGCACTTCGCGCCATCTCCAAGAAACTGAATAATTTTACGCATGGCCTCAAAACCGATGTGAATCGAAATGGAAGC
GGTAATGGTGATGTCTCTTCGGATTCGCCAGATTTCATAGAGGACGATGATAAGATTACTTCGCGGACCATCAGCGAT
CCCACCTATCCGGTATTCAACACTAACGGCCAGCAGATCTCGCGCAGTTTGTTTCAGCAATTTCTGGATCAGTATCGT
AAATTGTGGGGTGTTGCTAGTGAGCAGGCGCACGAGGATGCCGAGCTAGCCGCTCTGGTAGCCGAGTTCCAGGAGTTC
AACGCCGAGATCCAAAAGCTCGACGAGCACATGAGACAGCAAGCAGCGGAAGCATCGTCTGCCGATAGGAATCTCAAC
GTTTCCGCAGCCAAAACTCCGCTGGACAAGCGATCCATGACGCTGCCATTGAAATCAGCAGGAGAATCTACTTTCGGA
GAGCGTGCGTCCGGACGCAGTGGAGCTGGTGGAGTACCACTAACACCCCTGATGGCCAAACTATCTGTTCTGGCTCTA
AGCGAAACAACGCCCATCGAGATACAAACTCCGCTCAACAACCAGTAAGGTTTTCCCACGGCGAAGTTCACTGAAGTGC
GAGGATGCAGTGGATGCATTGGCTGCCTTGACCACAGCCCCTGCTCAACCTCCGGGTCCAATTCAACCAGATGGCTTG
CAAAGAACTGAACTCTATATATGCGGACAGCAGAATATGACCTTATTATTGCTCATGGAGGAGGGTACTTGTCAACAA
CAGCAGGTTGTGCAGAAGATGTTCGACATTTGTGTGGCCAAGTTCCCGCACATGGAATCTCAACTGAATCAAACCTTA
AATGTAAATGTGGAGGGCGACAATCGCGACGGGAGCAACTATAGCTTCATGTGCGTGGACTCCAAGTGGGATGTTCTG
CAGCGGAATGGCCCTTGGAATCCCCTAGAGCTTAATATCCTCGAGAGCATGCACTCGATACATTCCAGTGGTCATCAT
CTTACAGATTTGATCTTGAGATCCAACGACTCCGTTTATTATGCGCATAAGAATGGAAGGACCGAGTTCTTCTACAAG
GAACCTACCCATCAGATCAATGGCATACCACCGCCCTCGGATCCGATTGGCAATATACAATCCCGCGCCAAGTCGCGA
CTGGAACGTGATCATTCCTACATGCTGTTCTAGGCTGTGCAATGGATCGTATATTATAAACATATTTAAATACTCGCA
TGCTTAGCCAAAAACAGATAATGTAATCGGGGACACCAGATAGTCTGGGTCCCCGAAGAATAGCCAACTTAATGCCAT
CCACTGTTATTTCATTTGCGATCTCTGGCTGATTCCTTCGTGAGTCTTTTCTTTTGTATAGTGGTTAGATAATGATTC
CATATCATATACAATGCAAACCAAGGGAACTCAATTTAAACGATCTAAATTTTACTTCGACTTTTATACAACAAATT
TATAAGAAACATTGCCGACCTTTTTTACCGCCATTCAATGGACTCACGAAGGAAACCAAAAGAATTTTAGATATGCCG
CTTACAGCCAGCGAAATATTAAGCCTTGTTTGAATTTTCACTTGATTGATGTAAAGTACAAAAATGTTTTAAGCTTTG
TTTACAATGTCCAGCACTGTTGTTTAATTTATAAGCTTGTATCCTATACAATTATTTTAATCATTTTGCATTTGCTTT
GACCGAAAAGATGCGACATTTTGCACTGATTTCGAGAGCCAAAGAATTTAAATCAAGGTTTTTAATTGTAAATATACA
TTATACAAAATTAGATTCATTTAAATGGAATAATGTGTAACTAACCTAAAATTCACACAGATTCCGTTCTGTCCAGTT
GCAAACATAAACCTATCTTAGCTGTTTCTCATTATCAAAGATTAAGCGCTTTGTGCCAATTTAAATGCAGGATAAATG
CTTAAAATAAACCGTCAAATATGTAGGAACGTGAGAACGAA
```

FIG. 16
SEQ ID NO.:3
Drosophila HPS1 cDNA

```
TTACCCAGCACCAGTGACACTGGTGAAAGTTTTGTTGTGTATTTGGTGTTTTGCCAATGCTGATAAGAAAATGAACGG
ACTGATTGTGTTTAACAGCGCCAACGATGTTGTATACCAGAAGCTTAACGAGCCGCTGGCGCAGAAGATCCGGAGTGT
GGCCACCACCCAGGGCCTGCTCCAGTCCGGCGGCTCCCTGGACAGCAACATACTGCTGCAGATTTTCAGCCCCATCGT
TGGATCTCAGCGAATAATGCAGTGCCAGTTCGATAATGCCTACTCCAGCCTGCAGTGTGAGCAAGGCTTCAATTTGGT
GTTCGGCGAACTTCTTGGCTTCACCTTTCTGAAGATCGGACAAATACCCGTGGAGCTGCTGGGTCGCCAAATGGGTGT
GGCCATTACGCTGACGCGCTATTGTTACGGCGCCAATTTGTTTGCCGCCCAGGCGGGGGCCATGCAACAGGAGTTGCT
GACGCAGTGCCTCGACTGCTATGAGACTTTGTTGTGGGAGGAGGATCAGACGTACCTGCTGGAGGCCATGCCCAGGCT
GCTGATCAACACGGAACTAAAGAGGACAGTGCATCTGACGCTGGACGCCACGCTTGAGCACTTGCGCCAGCTCGGACT
GCCCCGAGCCCACGCCCTGTTGCTCGTTTCCAACAAGCTGGTGGCCGCGAACAGCACTCGGCAAGCTCTGCCGCTTGC
TGCCGCCGACCTACTCTTCCTCAGCCTCATGTCACGCGCCCTGCAAGCGCCAAAGTCCCCTTCCCAGCGAGCAGTAGC
TGTATTCCTGCAGGGTGTCTCCTATGATGTGAACTCTGGCTGCGTTCCCAGTATCGTGCACATCTCGCGTCTCCATGG
TAACCAAGTTCTCCTGCAGGTCATCGAGTACGCCCACATGCCACTGACCAGCTGCATCTACGATTCCTTCTTTGTGCT
TCAAAAAATCGTGGCTGTTCAGCATCAGGGCGATTCGGATGCCCTGAAGCCCGCCTTCGAGAACCTCGAATCGTTTAT
TGTGCAGGCCTTGACCGCTTTGAAGCGATATCTGAAACAGCGATCGGAAACCGATGACCTAGAGAACTGCACGAAGAA
GTTCGCCGCTAAATGGGAGAATCTTCGCAAGATGTACACTGAGTACTTCAAGAACTTTGAGCGGGAGCTGCTCGTGAG
GATTGAGTCGAATTTGCCCTCGTTCGGAGAGGAACTGAAGCAGATATTCACACTGGCCTGCTGCGACAGCTCAAGTGT
CCATGAGCTGGATCAACTCTCTGATACGGCAGCGAATGTGGAAGCCAAGCTACTGGAGTTCGCTGAATTTCTGGCCGT
TAAGGCCACTCGTAACATATCCATTGATGCTTATTTGGAGGATTTTCCGGGTCTGGTGCACTTTATGTACGTCAATCG
CAGCCGAGGACAAATGCTTGCTCCGGATCTGCGACCGAACCAGCTGGTGCCAAAGACAAAACTCTGGAGCATGGTGGA
GATCGCGAGAAATTACCTTAAGAAGGGCCAGACCACAGTGATGTGGAAGGATAAGGCATTCCATTACTCGTACTTCCT
CTGGTTCGAGGACATGTCTGGTGGCGTTCTTAGTACCGTCGTGGATTTGCAGCACCACTTTCTGTCCACAGGAGCAGC
CAGTGGCAACGGTTCGAAATCCCCAACAGAACCAGGTGCTCTTACAATGGACTATTACCACGATCTGGCGGAGTTGTG
CTTCCCCAAGCTGTCACCGGCCAAAGTGCGCGTCTACGAGTTGTATTGCATTCATCTGGGACTGGTAACCGCCACATG
CGCCGTGGAGCATGCACGTCGCCTGGTGGCCACCATCAGTGATGTTGTGGGCGAGGAAGCGTTTTAAGTGCATTGGCC
ATTGGTCATTCCAGATTTATAACATGATTTCTAGTCAATTTTCGAGACTCCTAGGCGAGATAATCCACTCGAAATTTT
GTTAGGTTTAGGACAACTATCATCCACTGTTATAGGCTACACAACAAGGATATTTGTAAAGTTATTGGAAACATATAT
ATTTTCTTCAACCGGCAATAAAAATGTAACA
```

FIG. 17

SEQ ID NO.:4
>Human HPS1 cDNA atgaagtgcgtcttggtggccactgagggcgcagaggtcctcttctactggacagatcaggagtttgaagagagtctccggctgaa
gttcgggcagtcagagaatgaggaagaagagctccctgccctggaggaccagctcagcaccctcctagccccggtcatcatctcct
ccatgacgatgctggagaagctctcggacacctacacctgcttctccacggaaaatggcaacttcctgtatgtccttcacctgttt
ggagaatgcctgttcattgccatcaatggtgaccacaccgagagcgaggggacctgcggcggaagctgtatgtgctcaagtacct
gtttgaagtgcactttgggctggtgactgtggacggtcatcttatccgaaaggagctgcggcccccagacctggcgcagcgtgtcc
agctgtgggagcacttccagagcctgctgtggacctacagccgcctgcgggagcaggagcagtgcttcgccgtggaggccctggag
cgactgattcaccccagctctgtgagctgtgcatagaggcgctggagcggcacgtcatccaggctgtcaacaccagcccgagcg
gggaggcgaggaggccctgcatgccttcctgctcgtgcactccaagctgctggcattctactctagccacagtgccagctccctgc
gcccggccgacctgcttgccctcatcctcctggttcaggacctctacccagcgagagcacagcagaggacgacattcagcctcc
ccgcggagggccggagcagccagaacatccccgtgcagcaggcctggagcctcactccacgggcccaactgggggagctctgc
agagacggagacagacagcttctccctccctgaggagtacttcacaccagctccttccctggcgatcagagctcaggtagcacca
tctggctggaggggggcacccccccatggatgccttcagatagcagaggacacctccaaacactggttcccactgcctgtg
ccttccggcccagaaggatcttcctggatgccaacgtgaaggaaagctactgcccctagtgccccacaccatgtactgctgcc
cctgtggcagggcatcaacctggtgctcctgaccaggagcccagcgcgccctggccctggttctgtcccagctgatggatggct
tctccatgctggagaagaagctgaaggaagggccggagcccggggcctccctgcgctcccagccctcgtgggagacctgcgccag
aggatggacaagtttgtcaagaatcgagggacaggagattcagagcacctggctggagtttaaggccaaggctttctccaaaag
tgagcccggatcctcctgggagctgctccaggcatgtgggaagctgaagcggcagctctgcgccatctaccggctgaactttctga
ccacagcccccagcaggggaggcccacacctgcccagcacctgcaggaccaagtgcagaggctcatgcgggagaagctgacggac
tggaaggacttcttgctggtgaagagcaggaggaacatcaccatggtgtcctacctagaagactcccaggcttggtgcacttcat
ctatgtggaccgcaccactgggcagatggtggcgccttccctcaactgcagtcaaaagacctcgtcggagttgggcaaggggccgc
tggctgcctttgtcaaaactaaggtctggtctctgatccagctggcgcgcagatacctgcagaagggctacaccacgctgctgttc
caggaggggggatttctactgctcctacttcctgtggttcgagaatgacatggggtacaaactccagatgatcgaggtgcccgtcct
ctccgacgactcagtgcctatcggcatgctgggaggagactactacaggaagctcctgcgctactacagcaagaaccgcccaaccg
aggctgtcaggtgctacgagctgctggccctgcacctgtctgtcatccccactgacctgctggtgcagcaggccggccagctggcc
cggcgcctctgggaggcctcccgtatccccctgctctag

SEQ ID NO.:5
>Human HPS4 cDNA atggccacctctacctccacagaggcaaagtcagcctcgtggtggaattatttttttctttatgatggttccaaggtaaaggaaga
aggcgatccaacaagagctggcatttgttacttttatccttcccagaccctgctagaccaacaggagttgctttgtggacagattg
ctggagttgtccgctgtgtttctgacatttctgactctcctcctactcttgttcgtctgagaaaactgaagtttgccataaaagtt
gatggagattacctttgggtgctgggctgtgctgtggagctccctgatgtcagctgcaagcggtttctggatcagctagttggatt
ctttaatttttacaatggacctgtttccctagcttatgagaactgttctcaggaagaactgagcacggagtgggacaccttcatcg
agcaaattctgaaaaacaccagtgatctgcataagattttcaattccctctggaacttggaccaaactaaagtggagccctgttg
ttgctgaaggcagcccgcattctgcagacctgccagcgctcgcctcacattctcgctggctgcatcctctataaaggactgattgt
cagcacccaactcccgccctcctcaccgccaaggtcctgcttcaccgaacagcacctcaggagcagagactccctacggagagg
atgccccgcaggaacatggagcggcattgccccgaatgtccagattatccctgttttgtgaccaaagaggaagccattagtctc
cacgagttcccggtggaacagatgacaaggtctctagcatctccagcaggactccaggatggttcagcccagcaccatccaaaggg
tgggagcacatctgcctgaaagaaaacgccactggccatgtggaatccatggcctggaccaccccagatcccacatccctgacg
aagcttgtccagatggcaggaaggagaaccggatgcttgtctggccatgatctggagagcatcaggcccgcaggactgcacaactct
gccaggggtgaggttctcagctcctccctggggaaggaactagtcttcttcctccaagaagaacctgacttgtctgaaatcca
cattccagaggctcaggaagtggaaatggcctcaggtcattttgccttcctacatgtgcctgttccagatggcagggctccttact
gcaaggcatctctcagcgcctccagcagcctggaacccacgcctcctgaggacacagccatcagcagcttgcgccctccctctgct
cctgagatgctgacccagcatggagcccaagagcagctcgaagaccatcctggccatagcagccaagccccccattcccagagcaga
ccctctccccagaaggacccgcaggcccttgttattgcctcgcttagatccaggacagagaggaaacaagcttcccacggggaac
aaggcctggatgaggatgttgatggggtctgtgaaagccacgcagccctggtctggaatgcagttcaggctcagcaaactgtcag
ggtgctggccctctgcagatggaatcagctccaggctgacaccagcagatgcctgcatgggctcgtgaggatgaatctctacac
tcactgcgtcaaagggctggtgctgtccctgctggctgaggagccgctgctgggagacagcgcagccatagaggaagtgtaccaca
gcagcctggcttcactgaatgggctggaagtccacctgaaagagacgctgcccagggatgaggcagcctccacgagcagcacctac
aacttcacacattacgaccgcattcagagcttgctgatggcaaacctgccgcaggtggccaccccgcaggatcgccgcttcctcca
ggccgtcagcctgatgcatagcgaatttgcccagctgcccgcgctttatgaaatgactgtcagaaatgcctccacggctgtgtacg
cctgttgcaacccccatccaggagacatatttccagcagctggcacctgcagcacggagctccggcttcccaaaccctcaggatggc
gccttcagcctctccggcaaagcaaagcagaagctgctgaagcacggggtgaacttgctctga

FIG. 22

(A) DROSOPHILA CG6969 (SEQ ID NO.: 6)

MTDETTPLTDAVPSGSGYVVLPPYQGPERVFPGGVSPRARRNKMRQFQCCMGITFIAIVFTALCLALVFSDSLGGADG
GPSFFFVVNGSDSELAPNRPLPDEPAAEWALQQAALGHHDGAQAVSAGIKALGDREILEEGLQPNEVNTPSFRHYRSL
STNPEARKLARRGYVENQATIDIAKRFNYTKQPGRSNIGWGPKIVLPDPTVLRLECDFNARYRRSTGVCNNKQHPRTY
GASMVPYRRMVSPDYADGIAAPRVSHHGRLPPARQVSLKIHRSSYETDSNFTVMLAVFGQFMDHDITATSLTTSQEGE
SIDCCVAATREQHPECYPVDILPDDPYYKQYNISCMNFVRSAPAPTGRFGPRMQLNQATAFIDASVVYGNLEQRQNQL
RSFINGSLRMFVTDDGRQLLPISSNPADGCNRVQMTRLGKYCFESGDDRANENLLLTSMHLLWARHHNYLARQLQEQN
PHWEDERLYQEARKILGAQMAHITYNEFLPVLLGKNISEAKGLLPAKHNLNAPDTYDPEVDPSIANCFAAAAFRFAHT
LLPGLFNISRDNSTPEAIELHKMLFNPFSLWAEHGIDHALMTAANTPVMQVDRFFSLEVTQXLFEGTAEDRVPLCGLD
LVSLNIQRGRDHGIPSYPVFRRHCRLPTVDTWEEMSQAIDNATLDSIRQIYESPQDVDVYTGALSEPPLDGAIFGPLL
SCMVSDQFLRLKLGDSHWYERKMGPQKFTKAQLAEIYKTSLAAIICRNSDGITRVREHVMQRLRDGGNHHVDCQDLEG
FHFNFEPWSEKQQPQDLHSAGISRGSTSVRVMSKANHQAHNVTLHIDKGI (B) HUMAN TPO (SEQ ID NO.: 7)                                          % identity: 34%

MRALAVLSVTLVMACTEAFFPFISRGKELLWGKPEESRVSSVLEESKRLVDTAMYATMQRNLKKRGILSPAQLLSFSK
LPEPTSGVIARAAEIMETSIQAMKRKVNLKTQQSQHPTDALSEDLLSIIANMSGCLPYMLPPKCPNTCLANKYRPITG
ACNNRDHPRWGASNTALARWLPPVYEDGFSQPRGWNPGFLYNGFPLPPVREVTRHVIQVSNEVVTDDDRYSDLLMAWG
QYIDHDIAFTPQSTSKAAFGGGADCQMTCENQNPCFPIQLPEEARPAAGTACLPFYRSSAACGTGDQGALFGNLSTAN
PRQQMNGLTSFLDASTVYGSSPALERQLRNWTSAEGLLRVHARLRDSGRAYLPFVPPRAPAACAPEPGIPGETRGPCF
LAGDGRASEVPSLTALHTLWLREHNRLAAALKALNAHWSADAVYQEARKVVGALHQIITLRDYIPRILGPEAFQQYVG
PYEGYDSTANPTVSNVFSTAAFRFGHATIHPLVRRLDASFQEHPDLPGLWLHQAFFSPWTLLRGGGLDPLIRGLLARP
AKLQVQDQLMNEELTERLFVLSNSSTLDLASINLQRGRDHGLPGYNEWREFCGLPRLETPADLSTAIASRSVADKILD
LYKHPDNIDVWLGGLAENFLPRARTGPLFACLIGKQMKALRDGDWFWWENSHVFTDAQRRELEKHSLSRVICDNTGLT
RVPMDAFQVGKFPEDFESCDSITGMNLEAWRETFPQDDKCGFPESVENGDFVHCEESGRRVLVYSCRHGYELQGREQL
TCTQEGWDFQPPLCKDVNECADGAHPPCHASARCRNTKGGFQCLCADPYELGDDGRTCVDSGRLPRVTWISMSLAALL
IGGFAGLTSTVICRWTRTGTKSTLPISETGGGTPELRCGKHQAVGTSPQRAAAQDSEQESAGMEGRDTHRLPRAL (C) HUMAN EPX (SEQ ID NO.: 8)                                          % identity: 35%

MHLLPALAGVLATLVLAQPCEGTDPASPGAVETSVLRDCIAEAKLLVDAAYNWTQKSIKQRLRSGSASPMDLLSYFKQ
PVAATRTVVRAADYMHVALGLLEEKLQPQRSGPFNVTDVLTEPQLRLLSQASGCALRDQAERCSDKYRTITGRCNNKR
RPLLGASNQALARWLPAEYEDGLSLPFGWTPSRRRNGFLLPLVRAVSNQIVRFPNERLTSDRGRALMFMQWGQFIDHD
LDFSPESPARVAFTAGVDCERTCAQLPPCFPIKIPPNDPRIKNQRDCIPFFRSAPSCPQNKNRVRNQINALTSFVDAS
MVYGSEVSLSLRLRNRTNYLGLLAINQRFQDNGRALLPFDNLHDDPCLLTNRSARIPCFLAGDTRSTETPKLAAMHTL
FMREHNRLATELRRLNPRWNGDKLYNEARKIMGAMVQIITYRDFLPLVLGKARARRTLGHYRGYCSNVDPRVANVFTL
AFRFGHTMLQPFMFRLDSQYRASAPNSHVPLSSAFFASWRIVYEGGIDPILRGLMATPAKLNRQDAMLVDELRDRLFR
QVRRIGLDLAALNMQRSRDHGLPGYNAWRRFCGLSQPRNLAQLSRVLKNQDLARKFLNLYGTPDNIDIWIGAIAEPLL
PGARVGPLLACLFENQFRRARDGDRFWWQKRGVFTKRQRKALSRISLSRIICDNTGITTVSRDIFRANIYPRGFVNCS
RIPRLNLSAWRGT

FIG. 22

(D) HUMAN MPO        (SEQ ID NO.: 9)                                        % identity: 34%

MGVPFFSSLRCMVDLGPCWAGGLTAEMKLLLALAGLLAILATPQPSEGAAPAVLGEVDTSLVLSSMEEAKQLVDKAYK
ERRESIKQRLRSGSASPMELLSYFKQPVAATRTAVRAADYLHVALDLLERKLRSLWRRPFNVTDVLTPAQLNVLSKSS
GCAYQDVGVTCPEQDKYRTITGMCNNRRSPTLGASNRAFVRWLPAEYEDGFSLPYGWTPGVKRNGFPVALARAVSNEI
VRFPTDQLTPDQERSLMFMQWGQLLDHDLDFTPEPAARASFVTGVNCETSCVQQPPCFPLKIPPNDPRIKNQADCIPF
FRSCPACPGSNITIRNQINALTSFVDASMVYGSEEPLARNLRNMSNQLGLLAVNQRFQDNGRALLPFDNLHDDPCLLT
NRSARIPCFLAGDTRSSEMPELTSMHTLLLREHNRLATELKSLNPRWDGERLYQEARKIVGAMVQIITYRDYLPLVLG
PTAMRKYLPTYRSYNDSVDPRIANVFTNAFRYGHTLIQPFMFRLDNRYQPMEPNPRVPLSRVFFASWRVVLEGGIDPI
LRGLMATPAKLNRQNQIAVDEIRERLFEQVMRIGLDLPALNMQRSRDHGLPGYNAWRRFCGLPQPETVGQLGTVLRNL
KLARKLMEQYGTPNNIDIWMGGVSEPLKRKGRVGPLLACIIGTQFRKLRDGDRFWWENEGVFSMQQRQALAQISLPRI
ICDNTGITTVSKNNIFMSNSYPRDFVNCSTLPALNLASWREAS (E) HUMAN LPO   (SEQ ID NO.: 10)                                           % identity: 32%

MRVLLHLPALLASLILLQAAASTTRAQTTRTSAISDTVSQAKVQVNKAFLDSRTRLKTAMSSETPTSRQLSEYLKHAK
GRTRTAIRNGQVWEESLKRLRQKASLTNVTDPSLDLTSLSLEVGCGAPAPVVRCDPCSPYRTITGDCNNRRKPALGAA
NRALARWLPAEYEDGLSLPFGWTPGKTRNGFPLPLAREVSNKIVGYLNEEGVLDQNRSLLFMQWGQIVDHDLDFAPDT
ELGSSEYSKAQCDEYCIQGDNCFPIMFPPNDPKAGTQGKCMPFFRAGFVCPTPPYKSLAREQINALTSFLDASFVYSS
EPSLASRLRNLSSPLGLMAVNQEVSDHGLPYLPYDSKKPSPCEFINTTARVPCFLAGDSRASEHILLATSHTLFLREH
NRLARELKRLNPQWDGEKLYQEARKILGAFVQIITFRDYLPILLGDHMQKWIPPYQGYSESVDPRISNVFTFAFRFGH
LEVPSSMFRLDENYQPWGPEPELPLHTLFFNTWRMVKDGGIDPLVRGLLAKKSKLMKQNKMMTGELRNKLFQPTHRIH
GFDLAAINTQRCRDHGQPGYNSWRAFCDLSQPQTLEELNTVLKSKMLAKKLLGLYGTPDNIDIWIGAIAEPLVERGRV
GPLLACLLGKQFQQIRDGDRFWWENPGVFTNEQKDSLQKMSFSRLVCDNTRITKVPRDPFWANSYPYDFVDCSAIDKL
DLSPWASVKN (F) MOUSE MPO  (SEQ ID NO.: 11)                                            % identity: 35%

MKLLLALAGLLAPLAMLQTSNGATPALLGEVENSVVLSCMEEAKQLVDRAYKERRESIKRTLQSGSASPTELLFYFKQ
PVAGTRTAVRAADYLHVALDLLKRKLQPLWPRPFNVTDVLTPAQLNLLSVSSGCAYQDVGVTCPPNDKYRTITGHCNN
RRSPTLGASNRAFVRWLPAEYEDGVSMPFGWTPGVNRNGFKVPLARQVSNAIVRFPNDQLTKDQERALMFMQWGQFLD
HDITLTPEPATRFSFFTGLNCETSCLQQPPCFPLKIPPNDPRIKNQKDCIPFFRSCPACTRNNITIRNQINALTSFVD
ASGVYGSEDPLARKLRNLTNQLGLLAVNTRFQDNGRALMPFDSLHDDPCLLTNRSARIPCFLAGDMRSSEMPELTSMH
TLFVREHNRLATQLKRLNPRWNGEKLYQEARKIVGAMVQIITYRDYLPLVLGPAAMKKYLPQYRSYNDSVDPRIANVF
TNAFRYGHTLIQPFMFRLNNQYRPTAANPRVPLSKVFFASWRVVLEGGIDPILRGLMATPAKLNRQNQIVVDEIRERL
FEQVMRIGLDLPALNMQRSRDHGLPGYNAWRRFCGLPQPSTVGELGTVLKNLELARKLMAQYGTPNNIDIWMGGVSEP
LEPNGRVGQLLACLIGTQFRKLRDGDRFWWENPGVFSKQQRQALASISLPRLICDNTGITTVSKNNIFMSNTYPRDFV
SCNTLPKLNLTSWKET

FIG. 22

(G) MOSQUITO ENSANGP00000019765 (SEQ ID NO.: 12)      % identity: 54%

```
GSIGQRCPTIVVADESSPEWNGTAVSDDAKAAAIADGEKALGDKELLEETLSSPPLNSPSFRHQKSVGATKAARLAAK
VGFVEDRATQALVRRLDIRRRGSIGRGPPMDLPRAHRQPRCDFNARYRTANGTCNSKERPYEYGVAMIPFRRQLNPDY
GDGISAPRASVDGAELPSARQVSLEIHRPSYHNDPNFSVMLAVWGQFLDHDITSTALNQGVDGKPIECCDPGQPQHPE
CFPVPLGPGDPYYTQYNVTCMNFVRSVPAPTGHFGPRQQLNQATAFIDGSVVYGSDDERMGALRTGAGGQLRMLRTPD
GRDLLPVSTDPLDGCNEQEMNAAGKYCFESGDARANENLHLTSMHLIWARHHNSLARGLARANPHWDDERLFQEARRI
LAAQMQHITYAEFVPVIVGNETAGRMGLLPVSAGGEPAGDTYNATVDASIANVFAGAAFRFAHTLLPGLMKQTRNPAA
SASGIELHRMLFNPYSLYARDGLDNALGGAIGTALAKYDQYFSTELTERLFEKADEHLLHGQPCGLDLVSLNIQRGRD
HGLPAYPRWRKHCHLTPADSWEELERIVDPESYRQMRRIYREPANVDVYSGALSEAPVRDGIVGPLLTCLIGDQFLRL
KQGDSFWYERRRGPQRFTEAQLQQIYNTKLSSIICRNSDHIEQSPVYLMKRTDSRTNPETDCKQLDTFDFEPFREDAE
QPQ
```

(H) DOG MPO (SEQ ID NO.: 13)      % identity: 34%

```
MHCALRTYWASGLVAEMLLLLALAGLLAILAVPQHSESANPAVLEVETTVVMTCMEEAKRLVDTAYKERRESIKQRLH
SGLASPMELLSYFKQPVAATRTAVRAADYLHVALSLLEGKLRPLWPRPFNVTDVLTPAQLNLLSKSSGCAYQDVGLKC
PENDKYRSITGHCNNRRSPTLGASNRAFARWLPAEYEDGFSLPYGWTPGVKRSGFPVPLARAVSNAIVRFPTEQLTPD
QERSLLFMQWGQLLDHDLDLSPEPAARVSFVTSVNCEISCEQQPPCFPLKIPPNDPRIKNQRDCIPFFRSSPACTDNN
ITIRNQINALTSFVDASMVYGSEDPLATRLRNLTNQLGLLAVNTRFSDNGRALLPFDNLHDDPCLLTNRSAGIPCFLA
GDTRSSEMPELASMHTLFLREHNRLATELRRLNPRWDGERLYQEARKIVGAMVQIITYRDYLPLVLGPLAMRKYLPRY
RSYNDSVDPRISNVFTNAFRYGHTLIQPFMFRLDNRYQPMGPNPRVPLSRVFFATWRVVLEGGIDPILRGLMATPAKL
NRQNQIVVDEIRERLFEQVMRIGLDLPALNMQRSRDHGLPGYNAWRRFCGLPQPSTVGELATVLRNLDLAQKLMQQYG
TPDNIDIWMGGVAEPLEPRGRVGQLLACLIGTQFRKLRDGDRFWWENRGVFSSQQQQALARISLPRIICDNTGITTVS
KNNIFMSNMFPRDFVNCSTLPALDLTSWRDSN
```

(I) C. ELEGANS C46A5.4 (SEQ ID NO.: 14)      % identity: 33%

```
MKQEIITTAASSAVRLTEKLFNDTEKLMSDKFDGKLGNWLKSPKTLKSMIQFLPTENTKMKEICPVNQIEECVIGKYR
SYTGHCNNVKNPLNGASYERLKRFLPADYSDGISAPRSSKSGQPLPSSRALSALFTPSPSGHATCSLLIAPFLSFIYD
DIVHVPSNRIFKRDFYGNDKAMPLPCCRGDNSHPECFEIPVPEDDTLQSKNVKCLPYSRSLPVPNPKCSFGQRQQANM
VTSYLDLSQIYGSTEGIVKKMRLHKNGKLALRAVGGFNNQLGVPPANLDSSICRSSTGKPCLLAGNNKINFLPTSGAI
YTIWMRQHNVIADKLASVNPHWDDQKVFEEARRITIAQFQHITFNEMVPVLVGKEQLRVMGIKLQKNGYDSGYDINID
SSASNVFASAAGQFFLTLLPSQFNIEDKRFSTKSESLLKHFNDPALIYEKGRIDGMLKFLLNAPIEKPGLHSSPLLRT
AFQKKDIADSVDIIAMVIQMGRDHGLPSYLQWRTFCKLDDFSSFLALQTIFKPSVNISDFERLYESPEDIDVFVGGLS
EQPTKGSLLGPTFACLFAHQMAQTKRGDRFWYENFVSPSAFTVDQIDEIRKTTMARIICDNTDTVTHVQHHAFSLPDD
YGNCPLSCNSTGIIQVFDPKAFKDEEKLTSLPITKETVEKVIRLGLRQWQRYEEGEGRRISAQLSDSSPSALLSHALL
MAPKKESIDIARTASVLREATNILISGNGLDKDERLPDLDIGTLQKILPQIDVGSVIGNFTPFLARDPLPKEQCLPEP
LPCDHTSKYRTYSGWCNNLKNPKFGNAFTQMRRLLDPAYDDGFDTPRTRSVLGSELPSARKISNIVHSDAPKFHVKFT
HMLMQFGQILDHDMMHSPISRGPKNTILNCSSCDSAQTLSIHCFPIKIEANDPFFPSKHSDGRPRCMPFARSLLAQVS
LGFRNQLNQLTSFLDASTIYGSTQCEANKLRLFSDGKLNFTDLGFNKEALPQGNQERDCRSVLQNRQRRCFVAGDERS
NEQPGLTAIHNIFLREHNRIARYLKQINNFWSDEKLFQESRRINIAQLQHIIYKEWLPVVLGCQNMEKWGLMPQTAGY
FEGYDDQCDATISQEMSTSAPRFGHSLIRGVFTRMNDNFQNMTNHVNLTETFSNPSPVYDKNSGHMESILMGLIGANS
MAFDRHIVTAVRNHLFAKPGGPLTGLDLPAVNIQRGRDHGVQGYNAYRKHCGLRKASAFSDLRDVMNSEAVTALETAY
AHVDDIDLFPGIMSESPTRGSLVGPTLACLIGEQMQRLKKCDRFYYETSDSMVRFTPDQLVEIRKASLSRIICDNSEY
AANIQPNVFLMPDDLTNSPMTCSELSEIDLNKWVERDYCLVDERVVNRGKTKRITPCITCTCTLEGPECHSITIDDCS
RLLRDYSITDIQKDPVCLIQCSQQLKKL
```

FIG. 22

(J) ARABIDOPSIS OXIREDUCTASE    (SEQ ID NO.: 15)                                    % identity: 21%

MGFSPSSSWFLHPQLHHVVSKMSYFDAFLFYIVHLVDKLGLWHRFPVLLGVAYLGLRRHLHQRYNLVHVGPINGQGYD
TDEFCYRTADGKCNHPSDNTIGSQGSFIGRNMPPSTSQYGILDPHPSVVATKLLARKRFIDNGDQFNVIACSWIQFMI
HDWVDHLEDTHQIELEAPEEVASGCPLKSFKFLRTKKVPTDDHHKSGAVNTRTPWWDGSVIYGNDETGMRRVRVFKDG
KLKISGDGLLERDERGVPISGDIRNSWSGFSLLQALFVKEHNSVCDMLKERYPDFDDEKLYRTARLVTAAVIAKVHTI
DWTIELLKTDTLTAGMRINWYGFFGKKVKDMVGARFGPLFSGLVGLKKPNDHGVPYSLTEEFVSVYRMHCLLPETLIL
RDMNSENVDKENPAIEREIPMTELIGKKAGEKASKLGFEQLLVSMGHQSCGALTLWNYPNWMRNLVAQDIDGEDRPHL
IDMAALEIYRDRERGVPRYNEFRKNLLMSPISKWEELTDDEEAIKVLREVYEDDIEKLDLNVGLHAEKKIKGFAISET
AFFIFLLVASRRLEADRFFTTNFNEKTYTKEGLEWVNTTETLKDVIDRHFPRLTDQWMRCSSAFSVWGSDPNPKNWVP
LYLRSAP

FIG. 25A

```
CG6969       -MTDETTPLTDAVPSGSGYVVLPPYQGPERVFPGGVSPRARRNKMRQFQCCMGITFIAIV 59
mosquito     ------------------------------------------------------------
MPO (human)  ------------------------------------------------------MGVPFF 6
MPO (dog)    ------------------------------------------------------------
MPO (mouse)  ------------------------------------------------------------
EPX (human)  ------------------------------------------------------------
LPO (human)  ------------------------------------------------------------
TPO (human)  ------------------------------------------------------------
C.elegans    EQPTKGSLLGPTFACLFAHQMAQTKRGDRFWYENFVSPSAFTVDQIDEIRKTTMARIICD 60
Arabidopsis  ------------------------------------------------------------
                              :    .      :          :         : :

CG6969       FTALCLALVFSDSLGGADGGPSFFFVVNGSDSELAPNRPLPDEPAAEWALQQAALGHHDG 119
mosquito     -------------------------GSIGQRCPTIVVADESSPEWN--GTAVSDDAK 30
MPO (human)  SSLRCMVDLGPCWAGGLTAEMKLLLALAGLLAILATPQPSEGAAPAVLGEVDTSLVLSSM 66
MPO (dog)    ----MHCALRTYWASGLVAEMLLLLALAGLLAIILAVPQHSESANPAVL-EVETTVVMTCM 55
MPO (mouse)  --------------------MKLLLALAGLLAPLAMLQTSNGATPALLGEVENSVVLSCM 40
EPX (human)  --------------------MHLLPALAGVLATLVLAQPCEGTDPASPGAVETSVLRDCI 40
LPO (human)  --------------------MRVLLHLPALLASLILLQAAASTTRAQT--TRTSAISDTV 38
TPO (human)  ----------------MRALAVLSVTLVMACTEAFFPFISRGKELLWGKPEESRVSSVL 43
C.elegans    NTDTVTHVQHHAFSLPDDYGNCPLSCNSTGIIQVFDPKAFKDEEKLTSLPITKETVEKVI 120
Arabidopsis  ------------------------------------------------------------
                                       :

CG6969       AQAVSAGIKALGDREILEEGLQPNEVNTPSFRHYRSLSTNPEARKLARRG--------YV 171
mosquito     AAAIADGEKALGDKELLEETLSSPPLNSPSFRHQKSVGATKAARLAAKVG--------FV 82
MPO (human)  EEAKQLVDKAYKERRESIKQRLRSGSASPMELLSYFKQPVAATRTAVRAADYLHVALDLL 126
MPO (dog)    EEAKRLVDTAYKERRESIKQRLHSGLASPMELLSYFKQPVAATRTAVRAADYLHVALSLL 115
MPO (mouse)  EEAKQLVDRAYKERRESIKRTLQSGSASPTELLFYFKQPVAGTRTAVRAADYLHVALDLL 100
EPX (human)  AEAKLLVDAAYNWTQKSIKQRLRSGSASPMDLLSYFKQPVAATRTVVRAADYMHVALGLL 100
LPO (human)  SQAKVQVNKAFLDSRTRLKTAMSSETPTSRQLSEYLKHAKGRTRTAIRNGQVWEESLKRL 98
TPO (mouse)  EESKRLVDTAMYATMQRNLK--KRGILSPAQLLSFSKLPEPTSGVIARAAEIMETSIQAM 101
C.elegans    RLGLRQWQRYEEGEGRRISAQLSDSSPSALLSHALLMAPKKESIDIARTASVLREATNIL 180
Arabidopsis  --------MGFSPSSSWFLHPQLHHVVSKMSYFDAFLFYIVHLVDKLGLWHRFPVLLGVA 52
                                       :

CG6969       ENQATIDIAKRFNYTKQPGRSNIGWGPKIVLPDPTVLRLECDFN----------------- 215
mosquito     EDRATQALVRRLDIRR---RGSIGRGPPMDLPR-AHRQPRCDFN----------------- 122
MPO (human)  ERKLRSLWRRPFNVTDVLTPAQLNVLSKSSGCAYQDVGVTCPE----------------Q 170
MPO (dog)    EGKLRPLWPRPFNVTDVLTPAQLNLLSKSSGCAYQDVGLKCPE----------------N 159
MPO (mouse)  KRKLQPLWPRPFNVTDVLTPAQLNLLSVSSGCAYQDVGVTCPP----------------N 144
EPX (human)  EEKLQPQRSGPFNVTDVLTEPQLRLLSQASGCALRDQAERCS------------------ 142
LPO (human)  RQKAS-----LTNVTDPS--LDLTSLSLEVGCGAPAPVVRCDP----------------C 135
TPO (human)  KRKVNLKTQQSQHPTDALSEDLLSIIANMSGCLPYMLPPKCPNTC-------------LA 148
C.elegans    ISGNGLDKDERLPDLDIGTLQKILPQIDVGSVIGNFTPFLARDPLPKEQCLPEPLPCDHT 240
Arabidopsis  YLGLRRHLHQRYNLVHVGPINGQGYDTD-----------------------------E 81

CG6969       ARYRRSTGVCNNKQHPRTYGASMVPYRRMVSPDYADGIAAPR-----VSHHG-RLPPARQ 269
mosquito     ARYRTANGTCNSKERPYEYGVAMIPFRRQLNPDYGDGISAPR-----ASVDGAELPSARQ 177
MPO (human)  DKYRTITGMCNNRSP-TLGASNRAFVRWLPAEYEDGFSLPYGWTPGVKRNGFPVALARA 229
MPO (dog)    DKYRSITGHCNNRSP-TLGASNRAFARWLPAEYEDGFSLPYGWTPGVKRSGFPVPLARA 218
MPO (mouse)  DKYRTITGHCNNRSP-TLGASNRAFVRWLPAEYEDGVSMPFGWTPGVNRNGFKVPLARQ 203
EPX (human)  DKYRTITGRCNNRRP-LLGASNQALARWLPAEYEDGLSLPFGWTPSRRRNGFLLPLVRA 201
LPO (human)  SPYRTITGDCNNRRKP-ALGAANRALARWLPAEYEDGLSLPFGWTPGKTRNGFPLPLARE 194
TPO (human)  NKYRPITGACNNRDHP-RWGASNTALARWLPPVYEDGFSQPRGWNPGFLYNGFPLPPVRE 207
C.elegans    SKYRTYSGWCNNLKNP-KFGNAFTQMRRLLDPAYDDGFDTPR----TRSVLGSELPSARK 295
Arabidopsis  FCYRTADGKCNHPSDN-TIGSQGSFIGRNMPPS--------------TSQYGILDPHPSV 126
             **  *  **    *       *  :   .         .     *   .
```

FIG. 25B

```
CG6969       VSLKIHRSSYET---DSNFTVMLAVFGQFMDHDITATSLTTS-QEGESIDCCVAATREQH 325
mosquito     VSLEIHRPSYHN---DPNFSVMLAVWGQFLDHDITSTALNQG-VDGKPIECCDPGQ-PQH 232
MPO (human)  VSNEIVRFPTDQLTPDQERSLMFMQWGQLLDHDLDFTPEPAA-RASFVTGVNCETSCVQQ 288
MPO (dog)    VSNAIVRFPTEQLTPDQERSLLFMQWGQLLDHDLDLSPEPAA-RVSFVTSVNCEISCEQQ 277
MPO (mouse)  VSNAIVRFPNDQLTKDQERALMFMQWGQFLDHDITLTPEPAT-RFSFFTGLNCETSCLQQ 262
EPX (human)  VSNQIVRFPNERLTSDRGRALMFMQWGQFIDHDLDFSPESPA-RVAFTAGVDCERTCAQL 260
LPO (human)  VSNKIVGYLNEEGVLDQNRSLLFMQWGIVDHDLDFAPDTEL-GSSEYSKAQCDEYCIQG 253
TPO (human)  VTRHVIQVSNEVVTDDDRYSDLLMAWGQYIDHDIAFTPQSTS-KAAFGGGADCQMTCENQ 266
C.elegans    ISNIVH---SDAPKFHVKFTHMLMQFGQILDHDMMHSPISRGPKNTILNCSSCDSAQTLS 352
Arabidopsis  VATKLLAR-KRFIDNGDQFNVIACSWIQFMIHDWVDHLEDTHQIELEAPEEVASGCPLKS 185
              ::  :                :    :  * : **

CG6969       PECYPVDILPDDPYYKQYN----ISCMNFVRSAPAPTGR-----------FGPRMQLNQA 370
mosquito     PECFPVPLGPGDPYYTQYN----VTCMNFVRSVPAPTGH-----------FGPRQQLNQA 277
MPO (human)  PPCFPLKIPPNDPRIKNQ-----ADCIPFFRSCPACPGS----------NITIRNQINAL 333
MPO (dog)    PPCFPLKIPPNDPRIKNQ-----RDCIPFFRSSPACTDN----------NITIRNQINAL 322
MPO (mouse)  PPCFPLKIPPNDPRIKNQ-----KDCIPFFRSCPACTRN----------NITIRNQINAL 307
EPX (human)  PPCFPIKIPPNDPRIKNQ-----RDCIPFFRSAPSCPQN----------KNRVRNQINAL 305
LPO (human)  DNCFPIMFPPNDPKAGTQ-----GKCMPFFRAGFVCPTPP--------YKSLAREQINAL 300
TPO (human)  NPCFPIQLP-EEARPAAG-----TACLPFYRSSAACGTGDQGALFGNLSTANPRQQMNGL 320
C.elegans    IHCFPIKIEANDPFFPSKHSDGRPRCMPFARSLLAQVSLG-----------FRNQLNQL 400
Arabidopsis  FKFLRTKKVPTDDHHKSG-------------------------------AVNTR 208
               :                        : :                    :*

CG6969       TAFIDASVVYGNLEQRQNQLRSFINGS----LRMFVTDDGRQLLPISSNPADG---CNRV 423
mosquito     TAFIDGSVVYGSDDERMGALRTGAGGQ----LRMLRTPDGRDLLPVSTDPLDG---CNEQ 330
MPO (human)  TSFVDASMVYGSEEPLARNLRNMSNQLGLLAVNQRFQDNGRALLPFDNLHD----DPCLL 389
MPO (dog)    TSFVDASMVYGSEDPLATRLRNLTNQLGLLAVNTRFSDNGRALLPFDNLHD----DPCLL 378
MPO (mouse)  TSFVDASGVYGSEDPLARKLRNLTNQLGLLAVNTRFQDNGRALMPFDSLHD----DPCLL 363
EPX (human)  TSFVDASMVYGSEVSLSLRLRNRTNYLGLLAINQRFQDNGRALLPFDNLHD----DPCLL 361
LPO (human)  TSFLDASFVYSSEPSLASRLRNLSSPLGLMAVNQEVSDHGLPYLPYDSKKP----SPCEF 356
TPO (human)  TSFLDASTVYGSSPALERQLRNWTSAEGLLRVHARLRDSGRAYLPFVPPRAPAACAPEPG 380
C.elegans    TSFLDASTIYGSTQCEANKLRLFSDGK----LNFTDLGFNKEALPQGNQER-----DCRS 451
Arabidopsis  TPWWDGSVIYGNDETGMRRVRVFKDGK------LKISGDG------------------ 242
             *.: *.* :*..          :*       .     :        . :

CG6969       QMTRLGKYCFESGDDRANENLLLTSMHLLWARHHNYLARQLQEEQNPHWEDERLYQEARKI 483
mosquito     EMNAAGKYCFESGDARANENLHLTSMHLIWARHHNSLARGLARANPHWDDERLFQEARRI 390
MPO (human)  TNRSARIPCFLAGDTRSSEMPELTSMHTLLLREHNRLATELKSLNPRWDGERLYQEARKI 449
MPO (dog)    TNRSAGIPCFLAGDTRSSEMPELASMHTLFLREHNRLATELRRLNPRWDGERLYQEARKI 438
MPO (mouse)  TNRSAGIPCFLAGDMRSSEMPELTSMHTLFVREHNRLATQLKRLNPRWNGEKLYQEARKI 423
EPX (human)  TNRSARIPCFLAGDTRSTETPKLAAMHTLFMREHNRLATELRRLNPRWNGDKLYNEARKI 421
LPO (human)  INTTARVPCFLAGDSRASEHILLATSHTLFLREHNRLARELKRLNPQWDGEKLYQEARKI 416
TPO (human)  IPGETRGPCFLAGDGRASEVPSLTALHTLWLREHNRLAAALKALNAHWSADAVYQEARKV 440
C.elegans    VLQNRQRRCFVAGDERSNEQPGLTAIHNIFLREHNRIARYLKQINNFWSDEKLFQESRRI 511
Arabidopsis  LLERDERGVPISGDIR-NSWSGFSLLQALFVKEHNSVCDMLKERYPDFDDEKLYRTARLV 301
                 :** * ..    ::   : : :.** :. *     :. : ::..:* :

CG6969       LGAQMAHITYNEFLPVLLGKNISEAKGLLPAKHNLN-APDTYDPEVDPSIANCFA----- 537
mosquito     LAAQMQHITYAEFVPVIVGNETAGRMGLLPVSAGGEPAGDTYNATVDASIANVFA----- 445
MPO (human)  VGAMVQIITYRDYLPLVLGPTAMRKY---------LPTYRSYNDSVDPRIANVF------ 494
MPO (dog)    VGAMVQIITYRDYLPLVLGPLAMRKY---------LPRYRSYNDSVDPRISNVF------ 483
MPO (mouse)  VGAMVQIITYRDYLPLVLGPAAMKKY---------LPQYRSYNDSVDPRIANVF------ 468
EPX (human)  MGAMVQIITYRDFLPLVLGKARARRT---------LGHYRGYCSNVDPRVANVF------ 466
LPO (human)  LGAFVQIITFRDYLPILLG-DHMQKW---------IPPYQGYSESVDPRISNVF------ 460
TPO (human)  VGALHQIITLRDYIPRILGPEAFQQY---------VGPYEGYDSTANPTVSNVFS----- 486
C.elegans    NIAQLQHIIYKEWLPVVLGCQNMEKWG---LMPQTAGYFEGYDDQCDATISQEMS----- 563
Arabidopsis  TAAVIAKVHTIDWTIELLKTDTLTAG-------MRINWYGFFGKKVKDMVGARFGPLFSG 354
                *    :   ::  ::     ::         * :   . :.  :
```

FIG. 25C

```
CG6969        --------------------AAAFRFAHTLLPGLFN---ISRD-NSTPEAIELHKMLFNP 573
mosquito      --------------------GAAFRFAHTLLPGLMK---QTRNPAASASGIELHRMLFNP 482
MPO (human)   --------------------TNAFRYGHTLIQPFMFRLDNRYQPMEPNPRVPLSRVFFAS 534
MPO (dog)     --------------------TNAFRYGHTLIQPFMFRLDNRYQPMGPNPRVPLSRVFFAT 523
MPO (mouse)   --------------------TNAFRYGHTLIQPFMFRLNNQYRPTAANPRVPLSKVFFAS 508
EPX (human)   --------------------TLAFRFGHTMLQPFMFRLDSQYRASAPNSHVPLSSAFFAS 506
LPO (human)   --------------------TFAFRFGHLEVPSSMFRLDENYQPWGPEPELPLHTLFFNT 500
TPO (human)   --------------------TAAFRFGHATIHPLVRRLDASFQEHPDLPGLWLHQAFFSP 526
C.elegans     --------------------TSAFRFGHSLIRGVFTRMNDNFQNMTNHVNLTETFSNPSP 603
Arabidopsis   LVGLKKPNDHGVPYSLTEEFVSVYRMHCLLPETLILRDMNSENVDKENPAIEREIPMTEL 414
                                  .:*         .               :

CG6969        FSLWAEHGIDHALMTAAN--TPVMQVDRFFSLEVTQKLFEGTAEDRV-P--LCGLDLVSL 628
mosquito      YSLYARDGLDNALGGAIG--TALAKYDQYFSTELTERLFEKADEHLL-HGQPCGLDLVSL 539
MPO (human)   WRVVLEGGIDPILRGLMATPAKLNRQNQIAVDEIRERLFEQV-------MRIG-LDLPAL 586
MPO (dog)     WRVVLEGGIDPILRGLMATPAKLNRQNQIVVDEIRERLFEQV-------MRIG-LDLPAL 575
MPO (mouse)   WRVVLEGGIDPILRGLMATPAKLNRQNQIVVDEIRERLFEQV-------MRIG-LDLPAL 560
EPX (human)   WRIVYEGGIDPILRGLMATPAKLNRQDAMLVDELRDRLFRQV-------RRIG-LDLAAL 558
LPO (human)   WRMVKDGGIDPLVRGLLAKKSKLMKQNKMMTGELRNKLFQPT-------HRIHGFDLAAI 553
TPO (human)   WTLLRGGGLDPLIRGLLARPAKLQVQDQLMNEELTERLFVLS-------NSST-LDLASI 578
C.elegans     VYDKNSGHMESILMGLIG--ANSMAFDRHIVTAVRNHLFAKPG------GPLTGLDLPAV 655
Arabidopsis   IGKKAGEKASKLGFEQLLVSMGHQSCGALTLWNYPNWMRNLVAQDIDGEDRPHLIDMAAL 474
                                   .              : :             :*: ::

CG6969        NIQRGRDHGIPSYPVFRRHCRLPTVDTWEEMSQAIDN-ATLDSIRQIYESPQDVDVYTGA 687
mosquito      NIQRGRDHGLPAYPRWRKHCHLTPADSWEELERIVDP-ESYRQMRRIYREPANVDVYSGA 598
MPO (human)   NMQRSRDHGLPGYNAWRRFCGLPQPETVGQLGTVLRNLKLARKLMEQYGTPNNIDIWMGG 646
MPO (dog)     NMQRSRDHGLPGYNAWRRFCGLPQPSTVGELATVLRNLDLAQKLMQQYGTPDNIDIWMGG 635
MPO (mouse)   NMQRSRDHGLPGYNAWRRFCGLPQPSTVGELGTVLKNLELARKLMAQYGTPNNIDIWMGG 620
EPX (human)   NMQRSRDHGLPGYNAWRRFCGLSQPRNLAQLSRVLKNQDLARKFLNLYGTPDNIDIWIGA 618
LPO (human)   NTQRCRDHGQPGYNSWRAFCDLSQPQTLEELNTVLKSKMLAKKLLGLYGTPDNIDIWIGA 613
TPO (human)   NLQRGRDHGLPGYNEWREFCGLPRLETPADLSTAIASRSVADKILDLYKHPDNIDVWLGG 638
C.elegans     NIQRGRDHGVQGYNAYRKHCGLRKASAFSDLRDVMNS-EAVTALETAYAHVDDIDLFPGI 714
Arabidopsis   EIYRDRERGVPRYNEFRKNLLMSPISKWEELTDDEEAIKVLREVYEDD--IEKLDLNVGL 532
              : *  *::*     *  :*     :         ::                .:*:  *

CG6969        LSEPPLDGAIFGPLLSCMVSDQFLRLKLGDSHWYERKMGPQKFTKAQLAEIYKTSLAAII 747
mosquito      LSEAPVRDGIVGPLLTCLIGDQFLRLKQGDSFWYERRRGPQRFTEAQLQQIYNTKLSSII 658
MPO (human)   VSEPLKRKGRVGPLLACIIGTQFRKLRDGDRFWWEN---EGVFSMQQRQALAQISLPRII 703
MPO (dog)     VAEPLPERGRVGQLLACLIGTQFRKLRDGDRFWWEN---RGVFSSQQQQALARISLPRLI 692
MPO (mouse)   VSEPLEPNGRVGQLLACLIGTQFRKLRDGDRFWWEN---RGVFSKQQRQALASISLPRLI 677
EPX (human)   IAEPLLPGARVGPLLACLFENQFRRARDGDRFWWQK---RGVFTKRQRKALSRISLSRII 675
LPO (human)   IAEPLVERGRVGPLLACLLGKQFQQIRDGDRFWWEN---PGVFTNEQKDSLQKMSFSRLV 670
TPO (human)   LAENFLPRARTGPLFACLIGKQMKALRDGDWFWWEN---SHVFTDAQRRELEKHSLSRVI 695
C.elegans     MSESPTRGSLVGPTLACLIGEQMQRLKKCDRFYYETSDSMVRFTPDQLVEIRKASLSRII 774
Arabidopsis   HAEKKIKGFAISETAFFIFLLVASRRLEADRFFTTNFNEKTYTKEGLEWVNTTETLKDVI 592
               :*    .    :.    * .:      .     .          .:   ::

CG6969        CRNSDGITRVREHVMQRLRDGGNPHVDCQDLEGFHFNFEPWSEKQ-QPQDLHSAGISRGS 806
mosquito      CRNSDHIEQSPVYLMKRTDSRTNPETDCKQLD--TFDFEPFREDAEQPQ----------- 705
MPO (human)   CDNTG-ITTVSKNNIFMSNSYPRDFVNCSTLP--ALNLASWREAS--------------- 745
MPO (dog)     CDNTG-ITTVSKNNIFMSNMFPRDFVNCSTLP--ALDLTSWRDSN--------------- 734
MPO (mouse)   CDNTG-ITTVSKNNIFMSNTYPRDFVSCNTLP--KLNLTSWKET---------------- 718
EPX (human)   CDNTG-ITTVSR-DIFRANIYPRGFVNCSRIP--RLNLSAWRGT---------------- 715
LPO (human)   CDNTR-ITKVPR-DPFWANSYPYDFVDCSAID--KLDLSPWASVKN-------------- 712
TPO (human)   CDNTG-LTRVPM-DAFQVGKFPEDFESCDSIT--GMNLEAWRETFPQDDKCGFPESVENG 751
C.elegans     CDNSEYAANIQPNVFLMPDDLTNSPMTCSELS--EIDLNKWVERDYCLVDERVVNRGKTK 832
Arabidopsis   DRHFPRLTDQWMRCSSAFSVWGSDPNPKNWVP---LYLRSAP------------------ 631
                :                      * .:        .:  : :    :
```

FIG. 25D

```
CG6969        TSVRVMSKANHQAHNVTLHIDKGI------------------------------ 830
mosquito      ------------------------------------------------------
MPO (human)   ------------------------------------------------------
MPO (dog)     ------------------------------------------------------
MPO (mouse)   ------------------------------------------------------
EPX (human)   ------------------------------------------------------
LPO (human)   ------------------------------------------------------
TPO (human)   DFVHCEESGRRVLVYSCRHGYELQGREQLTCTQEGWDFQPPLCKDVNEC----- 800
C.elegans     RITPCITCTCTLEGPECHSITIDDCSRLLRDYSITDIQKDPVCLIQCSQQLKKL 886
Arabidopsis   ------------------------------------------------------
```

SEQUENCE LISTING

<160> NUMBER OF SEQ ID NOS: 18

<210> SEQ ID NO 1
<211> LENGTH: 3406
<212> TYPE: DNA
<213> ORGANISM: Drosophila melanogaster

<400> SEQUENCE: 1

```
actaaggtat ggcagcgccg taagttcctc tgcaaagaaa aataaaaact aatgaataaa    60
atgaagcaga aataaagtgc aataatcttc cgacaacaga aggttacaag tgcaatacac   120
aatggctgca aaggagacga tgattgtgtt tgtctacgac acagagtgtc tcacagacga   180
ggcggatgat cccatatcgg cggtgctcta cttccatcca agctgggtgt ccgactccca   240
gaaggtggct ctgtgtggtc agcttatggg cacgtcgtat ttcctcaagg attgcttctt   300
taatccccgc atcctggcgc tgcagaatgg aaaatttgtg ctgaaggaat tcggtcgttt   360
tattctggca attggcactg atcgaaatat tggagatcaa ctgttggaac atcgtgctga   420
tctgctgagt tccctgctca agttttttcca ccgtgacgtc cagacattgt atgcccagta   480
tgctgcaccg cccgccctga accgccggaa tctcagcgag aaactgtacc acatctttga   540
aacatatctg ccgatgctgc agcgcaacgg aaatacattt caaaatgtgc cgaggctgcg   600
aatgccaaag acggccagtc atatattcct ggaggctata caaacgttgc aaagttgcca   660
gcagacaaag ggaatacttg gcggagcgat tctgtaccac aacaaggtgg ttgcctcgca   720
actgagcgat atggtgacca agcatcttgt actcaccgat cctctgcaca tccgcactgc   780
ggccgagcaa gtgaccaacc atcctgagtt ccacataccc aacggcgttc agatgctggt   840
ggtttatttg gagcatatgc agtaccgcca gttagctggc gaggcacagc gcgcccagaa   900
cctgcagatg aacacagctc agctcaccca aaatggtatg ccgtttcagt atgccaagcg   960
taagataaag cgggacaagt cgctcatttt tacccatata cccgaggagg agcacgcccc  1020
ggagcagcag ggagcagttg aacagctacc accagccagg cccaaatcta tgcgacccac  1080
ccacctgccg ttgcgtataa aaagcatgca gagcaaagag ctaccggagt ctggcattgc  1140
atcaataaat ttcgacgaaa ccgattccta tccgcagttc attggacgaa ccagcgtttg  1200
caatactcca atgaccgaga caaggtact gccggtggcc aatgttatgt ccatttgcgc  1260
aaatcccgaa gatgagggca agaggagga tattcacaat tccaatggca agacacattc  1320
gcgtcgaaat tctctaaaag tggatgtgga gaaattcttc caaaacttca ttagcaatcc  1380
aaacaaacag ctcacacgac gcaaatcatc tgcagacctg caggatgcac ttcgcgccat  1440
ctccaagaaa ctgaataatt ttacgcatgg cctcaaaacc gatgtgaatc gaaatggaag  1500
cggtaatggt gatgtctctt cggattcgcc agatttcata gaggacgatg ataagattac  1560
ttcgcggacc atcagcgatc ccacctatcc ggtattcaac actaacggcc agcagatctc  1620
gcgcagtttg tttcagcaat ttctggatca gtatcgtaaa ttgtggggtg ttgctagtga  1680
gcaggcgcac gaggatgccg agctagccgc tctggtagcc gagttccagg agttcaacgc  1740
cgagatccaa aagctcgacg agcacatgag acagcaagca gcggaagcat cgtctgccga  1800
taggaatctc aacgtttccg cagccaaaac tccgctggac aagcgatcca tgacgctgcc  1860
attgaaatca gcaggagaat ctactttcgg agagcgtgcg tccggacgca gtggagctgg  1920
tggagtacca ctaacacccc tgatggccaa actatctgtt ctggctctaa gcgaaacaac  1980
gcccatcgag atacaaactc cgctgacaac cagtaaggtt ttcccacggc gaagttcact  2040
gaagtgcgag gatgcagtgg atgcattggc tgccttgacc acagcccctg ctcaacctcc  2100
gggtccaatt caaccagatg gcttgcaaag aactgaactc tatatatgcg acagcagaa   2160 tatgacctta ttattgctca tggaggaggg tacttgtcaa caacagcagg ttgtgcagaa   2220
gatgttcgac atttgtgtgg ccaagttccc gcacatggaa tctcaactga atcaaacctt   2280
aaatgtaaat gtggagggcg acaatcgcga cgggagcaac tatagcttca tgtgcgtgga   2340
ctccaagtgg gatgttctgc agcggaatgg cccttggaat cccctagagc ttaatatcct   2400
```

```
cgagagcatg cactcgatac attccagtgg tcatcatctt acagatttga tcttgagatc    2460
caacgactcc gtttattatg gccataagaa tggaaggacc gagttcttct acaaggaacc    2520
tacccatcag atcaatggca taccaccgcc ctcggatccg attggcaata caatcccg      2580 cgccaagtcg cgactggaac gtgatcattc ctacatgctg ttctaggctg tgcaatggat    2640
cgtatattat aaacatattt aaatactcgc atgcttagcc aaaaacagat aatgtaatcg    2700
gggacaccag atagtctggg tccccgaaga atagccaact taatgccatc cactgttatt    2760
tcatttgcga tctctggctg attccttcgt gagtcttttc ttttgtatag tggttagata    2820
atgattccat atcatataca atgcaaacca agggaactca atttaaacg atctaaattt     2880 tacttcgact tttatacaac aaatttataa gaaacattgc cgaccttttt taccgccatt    2940
caatggactc acgaaggaaa ccaaaagaat tttagatatg ccgcttacag ccagcgaaat    3000
attaagcctt gtttgaattt tcacttgatt gatgtaaagt acaaaaatgt tttaagcttt    3060
gtttacaatg tccagcactg ttgtttaatt tataagcttg tatcctatac aattatttta    3120 atcatttgc atttgctttg accgaaaaga tgcgacattt tgcactgatt tcgagagcca     3180
aagaatttaa atcaaggttt ttaattgtaa atatacatta tacaaaatta gattcattta    3240
aatggaataa tgtgtaacta acctaaaatt cacacagatt ccgttctgtc cagttgcaaa    3300
cataaaccta tcttagctgt ttctcattat caaagattaa gcgctttgtg ccaatttaaa    3360
tgcaggataa atgcttaaaa taaaccgtca aatatgtagg aacgtg                   3406

<210> SEQ ID NO 2
<211> LENGTH: 3473
<212> TYPE: DNA
<213> ORGANISM: Drosophila melanogaster

<400> SEQUENCE: 2
cgctattggc ttgttgactt atcagaatcg tcggtcgtta aatgtgataa ggagccacga     60
tgcagcgcta gacttggaag caccgaaatc cactagattt caggagcaat gtttcgggat   120
tggcgcaaaa ccaagcacaa gcgatggcag aaggtgcagc agaagcagca gacctcaatc   180
ctcaccgaaa gggagacgat gattgtgttt gtctacgaca cagagtgtct cacagacgag   240
gcggatgatc ccatatcggc ggtgctctac ttccatccaa gctgggtgtc cgactcccag   300
aaggtggctc tgtgtggtca gcttatgggc acgtcgtatt tcctcaagga ttgcttcttt   360
aatccccgca tcctggcgct gcagaatgga aaatttgtgc tgaaggaatt cggtcgtttt   420
attctggcaa ttggcactga tcgaaatatt ggagatcaac tgttggaaca tcgtgctgat   480
ctgctgagtt ccctgctcaa gttttttccac cgtgacgtcc agacattgta tgcccagtat   540
gctgcaccgc ccgccctgaa ccgccggaat ctcagcgaga aactgtacca catctttgaa   600
acatatctgc cgatgctgca gcgcaacgga atacatttc aaaatgtgcc gaggctgcga    660
atgccaaaga cggccagtca tatattcctg gaggctatac aaacgttgca agttgccag     720 cagacaaagg gaatacttgg cggagcgatt ctgtaccaca caaggtggt tgcctcgcaa     780 ctgagcgata tggtgaccaa gcatcttgta ctcaccgatc ctctgcacat ccgcactgcg   840
gccgagcaag tgaccaacca tcctgagttc cacatacccca acggcgttca gatgctggtg   900
gtttatttgg agcatatgca gtaccgccag ttagctggcg aggcacagcg cgcccagaac   960
ctgcagatga acacagctca gctcacccaa aatggtatgc cgtttcagta tgccaagcgt  1020
aagataaagc gggacaagtc gctcattttt acccatatac ccgaggagga gcacgccccg  1080
gagcagcagg gagcagttga acagctacca ccagccaggc ccaaatctat gcgacccacc  1140
```

```
cacctgccgt tgcgtataaa aagcatgcag agcaaagagc taccggagtc tggcattgca    1200
tcaataaatt tcgacgaaac cgattcctat ccgcagttca ttggacgaac cagcgtttgc    1260
aatactccaa tgaccgagaa caaggtactg ccggtggcca atgttatgtc catttgcgca    1320
aatcccgaag atgagggcaa agaggaggat attcacaatt ccaatggcaa gacacattcg    1380
cgtcgaaatt ctctaaaagt ggatgtggag aaattctttc aaaacttcat tagcaatcca    1440
aacaaacagc tcacacgacg caaatcatct gcagacctgc aggatgcact tcgcgccatc    1500
tccaagaaac tgaataattt tacgcatggc ctcaaaaccg atgtgaatcg aaatggaagc    1560
ggtaatggtg atgtctcttc ggattcgcca gatttcatag gaacgatga taagattact    1620 tcgcggacca tcagcgatcc cacctatccg gtattcaaca ctaacggcca gcagatctcg    1680
cgcagtttgt ttcagcaatt tctggatcag tatcgtaaat tgtggggtgt tgctagtgag    1740
caggcgcacg aggatgccga gctagccgct ctggtagccg agttccagga gttcaacgcc    1800
gagatccaaa agctcgacga gcacatgaga cagcaagcag cggaagcatc gtctgccgat    1860
aggaatctca acgtttccgc agccaaaact ccgctggaca agcgatccat gacgctgcca    1920
ttgaaatcag caggagaatc tactttcgga gagcgtgcgt ccggacgcag tggagctggt    1980
ggagtaccac taacacccct gatggccaaa ctatctgttc tggctctaag cgaaacaacg    2040
cccatcgaga tacaaactcc gctgacaacc agtaaggttt cccacggcg aagttcactg    2100 aagtgcgagg atgcagtgga tgcattggct gccttgacca cagccctgc tcaacctccg    2160 ggtccaattc aaccagatgg cttgcaaaga actgaactct atatatgcgg acagcagaat    2220
atgaccttat tattgctcat ggaggagggt acttgtcaac aacagcaggt tgtgcagaag    2280
atgttcgaca tttgtgtggc caagttcccg cacatggaat ctcaactgaa tcaaaccttaa   2340 aatgtaaatg tggagggcga caatcgcgac gggagcaact atagcttcat gtgcgtggac    2400
tccaagtggg atgttctgca gcggaatggc ccttggaatc ccctagagct taatatcctc    2460
gagagcatgc actcgataca ttccagtggt catcatctta cagatttgat cttgagatcc    2520
aacgactccg tttattatgg ccataagaat ggaaggaccg agttcttcta caaggaacct    2580
acccatcaga tcaatggcat accaccgccc tcggatccga ttggcaatat acaatcccgc    2640
gccaagtcgc gactggaacg tgatcattcc tacatgctgt tctaggctgt gcaatggatc    2700
gtatattata aacatattta aatactcgca tgcttagcca aaaacagata atgtaatcgg    2760
ggacaccaga tagtctgggt ccccgaagaa tagccaactt aatgccatcc actgttattt    2820
catttgcgat ctctggctga ttccttcgtg agtctttct tttgtatagt ggttagataa    2880
tgattccata tcatatacaa tgcaaaccaa gggaactcaa ttttaaacga tctaaatttt    2940
acttcgactt ttatacaaca aatttataag aaacattgcc gacctttttt accgccattc    3000
aatggactca cgaaggaaac caaagaatt ttagatatgc cgcttacagc cagcgaaata    3060
ttaagccttg tttgaatttt cacttgattg atgtaaagta caaaaatgtt ttaagctttg    3120
tttacaatgt ccagcactgt tgtttaattt ataagcttgt atcctataca attattttaa    3180
tcattttgca tttgctttga ccgaaagat gcgacatttt gcactgattt cgagagccaa    3240
agaatttaaa tcaaggtttt taattgtaaa tatacattat acaaaattag attcatttaa    3300
atggaataat gtgtaactaa cctaaaattc acacagattc cgttctgtcc agttgcaaac    3360
ataaacctat cttagctgtt tctcattatc aaagattaag cgctttgtgc caatttaaat    3420
gcaggataaa tgcttaaaat aaaccgtcaa atatgtagga acgtgagaac gaa           3473
```

<210> SEQ ID NO 3

<211> LENGTH: 2059
<212> TYPE: DNA
<213> ORGANISM: Drosophila melanogaster

<400> SEQUENCE: 3

| | | | | | |
|---|---|---|---|---|---|
| ttacccagca | ccagtgacac | tggtgaaagt | tttgttgtgt | atttggtgtt | ttgccaatgc | 60 |
| tgataagaaa | atgaacggac | tgattgtgtt | taacagcgcc | aacgatgttg | tataccagaa | 120 |
| gcttaacgag | ccgctggcgc | agaagatccg | gagtgtggcc | accacccagg | gcctgctcca | 180 |
| gtccggcggc | tccctggaca | gcaacatact | gctgcagatt | ttcagcccca | tcgttggatc | 240 |
| tcagcgaata | atgcagtgcc | agttcgataa | tgcctactcc | agcctgcagt | gtgagcaagg | 300 |
| cttcaatttg | gtgttcggcg | aacttcttgg | cttcaccttt | ctgaagatcg | gacaaatacc | 360 |
| cgtggagctg | ctgggtcgcc | aaatgggtgt | ggccattacg | ctgacgcgct | attgttacgg | 420 |
| cgccaatttg | tttgccgccc | aggcgggggc | catgcaacag | gagttgctga | cgcagtgcct | 480 |
| cgactgctat | gagactttgt | tgtgggagga | ggatcagacg | tacctgctgg | aggccatgcc | 540 |
| caggctgctg | atcaacacgg | aactaaagag | gacagtgcat | ctgacgctgg | acgccacgct | 600 |
| tgagcacttg | cgccagctcg | gactgccccg | agcccacgcc | ctgttgctcg | tttccaacaa | 660 |
| gctggtggcc | gcgaacagca | ctcggcaagc | tctgccgctt | gctgccgccg | acctactctt | 720 |
| cctcagcctc | atgtcacgcg | ccctgcaagc | gccaaagtcc | ccttcccagc | gagcagtagc | 780 |
| tgtattcctg | cagggtgtct | cctatgatgt | gaactctggc | tgcgttccca | gtatcgtgca | 840 |
| catctcgcgt | ctccatggta | accaagttct | cctgcaggtc | atcgagtacg | cccacatgcc | 900 |
| actgaccagc | tgcatctacg | attccttctt | tgtgcttcaa | aaaatcgtgg | ctgttcagca | 960 |
| tcagggcgat | tcggatgccc | tgaagcccgc | cttcgagaac | ctcgaatcgt | ttattgtgca | 1020 |
| ggccttgacc | gctttgaagc | gatatctgaa | acagcgatcg | gaaaccgatg | acctagaaa | 1080 |
| ctgcacgaag | aagttcgccg | ctaaatggga | gaatcttcgc | aagatgtaca | ctgagtactt | 1140 |
| caagaacttt | gagcgggagc | tgctcgtgag | gattgagtcg | aatttgccct | cgttcggaga | 1200 |
| ggaactgaag | cagatattca | cactggcctg | ctgcgacagc | tcaagtgtcc | atgagctgga | 1260 |
| tcaactctct | gatacggcag | cgaatgtgga | agccaagcta | ctggagttcg | ctgaatttct | 1320 |
| ggccgttaag | gccactcgta | acatatccat | tgatgcttat | ttggaggatt | ttccgggtct | 1380 |
| ggtgcacttt | atgtacgtca | atcgcagccg | aggacaaatg | cttgctccgg | atctgcgacc | 1440 |
| gaaccagctg | gtgccaaaga | caaaactctg | gagcatggtg | gagatcgcga | gaaattacct | 1500 |
| taagaagggc | cagaccacag | tgatgtgaa | ggataaggca | ttccattact | cgtacttcct | 1560 |
| ctggttcgag | gacatgtctg | gtggcgttct | tagtaccgtc | gtggatttgc | agcaccactt | 1620 |
| tctgtccaca | ggagcagcca | gtggcaacgg | ttcgaaatcc | ccaacagaac | caggtgctct | 1680 |
| tacaatggac | tattaccacg | atctggcgga | gttgtgcttc | cccaagctgt | caccggccaa | 1740 |
| agtgcgcgtc | tacgagttgt | attgcattca | tctgggactg | gtaaccgcca | catgcgccgt | 1800 |
| ggagcatgca | cgtcgcctgg | tggccaccat | cagtgatgtt | gtgggcgagg | aagcgtttta | 1860 |
| agtgcattgg | ccattggtca | ttccagattt | ataacgatgat | ttctagtcaa | ttttcgagac | 1920 |
| tcctaggcga | gataatccac | tcgaaatttt | gttaggttta | ggacaactat | catccactgt | 1980 |
| tataggctac | acaacaagga | tatttgtaaa | gttattggaa | acatatatat | tttcttcaac | 2040 |
| cggcaataaa | aatgtaaca | | | | | 2059 |

<210> SEQ ID NO 4
<211> LENGTH: 2103
<212> TYPE: DNA

<213> ORGANISM: Homo sapiens

<400> SEQUENCE: 4

```
atgaagtgcg tcttggtggc cactgagggc gcagaggtcc tcttctactg gacagatcag      60
gagtttgaag agagtctccg gctgaagttc gggcagtcag agaatgagga agaagagctc     120
cctgccctgg aggaccagct cagcaccctc ctagccccgg tcatcatctc ctccatgacg     180
atgctggaga agctctcgga cacctacacc tgcttctcca cggaaaatgg caacttcctg     240
tatgtccttc acctgtttgg agaatgcctg ttcattgcca tcaatggtga ccacaccgag     300
agcgaggggg acctgcggcg gaagctgtat gtgctcaagt acctgtttga agtgcacttt     360
gggctggtga ctgtggacgg tcatcttatc cgaaaggagc tgcggccccc agacctggcg     420
cagcgtgtcc agctgtggga gcacttccag agcctgctgt ggacctacag ccgcctgcgg     480
gagcaggagc agtgcttcgc cgtggaggcc ctggagcgac tgattcaccc ccagctctgt     540
gagctgtgca tagaggcgct ggagcggcac gtcatccagg ctgtcaacac cagccccgag     600
cggggaggcg aggaggccct gcatgccttc ctgctcgtgc actccaagct gctggcattc     660
tactctagcc acagtgccag ctccctgcgc cggccgacca tgcttgccct catcctcctg     720
gttcaggacc tctaccccag cgagagcaca gcagaggacg acattcagcc ttccccgcgg     780
agggcccgga gcagccagaa catccccgtg cagcaggcct ggagccctca ctccacgggc     840
ccaactgggg ggagctctgc agagacggag acagacagct ctccctccc tgaggagtac     900
ttcacaccag ctccttcccc tggcgatcag agctcaggta gcaccatctg gctggagggg     960
ggcaccccc ccatggatgc ccttcagata gcagaggaca ccctccaaac actggttccc    1020
cactgccctg tgccttccgg ccccagaagg atcttcctgg atgccaacgt gaaggaaagc    1080
tactgccccc tagtgcccca ccatgtac tgcctgcccc tgtggcaggg catcaacctg    1140
gtgctcctga ccaggagccc cagcgcgccc ctggccctgg ttctgtccca gctgatggat    1200
ggcttctcca tgctggagaa aagctgaag gaagggccgg agcccggggc ctccctgcgc    1260
tcccagcccc tcgtgggaga cctgcgccag aggatgggaca agtttgtcaa gaatcgaggg    1320
gcacaggaga ttcagagcac ctggctggag tttaaggcca aggcttctc caaaagtgag    1380
cccggatcct cctgggagct gctccaggca tgtgggaagc tgaagcggca gctctgcgcc    1440
atctaccggc tgaactttct gaccacagcc cccagcaggg aggcccaca cctgccccag    1500
cacctgcagg accaagtgca gaggctcatg cgggagaagc tgacggactg gaaggacttc    1560
ttgctggtga agagcaggag gaacatcacc atggtgtcct acctagaaga cttcccaggc    1620
ttggtgcact tcatctatgt ggaccgcacc actgggcaga tggtggcgcc ttccctcaac    1680
tgcagtcaaa agacctcgtc ggagttgggc aaggggccgc tggctgcctt tgtcaaaact    1740
aaggtctggt ctctgatcca gctggcgcgc agatacctgc agaagggcta caccacgctg    1800
ctgttccagg aggggattt ctactgctcc tacttcctgt ggttcgagaa tgacatgggg    1860
tacaaactcc agatgatcga ggtgcccgtc ctctccgacg actcagtgcc tatcggcatg    1920
ctgggaggag actactacag gaagctcctg cgctactaca gcaagaaccg cccaaccgag    1980
gctgtcaggt gctacgagct gctggccctg cacctgtctg tcatccccac tgacctgctg    2040
gtgcagcagg ccggccagct ggcccggcgc ctctgggagg cctcccgtat ccccctgctc    2100
tag                                                                   2103
```

<210> SEQ ID NO 5
<211> LENGTH: 2127
<212> TYPE: DNA

<213> ORGANISM: Homo sapiens

<400> SEQUENCE: 5

```
atggccacct ctacctccac agaggcaaag tcagcctcgt ggtggaatta ttttttttctt      60
tatgatggtt ccaaggtaaa ggaagaaggc gatccaacaa gagctggcat tgttactttt     120
tatccttccc agaccctgct agaccaacag gagttgcttt gtggacagat tgctggagtt     180
gtccgctgtg tttctgacat ttctgactct cctcctactc ttgttcgtct gagaaaactg     240
aagtttgcca taaaagttga tggagattac ctttgggtgc tgggctgtgc tgtggagctc     300
cctgatgtca gctgcaagcg gtttctggat cagctagttg gattctttaa tttttacaat     360
ggacctgttt ccctagctta tgagaactgt tctcaggaag aactgagcac ggagtgggac     420
accttcatcg agcaaattct gaaaaacacc agtgatctgc ataagatttt caattccctc     480
tggaacttgg accaaactaa agtggagccc ctgttgttgc tgaaggcagc ccgcattctg     540
cagacctgcc agcgctcgcc tcacattctc gctggctgca tcctctataa aggactgatt     600
gtcagcaccc aactcccgcc ctccctcacc gccaaggtcc tgcttcaccg aacagcacct     660
caggagcaga gactccctac gggagaggat gccccgcagg aacatggagc ggcattgccc     720
ccgaatgtcc agattatccc tgttttttgtg accaaagagg aagccattag tctccacgag     780
ttcccggtgg aacagatgac aaggtctcta gcatctccag caggactcca ggatggttca     840
gcccagcacc atccaaaggg tgggagcaca tctgccctga agaaaacgc cactggccat     900
gtggaatcca tggcctggac cacccccagat cccacatccc ctgacgaagc ttgtccagat     960
ggcaggaagg agaacggatg cttgtctggc catgatctgg agagcatcag gcccgcagga    1020
ctgcacaact ctgccagggg tgaggttctt ggcctcagct cctccctggg gaaggaacta    1080
gtctttctcc aagaagaact cgacttgtct gaaatccaca ttccagaggc tcaggaagtg    1140
gaaatggcct caggtcattt tgccttccta catgtgcctg ttccagatgg cagggctcct    1200
tactgcaagg catctctcag cgcctccagc agcctggaac ccacgcctcc tgaggacaca    1260
gccatcagca gcttgcgccc tccctctgct cctgagatgc tgacccagca tggagcccaa    1320
gagcagctcg aagaccatcc tggccatagc agccaagccc ccattcccag agcagaccct    1380
ctccccagaa ggacccgcag gcccttgtta ttgcctcgct tagatccagg acagagagga    1440
aacaagcttc ccacggggga acaaggcctg gatgaggatg ttgatggggt ctgtgaaagc    1500
cacgcagccc ctggtctgga atgcagttca ggctcagcaa actgtcaggg tgctggcccc    1560
tctgcagatg gaatcagctc caggctgaca ccagcagagt cctgcatggg gctcgtgagg    1620
atgaatctct acactcactg cgtcaaaggg ctggtgctgt ccctgctggc tgaggagccg    1680
ctgctgggag acagcgcagc catagaggaa gtgtaccaca gcagcctggc ttcactgaat    1740
gggctggaag tccacctgaa agagacgctg cccagggatg aggcagcctc cacgagcagc    1800
acctacaact tcacacatta cgaccgcatt cagagcttgc tgatggcaaa cctgccgcag    1860
gtggccaccc cgcaggatcg ccgcttcctc caggccgtca gcctgatgca tagcgaattt    1920
gcccagctgc ccgcgcttta tgaaatgact gtcagaaatg cctccacggc tgtgtacgcc    1980
tgttgcaacc ccatccagga gacatatttc cagcagctgg cacctgcagc acggagctcc    2040
ggcttcccaa accctcagga tggcgccttc agcctctccg gcaaagcaaa gcagaagctg    2100
ctgaagcacg gggtgaactt gctctctga                                       2127
```

<210> SEQ ID NO 6
<211> LENGTH: 830
<212> TYPE: PRT

<213> ORGANISM: Drosophila melanogaster

<400> SEQUENCE: 6

```
Met Thr Asp Glu Thr Thr Pro Leu Thr Asp Ala Val Pro Ser Gly Ser
1               5                   10                  15

Gly Tyr Val Val Leu Pro Pro Tyr Gln Gly Pro Glu Arg Val Phe Pro
            20                  25                  30

Gly Gly Val Ser Pro Arg Ala Arg Arg Asn Lys Met Arg Gln Phe Gln
        35                  40                  45

Cys Cys Met Gly Ile Thr Phe Ile Ala Ile Val Phe Thr Ala Leu Cys
    50                  55                  60

Leu Ala Leu Val Phe Ser Asp Ser Leu Gly Gly Ala Asp Gly Gly Pro
65                  70                  75                  80

Ser Phe Phe Phe Val Val Asn Gly Ser Asp Ser Glu Leu Ala Pro Asn
                85                  90                  95

Arg Pro Leu Pro Asp Glu Pro Ala Ala Glu Trp Ala Leu Gln Gln Ala
            100                 105                 110

Ala Leu Gly His His Asp Gly Ala Gln Ala Val Ser Ala Gly Ile Lys
        115                 120                 125

Ala Leu Gly Asp Arg Glu Ile Leu Glu Glu Gly Leu Gln Pro Asn Glu
130                 135                 140

Val Asn Thr Pro Ser Phe Arg His Tyr Arg Ser Leu Ser Thr Asn Pro
145                 150                 155                 160

Glu Ala Arg Lys Leu Ala Arg Arg Gly Tyr Val Glu Asn Gln Ala Thr
                165                 170                 175

Ile Asp Ile Ala Lys Arg Phe Asn Tyr Thr Lys Gln Pro Gly Arg Ser
            180                 185                 190

Asn Ile Gly Trp Gly Pro Lys Ile Val Leu Pro Asp Pro Thr Val Leu
        195                 200                 205

Arg Leu Glu Cys Asp Phe Asn Ala Arg Tyr Arg Arg Ser Thr Gly Val
210                 215                 220

Cys Asn Asn Lys Gln His Pro Arg Thr Tyr Gly Ala Ser Met Val Pro
225                 230                 235                 240

Tyr Arg Arg Met Val Ser Pro Asp Tyr Ala Asp Gly Ile Ala Ala Pro
                245                 250                 255

Arg Val Ser His His Gly Arg Leu Pro Pro Ala Arg Gln Val Ser Leu
            260                 265                 270

Lys Ile His Arg Ser Ser Tyr Glu Thr Asp Ser Asn Phe Thr Val Met
        275                 280                 285

Leu Ala Val Phe Gly Gln Phe Met Asp His Asp Ile Thr Ala Thr Ser
290                 295                 300

Leu Thr Thr Ser Gln Glu Gly Ser Ile Asp Cys Cys Val Ala Ala
305                 310                 315                 320

Thr Arg Glu Gln His Pro Glu Cys Tyr Pro Val Asp Ile Leu Pro Asp
                325                 330                 335

Asp Pro Tyr Tyr Lys Gln Tyr Asn Ile Ser Cys Met Asn Phe Val Arg
            340                 345                 350

Ser Ala Pro Ala Pro Thr Gly Arg Phe Gly Pro Arg Met Gln Leu Asn
        355                 360                 365

Gln Ala Thr Ala Phe Ile Asp Ala Ser Val Val Tyr Gly Asn Leu Glu
370                 375                 380

Gln Arg Gln Asn Gln Leu Arg Ser Phe Ile Asn Gly Ser Leu Arg Met
385                 390                 395                 400

Phe Val Thr Asp Asp Gly Arg Gln Leu Leu Pro Ile Ser Ser Asn Pro
```

```
                    405                 410                 415
Ala Asp Gly Cys Asn Arg Val Gln Met Thr Arg Leu Gly Lys Tyr Cys
            420                 425                 430

Phe Glu Ser Gly Asp Asp Arg Ala Asn Glu Asn Leu Leu Leu Thr Ser
            435                 440                 445

Met His Leu Leu Trp Ala Arg His His Asn Tyr Leu Ala Arg Gln Leu
450                 455                 460

Gln Glu Gln Asn Pro His Trp Glu Asp Glu Arg Leu Tyr Gln Glu Ala
465                 470                 475                 480

Arg Lys Ile Leu Gly Ala Gln Met Ala His Ile Thr Tyr Asn Glu Phe
            485                 490                 495

Leu Pro Val Leu Leu Gly Lys Asn Ile Ser Glu Ala Lys Gly Leu Leu
            500                 505                 510

Pro Ala Lys His Asn Leu Asn Ala Pro Asp Thr Tyr Asp Pro Glu Val
            515                 520                 525

Asp Pro Ser Ile Ala Asn Cys Phe Ala Ala Ala Phe Arg Phe Ala
530                 535                 540

His Thr Leu Leu Pro Gly Leu Phe Asn Ile Ser Arg Asp Asn Ser Thr
545                 550                 555                 560

Pro Glu Ala Ile Glu Leu His Lys Met Leu Phe Asn Pro Phe Ser Leu
            565                 570                 575

Trp Ala Glu His Gly Ile Asp His Ala Leu Met Thr Ala Ala Asn Thr
            580                 585                 590

Pro Val Met Gln Val Asp Arg Phe Phe Ser Leu Glu Val Thr Gln Lys
            595                 600                 605

Leu Phe Glu Gly Thr Ala Glu Asp Arg Val Pro Leu Cys Gly Leu Asp
610                 615                 620

Leu Val Ser Leu Asn Ile Gln Arg Gly Arg Asp His Gly Ile Pro Ser
625                 630                 635                 640

Tyr Pro Val Phe Arg Arg His Cys Arg Leu Pro Thr Val Asp Thr Trp
            645                 650                 655

Glu Glu Met Ser Gln Ala Ile Asp Asn Ala Thr Leu Asp Ser Ile Arg
            660                 665                 670

Gln Ile Tyr Glu Ser Pro Gln Asp Val Asp Val Tyr Thr Gly Ala Leu
            675                 680                 685

Ser Glu Pro Pro Leu Asp Gly Ala Ile Phe Gly Pro Leu Leu Ser Cys
            690                 695                 700

Met Val Ser Asp Gln Phe Leu Arg Leu Lys Leu Gly Asp Ser His Trp
705                 710                 715                 720

Tyr Glu Arg Lys Met Gly Pro Gln Lys Phe Thr Lys Ala Gln Leu Ala
            725                 730                 735

Glu Ile Tyr Lys Thr Ser Leu Ala Ala Ile Ile Cys Arg Asn Ser Asp
            740                 745                 750

Gly Ile Thr Arg Val Arg Glu His Val Met Gln Arg Leu Arg Asp Gly
            755                 760                 765

Gly Asn Pro His Val Asp Cys Gln Asp Leu Glu Gly Phe His Phe Asn
770                 775                 780

Phe Glu Pro Trp Ser Glu Lys Gln Gln Pro Gln Asp Leu His Ser Ala
785                 790                 795                 800

Gly Ile Ser Arg Gly Ser Ser Val Arg Val Met Ser Lys Ala Asn
            805                 810                 815

His Gln Ala His Asn Val Thr Leu His Ile Asp Lys Gly Ile
            820                 825                 830
```

```
<210> SEQ ID NO 7
<211> LENGTH: 933
<212> TYPE: PRT
<213> ORGANISM: Homo sapiens

<400> SEQUENCE: 7

Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
            20                  25                  30

Lys Pro Glu Glu Ser Arg Val Ser Ser Val Leu Glu Glu Ser Lys Arg
        35                  40                  45

Leu Val Asp Thr Ala Met Tyr Ala Thr Met Gln Arg Asn Leu Lys Lys
    50                  55                  60

Arg Gly Ile Leu Ser Pro Ala Gln Leu Leu Ser Phe Ser Lys Leu Pro
65                  70                  75                  80

Glu Pro Thr Ser Gly Val Ile Ala Arg Ala Glu Ile Met Glu Thr
                85                  90                  95

Ser Ile Gln Ala Met Lys Arg Lys Val Asn Leu Lys Thr Gln Gln Ser
            100                 105                 110

Gln His Pro Thr Asp Ala Leu Ser Glu Asp Leu Leu Ser Ile Ile Ala
        115                 120                 125

Asn Met Ser Gly Cys Leu Pro Tyr Met Leu Pro Pro Lys Cys Pro Asn
    130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
                165                 170                 175

Leu Pro Pro Val Tyr Glu Asp Gly Phe Ser Gln Pro Arg Gly Trp Asn
            180                 185                 190

Pro Gly Phe Leu Tyr Asn Gly Phe Pro Leu Pro Pro Val Arg Glu Val
        195                 200                 205

Thr Arg His Val Ile Gln Val Ser Asn Glu Val Val Thr Asp Asp Asp
    210                 215                 220

Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255

Ala Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
    290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Ser Pro Ala Leu
                325                 330                 335

Glu Arg Gln Leu Arg Asn Trp Thr Ser Ala Glu Gly Leu Leu Arg Val
            340                 345                 350

His Ala Arg Leu Arg Asp Ser Gly Arg Ala Tyr Leu Pro Phe Val Pro
        355                 360                 365

Pro Arg Ala Pro Ala Ala Cys Ala Pro Glu Pro Gly Ile Pro Gly Glu
    370                 375                 380
```

-continued

```
Thr Arg Gly Pro Cys Phe Leu Ala Gly Asp Gly Arg Ala Ser Glu Val
385                 390                 395                 400

Pro Ser Leu Thr Ala Leu His Thr Leu Trp Leu Arg Glu His Asn Arg
            405                 410                 415

Leu Ala Ala Ala Leu Lys Ala Leu Asn Ala His Trp Ser Ala Asp Ala
        420                 425                 430

Val Tyr Gln Glu Ala Arg Lys Val Val Gly Ala Leu His Gln Ile Ile
    435                 440                 445

Thr Leu Arg Asp Tyr Ile Pro Arg Ile Leu Gly Pro Glu Ala Phe Gln
450                 455                 460

Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
            485                 490                 495

Ile His Pro Leu Val Arg Arg Leu Asp Ala Ser Phe Gln Glu His Pro
        500                 505                 510

Asp Leu Pro Gly Leu Trp Leu His Gln Ala Phe Phe Ser Pro Trp Thr
    515                 520                 525

Leu Leu Arg Gly Gly Gly Leu Asp Pro Leu Ile Arg Gly Leu Leu Ala
530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Ser Thr Leu Asp Leu Ala
            565                 570                 575

Ser Ile Asn Leu Gln Arg Gly Arg Asp His Gly Leu Pro Gly Tyr Asn
        580                 585                 590

Glu Trp Arg Glu Phe Cys Gly Leu Pro Arg Leu Glu Thr Pro Ala Asp
    595                 600                 605

Leu Ser Thr Ala Ile Ala Ser Arg Ser Val Ala Asp Lys Ile Leu Asp
610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
            645                 650                 655

Ile Gly Lys Gln Met Lys Ala Leu Arg Asp Gly Asp Trp Phe Trp Trp
        660                 665                 670

Glu Asn Ser His Val Phe Thr Asp Ala Gln Arg Arg Glu Leu Glu Lys
    675                 680                 685

His Ser Leu Ser Arg Val Ile Cys Asp Asn Thr Gly Leu Thr Arg Val
690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
            725                 730                 735

Pro Gln Asp Asp Lys Cys Gly Phe Pro Glu Ser Val Glu Asn Gly Asp
        740                 745                 750

Phe Val His Cys Glu Ser Gly Arg Arg Val Leu Val Tyr Ser Cys
    755                 760                 765

Arg His Gly Tyr Glu Leu Gln Gly Arg Glu Gln Leu Thr Cys Thr Gln
770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
            805                 810                 815
```

```
Thr Lys Gly Gly Phe Gln Cys Leu Cys Ala Asp Pro Tyr Glu Leu Gly
            820                 825                 830

Asp Asp Gly Arg Thr Cys Val Asp Ser Gly Arg Leu Pro Arg Val Thr
            835                 840                 845

Trp Ile Ser Met Ser Leu Ala Ala Leu Leu Ile Gly Gly Phe Ala Gly
850                 855                 860

Leu Thr Ser Thr Val Ile Cys Arg Trp Thr Arg Thr Gly Thr Lys Ser
865                 870                 875                 880

Thr Leu Pro Ile Ser Glu Thr Gly Gly Thr Pro Glu Leu Arg Cys
            885                 890                 895

Gly Lys His Gln Ala Val Gly Thr Ser Pro Gln Arg Ala Ala Ala Gln
            900                 905                 910

Asp Ser Glu Gln Glu Ser Ala Gly Met Glu Gly Arg Asp Thr His Arg
            915                 920                 925

Leu Pro Arg Ala Leu
            930

<210> SEQ ID NO 8
<211> LENGTH: 715
<212> TYPE: PRT
<213> ORGANISM: Homo sapiens

<400> SEQUENCE: 8

Met His Leu Leu Pro Ala Leu Ala Gly Val Leu Ala Thr Leu Val Leu
1               5                   10                  15

Ala Gln Pro Cys Glu Gly Thr Asp Pro Ala Ser Pro Gly Ala Val Glu
            20                  25                  30

Thr Ser Val Leu Arg Asp Cys Ile Ala Glu Ala Lys Leu Leu Val Asp
            35                  40                  45

Ala Ala Tyr Asn Trp Thr Gln Lys Ser Ile Lys Gln Arg Leu Arg Ser
        50                  55                  60

Gly Ser Ala Ser Pro Met Asp Leu Leu Ser Tyr Phe Lys Gln Pro Val
65                  70                  75                  80

Ala Ala Thr Arg Thr Val Val Arg Ala Ala Asp Tyr Met His Val Ala
                85                  90                  95

Leu Gly Leu Leu Glu Glu Lys Leu Gln Pro Gln Arg Ser Gly Pro Phe
            100                 105                 110

Asn Val Thr Asp Val Leu Thr Glu Pro Gln Leu Arg Leu Leu Ser Gln
            115                 120                 125

Ala Ser Gly Cys Ala Leu Arg Asp Gln Ala Glu Cys Ser Asp Lys
        130                 135                 140

Tyr Arg Thr Ile Thr Gly Arg Cys Asn Asn Lys Arg Arg Pro Leu Leu
145                 150                 155                 160

Gly Ala Ser Asn Gln Ala Leu Ala Arg Trp Leu Pro Ala Glu Tyr Glu
                165                 170                 175

Asp Gly Leu Ser Leu Pro Phe Gly Trp Thr Pro Ser Arg Arg Arg Asn
            180                 185                 190

Gly Phe Leu Leu Pro Leu Val Arg Ala Val Ser Asn Gln Ile Val Arg
            195                 200                 205

Phe Pro Asn Glu Arg Leu Thr Ser Asp Arg Gly Arg Ala Leu Met Phe
        210                 215                 220

Met Gln Trp Gly Gln Phe Ile Asp His Asp Leu Asp Phe Ser Pro Glu
225                 230                 235                 240

Ser Pro Ala Arg Val Ala Phe Thr Ala Gly Val Asp Cys Glu Arg Thr
                245                 250                 255
```

-continued

Cys Ala Gln Leu Pro Pro Cys Phe Pro Ile Lys Ile Pro Pro Asn Asp
            260                 265                 270

Pro Arg Ile Lys Asn Gln Arg Asp Cys Ile Pro Phe Phe Arg Ser Ala
        275                 280                 285

Pro Ser Cys Pro Gln Asn Lys Asn Arg Val Arg Gln Ile Asn Ala
290                 295                 300

Leu Thr Ser Phe Val Asp Ala Ser Met Val Tyr Gly Ser Glu Val Ser
305                 310                 315                 320

Leu Ser Leu Arg Leu Arg Asn Arg Thr Asn Tyr Leu Gly Leu Leu Ala
            325                 330                 335

Ile Asn Gln Arg Phe Gln Asp Asn Gly Arg Ala Leu Leu Pro Phe Asp
            340                 345                 350

Asn Leu His Asp Asp Pro Cys Leu Leu Thr Asn Arg Ser Ala Arg Ile
            355                 360                 365

Pro Cys Phe Leu Ala Gly Asp Thr Arg Ser Thr Glu Thr Pro Lys Leu
370                 375                 380

Ala Ala Met His Thr Leu Phe Met Arg Glu His Asn Arg Leu Ala Thr
385                 390                 395                 400

Glu Leu Arg Arg Leu Asn Pro Arg Trp Asn Gly Asp Lys Leu Tyr Asn
            405                 410                 415

Glu Ala Arg Lys Ile Met Gly Ala Met Val Gln Ile Ile Thr Tyr Arg
            420                 425                 430

Asp Phe Leu Pro Leu Val Leu Gly Lys Ala Arg Ala Arg Arg Thr Leu
            435                 440                 445

Gly His Tyr Arg Gly Tyr Cys Ser Asn Val Asp Pro Arg Val Ala Asn
450                 455                 460

Val Phe Thr Leu Ala Phe Arg Phe Gly His Thr Met Leu Gln Pro Phe
465                 470                 475                 480

Met Phe Arg Leu Asp Ser Gln Tyr Arg Ala Ser Ala Pro Asn Ser His
            485                 490                 495

Val Pro Leu Ser Ser Ala Phe Phe Ala Ser Trp Arg Ile Val Tyr Glu
            500                 505                 510

Gly Gly Ile Asp Pro Ile Leu Arg Gly Leu Met Ala Thr Pro Ala Lys
            515                 520                 525

Leu Asn Arg Gln Asp Ala Met Leu Val Asp Glu Leu Arg Asp Arg Leu
530                 535                 540

Phe Arg Gln Val Arg Arg Ile Gly Leu Asp Leu Ala Ala Leu Asn Met
545                 550                 555                 560

Gln Arg Ser Arg Asp His Gly Leu Pro Gly Tyr Asn Ala Trp Arg Arg
            565                 570                 575

Phe Cys Gly Leu Ser Gln Pro Arg Asn Leu Ala Gln Leu Ser Arg Val
            580                 585                 590

Leu Lys Asn Gln Asp Leu Ala Arg Lys Phe Leu Asn Leu Tyr Gly Thr
            595                 600                 605

Pro Asp Asn Ile Asp Ile Trp Ile Gly Ala Ile Ala Glu Pro Leu Leu
        610                 615                 620

Pro Gly Ala Arg Val Gly Pro Leu Leu Ala Cys Leu Phe Glu Asn Gln
625                 630                 635                 640

Phe Arg Arg Ala Arg Asp Gly Asp Arg Phe Trp Trp Gln Lys Arg Gly
            645                 650                 655

Val Phe Thr Lys Arg Gln Arg Lys Ala Leu Ser Arg Ile Ser Leu Ser
            660                 665                 670

Arg Ile Ile Cys Asp Asn Thr Gly Ile Thr Thr Val Ser Arg Asp Ile

```
            675                 680                 685
Phe Arg Ala Asn Ile Tyr Pro Arg Gly Phe Val Asn Cys Ser Arg Ile
    690                 695                 700

Pro Arg Leu Asn Leu Ser Ala Trp Arg Gly Thr
705                 710                 715

<210> SEQ ID NO 9
<211> LENGTH: 745
<212> TYPE: PRT
<213> ORGANISM: Homo sapiens

<400> SEQUENCE: 9

Met Gly Val Pro Phe Ser Ser Leu Arg Cys Met Val Asp Leu Gly
1               5                   10                  15

Pro Cys Trp Ala Gly Gly Leu Thr Ala Glu Met Lys Leu Leu Leu Ala
                20                  25                  30

Leu Ala Gly Leu Leu Ala Ile Leu Ala Thr Pro Gln Pro Ser Glu Gly
            35                  40                  45

Ala Ala Pro Ala Val Leu Gly Glu Val Asp Thr Ser Leu Val Leu Ser
        50                  55                  60

Ser Met Glu Glu Ala Lys Gln Leu Val Asp Lys Ala Tyr Lys Glu Arg
65                  70                  75                  80

Arg Glu Ser Ile Lys Gln Arg Leu Arg Ser Gly Ser Ala Ser Pro Met
                85                  90                  95

Glu Leu Leu Ser Tyr Phe Lys Gln Pro Val Ala Ala Thr Arg Thr Ala
            100                 105                 110

Val Arg Ala Ala Asp Tyr Leu His Val Ala Leu Asp Leu Leu Glu Arg
        115                 120                 125

Lys Leu Arg Ser Leu Trp Arg Arg Pro Phe Asn Val Thr Asp Val Leu
130                 135                 140

Thr Pro Ala Gln Leu Asn Val Leu Ser Lys Ser Ser Gly Cys Ala Tyr
145                 150                 155                 160

Gln Asp Val Gly Val Thr Cys Pro Glu Gln Asp Lys Tyr Arg Thr Ile
                165                 170                 175

Thr Gly Met Cys Asn Asn Arg Arg Ser Pro Thr Leu Gly Ala Ser Asn
            180                 185                 190

Arg Ala Phe Val Arg Trp Leu Pro Ala Glu Tyr Glu Asp Gly Phe Ser
        195                 200                 205

Leu Pro Tyr Gly Trp Thr Pro Gly Val Lys Arg Asn Gly Phe Pro Val
210                 215                 220

Ala Leu Ala Arg Ala Val Ser Asn Glu Ile Val Arg Phe Pro Thr Asp
225                 230                 235                 240

Gln Leu Thr Pro Asp Gln Glu Arg Ser Leu Met Phe Met Gln Trp Gly
                245                 250                 255

Gln Leu Leu Asp His Asp Leu Asp Phe Thr Pro Glu Pro Ala Ala Arg
            260                 265                 270

Ala Ser Phe Val Thr Gly Val Asn Cys Glu Thr Ser Cys Val Gln Gln
        275                 280                 285

Pro Pro Cys Phe Pro Leu Lys Ile Pro Pro Asn Asp Pro Arg Ile Lys
290                 295                 300

Asn Gln Ala Asp Cys Ile Pro Phe Phe Arg Ser Cys Pro Ala Cys Pro
305                 310                 315                 320

Gly Ser Asn Ile Thr Ile Arg Asn Gln Ile Asn Ala Leu Thr Ser Phe
                325                 330                 335

Val Asp Ala Ser Met Val Tyr Gly Ser Glu Glu Pro Leu Ala Arg Asn
```

```
                340             345             350
Leu Arg Asn Met Ser Asn Gln Leu Gly Leu Leu Ala Val Asn Gln Arg
            355                 360                 365
Phe Gln Asp Asn Gly Arg Ala Leu Leu Pro Phe Asp Asn Leu His Asp
        370                 375                 380
Asp Pro Cys Leu Leu Thr Asn Arg Ser Ala Arg Ile Pro Cys Phe Leu
385                 390                 395                 400
Ala Gly Asp Thr Arg Ser Ser Glu Met Pro Glu Leu Thr Ser Met His
            405                 410                 415
Thr Leu Leu Leu Arg Glu His Asn Arg Leu Ala Thr Glu Leu Lys Ser
        420                 425                 430
Leu Asn Pro Arg Trp Asp Gly Glu Arg Leu Tyr Gln Glu Ala Arg Lys
        435                 440                 445
Ile Val Gly Ala Met Val Gln Ile Ile Thr Tyr Arg Asp Tyr Leu Pro
        450                 455                 460
Leu Val Leu Gly Pro Thr Ala Met Arg Lys Tyr Leu Pro Thr Tyr Arg
465                 470                 475                 480
Ser Tyr Asn Asp Ser Val Asp Pro Arg Ile Ala Asn Val Phe Thr Asn
            485                 490                 495
Ala Phe Arg Tyr Gly His Thr Leu Ile Gln Pro Phe Met Phe Arg Leu
        500                 505                 510
Asp Asn Arg Tyr Gln Pro Met Glu Pro Asn Pro Arg Val Pro Leu Ser
        515                 520                 525
Arg Val Phe Phe Ala Ser Trp Arg Val Val Leu Glu Gly Gly Ile Asp
        530                 535                 540
Pro Ile Leu Arg Gly Leu Met Ala Thr Pro Ala Lys Leu Asn Arg Gln
545                 550                 555                 560
Asn Gln Ile Ala Val Asp Glu Ile Arg Glu Arg Leu Phe Glu Gln Val
            565                 570                 575
Met Arg Ile Gly Leu Asp Leu Pro Ala Leu Asn Met Gln Arg Ser Arg
        580                 585                 590
Asp His Gly Leu Pro Gly Tyr Asn Ala Trp Arg Arg Phe Cys Gly Leu
        595                 600                 605
Pro Gln Pro Glu Thr Val Gly Gln Leu Gly Thr Val Leu Arg Asn Leu
        610                 615                 620
Lys Leu Ala Arg Lys Leu Met Glu Gln Tyr Gly Thr Pro Asn Asn Ile
625                 630                 635                 640
Asp Ile Trp Met Gly Gly Val Ser Glu Pro Leu Lys Arg Lys Gly Arg
            645                 650                 655
Val Gly Pro Leu Leu Ala Cys Ile Ile Gly Thr Gln Phe Arg Lys Leu
        660                 665                 670
Arg Asp Gly Asp Arg Phe Trp Trp Glu Asn Glu Gly Val Phe Ser Met
        675                 680                 685
Gln Gln Arg Gln Ala Leu Ala Gln Ile Ser Leu Pro Arg Ile Ile Cys
        690                 695                 700
Asp Asn Thr Gly Ile Thr Thr Val Ser Lys Asn Asn Ile Phe Met Ser
705                 710                 715                 720
Asn Ser Tyr Pro Arg Asp Phe Val Asn Cys Ser Thr Leu Pro Ala Leu
            725                 730                 735
Asn Leu Ala Ser Trp Arg Glu Ala Ser
        740                 745

<210> SEQ ID NO 10
<211> LENGTH: 712
```

```
<212> TYPE: PRT
<213> ORGANISM: Homo sapiens

<400> SEQUENCE: 10

Met Arg Val Leu Leu His Leu Pro Ala Leu Ala Ser Leu Ile Leu
1               5                   10                  15

Leu Gln Ala Ala Ala Ser Thr Thr Arg Ala Gln Thr Thr Arg Thr Ser
                20                  25                  30

Ala Ile Ser Asp Thr Val Ser Gln Ala Lys Val Gln Val Asn Lys Ala
            35                  40                  45

Phe Leu Asp Ser Arg Thr Arg Leu Lys Thr Ala Met Ser Ser Glu Thr
    50                  55                  60

Pro Thr Ser Arg Gln Leu Ser Glu Tyr Leu Lys His Ala Lys Gly Arg
65                  70                  75                  80

Thr Arg Thr Ala Ile Arg Asn Gly Gln Val Trp Glu Ser Leu Lys
                85                  90                  95

Arg Leu Arg Gln Lys Ala Ser Leu Thr Asn Val Thr Asp Pro Ser Leu
            100                 105                 110

Asp Leu Thr Ser Leu Ser Leu Glu Val Gly Cys Gly Ala Pro Ala Pro
        115                 120                 125

Val Val Arg Cys Asp Pro Cys Ser Pro Tyr Arg Thr Ile Thr Gly Asp
    130                 135                 140

Cys Asn Asn Arg Arg Lys Pro Ala Leu Gly Ala Ala Asn Arg Ala Leu
145                 150                 155                 160

Ala Arg Trp Leu Pro Ala Glu Tyr Glu Asp Gly Leu Ser Leu Pro Phe
                165                 170                 175

Gly Trp Thr Pro Gly Lys Thr Arg Asn Gly Phe Pro Leu Pro Leu Ala
            180                 185                 190

Arg Glu Val Ser Asn Lys Ile Val Gly Tyr Leu Asn Glu Glu Gly Val
        195                 200                 205

Leu Asp Gln Asn Arg Ser Leu Leu Phe Met Gln Trp Gly Gln Ile Val
    210                 215                 220

Asp His Asp Leu Asp Phe Ala Pro Asp Thr Glu Leu Gly Ser Ser Glu
225                 230                 235                 240

Tyr Ser Lys Ala Gln Cys Asp Glu Tyr Cys Ile Gln Gly Asp Asn Cys
                245                 250                 255

Phe Pro Ile Met Phe Pro Pro Asn Asp Pro Lys Ala Gly Thr Gln Gly
            260                 265                 270

Lys Cys Met Pro Phe Phe Arg Ala Gly Phe Val Cys Pro Thr Pro Pro
        275                 280                 285

Tyr Lys Ser Leu Ala Arg Glu Gln Ile Asn Ala Leu Thr Ser Phe Leu
    290                 295                 300

Asp Ala Ser Phe Val Tyr Ser Ser Glu Pro Ser Leu Ala Ser Arg Leu
305                 310                 315                 320

Arg Asn Leu Ser Ser Pro Leu Gly Leu Met Ala Val Asn Gln Glu Val
                325                 330                 335

Ser Asp His Gly Leu Pro Tyr Leu Pro Tyr Asp Ser Lys Lys Pro Ser
            340                 345                 350

Pro Cys Glu Phe Ile Asn Thr Thr Ala Arg Val Pro Cys Phe Leu Ala
        355                 360                 365

Gly Asp Ser Arg Ala Ser Glu His Ile Leu Leu Ala Thr Ser His Thr
    370                 375                 380

Leu Phe Leu Arg Glu His Asn Arg Leu Ala Arg Glu Leu Lys Arg Leu
385                 390                 395                 400
```

-continued

```
Asn Pro Gln Trp Asp Gly Glu Lys Leu Tyr Gln Ala Arg Lys Ile
            405                 410                 415

Leu Gly Ala Phe Val Gln Ile Ile Thr Phe Arg Asp Tyr Leu Pro Ile
        420                 425                 430

Leu Leu Gly Asp His Met Gln Lys Trp Ile Pro Pro Tyr Gln Gly Tyr
            435                 440                 445

Ser Glu Ser Val Asp Pro Arg Ile Ser Asn Val Phe Thr Phe Ala Phe
    450                 455                 460

Arg Phe Gly His Leu Glu Val Pro Ser Ser Met Phe Arg Leu Asp Glu
465                 470                 475                 480

Asn Tyr Gln Pro Trp Gly Pro Glu Pro Glu Leu Pro Leu His Thr Leu
            485                 490                 495

Phe Phe Asn Thr Trp Arg Met Val Lys Asp Gly Gly Ile Asp Pro Leu
        500                 505                 510

Val Arg Gly Leu Leu Ala Lys Lys Ser Lys Leu Met Lys Gln Asn Lys
    515                 520                 525

Met Met Thr Gly Glu Leu Arg Asn Lys Leu Phe Gln Pro Thr His Arg
530                 535                 540

Ile His Gly Phe Asp Leu Ala Ala Ile Asn Thr Gln Arg Cys Arg Asp
545                 550                 555                 560

His Gly Gln Pro Gly Tyr Asn Ser Trp Arg Ala Phe Cys Asp Leu Ser
            565                 570                 575

Gln Pro Gln Thr Leu Glu Glu Leu Asn Thr Val Leu Lys Ser Lys Met
        580                 585                 590

Leu Ala Lys Lys Leu Leu Gly Leu Tyr Gly Thr Pro Asp Asn Ile Asp
    595                 600                 605

Ile Trp Ile Gly Ala Ile Ala Glu Pro Leu Val Glu Arg Gly Arg Val
610                 615                 620

Gly Pro Leu Leu Ala Cys Leu Leu Gly Lys Gln Phe Gln Gln Ile Arg
625                 630                 635                 640

Asp Gly Asp Arg Phe Trp Trp Glu Asn Pro Gly Val Phe Thr Asn Glu
            645                 650                 655

Gln Lys Asp Ser Leu Gln Lys Met Ser Phe Ser Arg Leu Val Cys Asp
        660                 665                 670

Asn Thr Arg Ile Thr Lys Val Pro Arg Asp Pro Phe Trp Ala Asn Ser
    675                 680                 685

Tyr Pro Tyr Asp Phe Val Asp Cys Ser Ala Ile Asp Lys Leu Asp Leu
690                 695                 700

Ser Pro Trp Ala Ser Val Lys Asn
705                 710

<210> SEQ ID NO 11
<211> LENGTH: 718
<212> TYPE: PRT
<213> ORGANISM: Mus musculus

<400> SEQUENCE: 11

Met Lys Leu Leu Leu Ala Leu Ala Gly Leu Leu Ala Pro Leu Ala Met
1               5                   10                  15

Leu Gln Thr Ser Asn Gly Ala Thr Pro Ala Leu Leu Gly Glu Val Glu
            20                  25                  30

Asn Ser Val Val Leu Ser Cys Met Glu Glu Ala Lys Gln Leu Val Asp
        35                  40                  45

Arg Ala Tyr Lys Glu Arg Arg Glu Ser Ile Lys Arg Thr Leu Gln Ser
    50                  55                  60
```

-continued

```
Gly Ser Ala Ser Pro Thr Glu Leu Leu Phe Tyr Phe Lys Gln Pro Val
 65                  70                  75                  80

Ala Gly Thr Arg Thr Ala Val Arg Ala Ala Asp Tyr Leu His Val Ala
             85                  90                  95

Leu Asp Leu Leu Lys Arg Lys Leu Gln Pro Leu Trp Pro Arg Pro Phe
            100                 105                 110

Asn Val Thr Asp Val Leu Thr Pro Ala Gln Leu Asn Leu Leu Ser Val
        115                 120                 125

Ser Ser Gly Cys Ala Tyr Gln Asp Val Gly Val Thr Cys Pro Pro Asn
130                 135                 140

Asp Lys Tyr Arg Thr Ile Thr Gly His Cys Asn Asn Arg Arg Ser Pro
145                 150                 155                 160

Thr Leu Gly Ala Ser Asn Arg Ala Phe Val Arg Trp Leu Pro Ala Glu
            165                 170                 175

Tyr Glu Asp Gly Val Ser Met Pro Phe Gly Trp Thr Pro Gly Val Asn
        180                 185                 190

Arg Asn Gly Phe Lys Val Pro Leu Ala Arg Gln Val Ser Asn Ala Ile
    195                 200                 205

Val Arg Phe Pro Asn Asp Gln Leu Thr Lys Asp Gln Glu Arg Ala Leu
210                 215                 220

Met Phe Met Gln Trp Gly Gln Phe Leu Asp His Asp Ile Thr Leu Thr
225                 230                 235                 240

Pro Glu Pro Ala Thr Arg Phe Ser Phe Thr Gly Leu Asn Cys Glu
            245                 250                 255

Thr Ser Cys Leu Gln Gln Pro Pro Cys Phe Pro Leu Lys Ile Pro Pro
        260                 265                 270

Asn Asp Pro Arg Ile Lys Asn Gln Lys Asp Cys Ile Pro Phe Phe Arg
    275                 280                 285

Ser Cys Pro Ala Cys Thr Arg Asn Asn Ile Thr Ile Arg Asn Gln Ile
290                 295                 300

Asn Ala Leu Thr Ser Phe Val Asp Ala Ser Gly Val Tyr Gly Ser Glu
305                 310                 315                 320

Asp Pro Leu Ala Arg Lys Leu Arg Asn Leu Thr Asn Gln Leu Gly Leu
            325                 330                 335

Leu Ala Val Asn Thr Arg Phe Gln Asp Asn Gly Arg Ala Leu Met Pro
        340                 345                 350

Phe Asp Ser Leu His Asp Asp Pro Cys Leu Leu Thr Asn Arg Ser Ala
    355                 360                 365

Arg Ile Pro Cys Phe Leu Ala Gly Asp Met Arg Ser Ser Glu Met Pro
370                 375                 380

Glu Leu Thr Ser Met His Thr Leu Phe Val Arg Glu His Asn Arg Leu
385                 390                 395                 400

Ala Thr Gln Leu Lys Arg Leu Asn Pro Arg Trp Asn Gly Glu Lys Leu
            405                 410                 415

Tyr Gln Glu Ala Arg Lys Ile Val Gly Ala Met Val Gln Ile Ile Thr
        420                 425                 430

Tyr Arg Asp Tyr Leu Pro Leu Val Leu Gly Pro Ala Ala Met Lys Lys
    435                 440                 445

Tyr Leu Pro Gln Tyr Arg Ser Tyr Asn Asp Ser Val Asp Pro Arg Ile
450                 455                 460

Ala Asn Val Phe Thr Asn Ala Phe Arg Tyr Gly His Thr Leu Ile Gln
465                 470                 475                 480

Pro Phe Met Phe Arg Leu Asn Asn Gln Tyr Arg Pro Thr Ala Ala Asn
            485                 490                 495
```

```
Pro Arg Val Pro Leu Ser Lys Val Phe Phe Ala Ser Trp Arg Val Val
            500                 505                 510

Leu Glu Gly Gly Ile Asp Pro Ile Leu Arg Gly Leu Met Ala Thr Pro
        515                 520                 525

Ala Lys Leu Asn Arg Gln Asn Gln Ile Val Val Asp Glu Ile Arg Glu
    530                 535                 540

Arg Leu Phe Glu Gln Val Met Arg Ile Gly Leu Asp Leu Pro Ala Leu
545                 550                 555                 560

Asn Met Gln Arg Ser Arg Asp His Gly Leu Pro Gly Tyr Asn Ala Trp
                565                 570                 575

Arg Arg Phe Cys Gly Leu Pro Gln Pro Ser Thr Val Gly Glu Leu Gly
            580                 585                 590

Thr Val Leu Lys Asn Leu Glu Leu Ala Arg Lys Leu Met Ala Gln Tyr
        595                 600                 605

Gly Thr Pro Asn Asn Ile Asp Ile Trp Met Gly Gly Val Ser Glu Pro
    610                 615                 620

Leu Glu Pro Asn Gly Arg Val Gly Gln Leu Leu Ala Cys Leu Ile Gly
625                 630                 635                 640

Thr Gln Phe Arg Lys Leu Arg Asp Gly Asp Arg Phe Trp Trp Glu Asn
                645                 650                 655

Pro Gly Val Phe Ser Lys Gln Gln Arg Gln Ala Leu Ala Ser Ile Ser
            660                 665                 670

Leu Pro Arg Leu Ile Cys Asp Asn Thr Gly Ile Thr Thr Val Ser Lys
        675                 680                 685

Asn Asn Ile Phe Met Ser Asn Thr Tyr Pro Arg Asp Phe Val Ser Cys
    690                 695                 700

Asn Thr Leu Pro Lys Leu Asn Leu Thr Ser Trp Lys Glu Thr
705                 710                 715

<210> SEQ ID NO 12
<211> LENGTH: 705
<212> TYPE: PRT
<213> ORGANISM: Anopheles gambiae

<400> SEQUENCE: 12

Gly Ser Ile Gly Gln Arg Cys Pro Thr Ile Val Ala Asp Glu Ser
1               5                   10                  15

Ser Pro Glu Trp Asn Gly Thr Ala Val Ser Asp Asp Ala Lys Ala Ala
                20                  25                  30

Ala Ile Ala Asp Gly Glu Lys Ala Leu Gly Asp Lys Glu Leu Leu Glu
            35                  40                  45

Glu Thr Leu Ser Ser Pro Pro Leu Asn Ser Pro Ser Phe Arg His Gln
        50                  55                  60

Lys Ser Val Gly Ala Thr Lys Ala Ala Arg Leu Ala Ala Lys Val Gly
65                  70                  75                  80

Phe Val Glu Asp Arg Ala Thr Gln Ala Leu Val Arg Arg Leu Asp Ile
                85                  90                  95

Arg Arg Arg Gly Ser Ile Gly Arg Gly Pro Met Asp Leu Pro Arg
            100                 105                 110

Ala His Arg Gln Pro Arg Cys Asp Phe Asn Ala Arg Tyr Arg Thr Ala
        115                 120                 125

Asn Gly Thr Cys Asn Ser Lys Glu Arg Pro Tyr Glu Tyr Gly Val Ala
    130                 135                 140

Met Ile Pro Phe Arg Arg Gln Leu Asn Pro Asp Tyr Gly Asp Gly Ile
145                 150                 155                 160
```

-continued

Ser Ala Pro Arg Ala Ser Val Asp Gly Ala Glu Leu Pro Ser Ala Arg
                165                 170                 175

Gln Val Ser Leu Glu Ile His Arg Pro Ser Tyr His Asn Asp Pro Asn
            180                 185                 190

Phe Ser Val Met Leu Ala Val Trp Gly Gln Phe Leu Asp His Asp Ile
        195                 200                 205

Thr Ser Thr Ala Leu Asn Gln Gly Val Asp Gly Lys Pro Ile Glu Cys
    210                 215                 220

Cys Asp Pro Gly Gln Pro Gln His Pro Glu Cys Phe Pro Val Pro Leu
225                 230                 235                 240

Gly Pro Gly Asp Pro Tyr Tyr Thr Gln Tyr Asn Val Thr Cys Met Asn
                245                 250                 255

Phe Val Arg Ser Val Pro Ala Pro Thr Gly His Phe Gly Pro Arg Gln
            260                 265                 270

Gln Leu Asn Gln Ala Thr Ala Phe Ile Asp Gly Ser Val Val Tyr Gly
        275                 280                 285

Ser Asp Asp Glu Arg Met Gly Ala Leu Arg Thr Gly Ala Gly Gly Gln
    290                 295                 300

Leu Arg Met Leu Arg Thr Pro Asp Gly Arg Asp Leu Leu Pro Val Ser
305                 310                 315                 320

Thr Asp Pro Leu Asp Gly Cys Asn Glu Gln Glu Met Asn Ala Ala Gly
                325                 330                 335

Lys Tyr Cys Phe Glu Ser Gly Asp Ala Arg Ala Asn Glu Asn Leu His
            340                 345                 350

Leu Thr Ser Met His Leu Ile Trp Ala Arg His His Asn Ser Leu Ala
        355                 360                 365

Arg Gly Leu Ala Arg Ala Asn Pro His Trp Asp Asp Glu Arg Leu Phe
    370                 375                 380

Gln Glu Ala Arg Arg Ile Leu Ala Ala Gln Met Gln His Ile Thr Tyr
385                 390                 395                 400

Ala Glu Phe Val Pro Val Ile Gly Asn Glu Thr Ala Gly Arg Met
                405                 410                 415

Gly Leu Leu Pro Val Ser Ala Gly Gly Glu Pro Ala Gly Asp Thr Tyr
            420                 425                 430

Asn Ala Thr Val Asp Ala Ser Ile Ala Asn Val Phe Ala Gly Ala Ala
        435                 440                 445

Phe Arg Phe Ala His Thr Leu Leu Pro Gly Leu Met Lys Gln Thr Arg
    450                 455                 460

Asn Pro Ala Ala Ser Ala Ser Gly Ile Glu Leu His Arg Met Leu Phe
465                 470                 475                 480

Asn Pro Tyr Ser Leu Tyr Ala Arg Asp Gly Leu Asp Asn Ala Leu Gly
                485                 490                 495

Gly Ala Ile Gly Thr Ala Leu Ala Lys Tyr Asp Gln Tyr Phe Ser Thr
            500                 505                 510

Glu Leu Thr Glu Arg Leu Phe Glu Lys Ala Asp Glu His Leu Leu His
        515                 520                 525

Gly Gln Pro Cys Gly Leu Asp Leu Val Ser Leu Asn Ile Gln Arg Gly
    530                 535                 540

Arg Asp His Gly Leu Pro Ala Tyr Pro Trp Arg Lys His Cys His
545                 550                 555                 560

Leu Thr Pro Ala Asp Ser Trp Glu Glu Leu Arg Ile Val Asp Pro
                565                 570                 575

Glu Ser Tyr Arg Gln Met Arg Arg Ile Tyr Arg Glu Pro Ala Asn Val

-continued

```
                580                 585                 590
Asp Val Tyr Ser Gly Ala Leu Ser Glu Ala Pro Val Arg Asp Gly Ile
            595                 600                 605

Val Gly Pro Leu Leu Thr Cys Leu Ile Gly Asp Gln Phe Leu Arg Leu
610                 615                 620

Lys Gln Gly Asp Ser Phe Trp Tyr Glu Arg Arg Gly Pro Gln Arg
625                 630                 635                 640

Phe Thr Glu Ala Gln Leu Gln Gln Ile Tyr Asn Thr Lys Leu Ser Ser
            645                 650                 655

Ile Ile Cys Arg Asn Ser Asp His Ile Glu Gln Ser Pro Val Tyr Leu
            660                 665                 670

Met Lys Arg Thr Asp Ser Arg Thr Asn Pro Glu Thr Asp Cys Lys Gln
            675                 680                 685

Leu Asp Thr Phe Asp Phe Glu Pro Phe Arg Glu Asp Ala Glu Gln Pro
            690                 695                 700

Gln
705

<210> SEQ ID NO 13
<211> LENGTH: 734
<212> TYPE: PRT
<213> ORGANISM: Canis familiaris

<400> SEQUENCE: 13

Met His Cys Ala Leu Arg Thr Tyr Trp Ala Ser Gly Leu Val Ala Glu
1               5                   10                  15

Met Leu Leu Leu Leu Ala Leu Ala Gly Leu Ala Ile Leu Ala Val
            20                  25                  30

Pro Gln His Ser Glu Ser Ala Asn Pro Ala Val Leu Glu Val Glu Thr
            35                  40                  45

Thr Val Val Met Thr Cys Met Glu Glu Ala Lys Arg Leu Val Asp Thr
        50                  55                  60

Ala Tyr Lys Glu Arg Arg Glu Ser Ile Lys Gln Arg Leu His Ser Gly
65              70                  75                  80

Leu Ala Ser Pro Met Glu Leu Leu Ser Tyr Phe Lys Gln Pro Val Ala
                85                  90                  95

Ala Thr Arg Thr Ala Val Arg Ala Ala Asp Tyr Leu His Val Ala Leu
            100                 105                 110

Ser Leu Leu Glu Gly Lys Leu Arg Pro Leu Trp Pro Arg Pro Phe Asn
        115                 120                 125

Val Thr Asp Val Leu Thr Pro Ala Gln Leu Asn Leu Leu Ser Lys Ser
130                 135                 140

Ser Gly Cys Ala Tyr Gln Asp Val Gly Leu Lys Cys Pro Glu Asn Asp
145                 150                 155                 160

Lys Tyr Arg Ser Ile Thr Gly His Cys Asn Asn Arg Arg Ser Pro Thr
                165                 170                 175

Leu Gly Ala Ser Asn Arg Ala Phe Ala Arg Trp Leu Pro Ala Glu Tyr
            180                 185                 190

Glu Asp Gly Phe Ser Leu Pro Tyr Gly Trp Thr Pro Gly Val Lys Arg
        195                 200                 205

Ser Gly Phe Pro Val Pro Leu Ala Arg Ala Val Ser Asn Ala Ile Val
    210                 215                 220

Arg Phe Pro Thr Glu Gln Leu Thr Pro Asp Gln Glu Arg Ser Leu Leu
225                 230                 235                 240

Phe Met Gln Trp Gly Gln Leu Leu Asp His Asp Leu Asp Leu Ser Pro
```

-continued

```
                245                 250                 255
Glu Pro Ala Ala Arg Val Ser Phe Val Thr Ser Val Asn Cys Glu Ile
            260                 265                 270
Ser Cys Glu Gln Gln Pro Pro Cys Phe Pro Leu Lys Ile Pro Pro Asn
        275                 280                 285
Asp Pro Arg Ile Lys Asn Gln Arg Asp Cys Ile Pro Phe Phe Arg Ser
    290                 295                 300
Ser Pro Ala Cys Thr Asp Asn Asn Ile Thr Ile Arg Asn Gln Ile Asn
305                 310                 315                 320
Ala Leu Thr Ser Phe Val Asp Ala Ser Met Val Tyr Gly Ser Glu Asp
            325                 330                 335
Pro Leu Ala Thr Arg Leu Arg Asn Leu Thr Asn Gln Leu Gly Leu Leu
        340                 345                 350
Ala Val Asn Thr Arg Phe Ser Asp Asn Gly Arg Ala Leu Leu Pro Phe
    355                 360                 365
Asp Asn Leu His Asp Asp Pro Cys Leu Leu Thr Asn Arg Ser Ala Gly
    370                 375                 380
Ile Pro Cys Phe Leu Ala Gly Asp Thr Arg Ser Ser Glu Met Pro Glu
385                 390                 395                 400
Leu Ala Ser Met His Thr Leu Phe Leu Arg Glu His Asn Arg Leu Ala
            405                 410                 415
Thr Glu Leu Arg Arg Leu Asn Pro Arg Trp Asp Gly Glu Arg Leu Tyr
        420                 425                 430
Gln Glu Ala Arg Lys Ile Val Gly Ala Met Val Gln Ile Ile Thr Tyr
    435                 440                 445
Arg Asp Tyr Leu Pro Leu Val Leu Gly Pro Leu Ala Met Arg Lys Tyr
450                 455                 460
Leu Pro Arg Tyr Arg Ser Tyr Asn Asp Ser Val Asp Pro Arg Ile Ser
465                 470                 475                 480
Asn Val Phe Thr Asn Ala Phe Arg Tyr Gly His Thr Leu Ile Gln Pro
            485                 490                 495
Phe Met Phe Arg Leu Asp Asn Arg Tyr Gln Pro Met Gly Pro Asn Pro
        500                 505                 510
Arg Val Pro Leu Ser Arg Val Phe Phe Ala Thr Trp Arg Val Val Leu
    515                 520                 525
Glu Gly Gly Ile Asp Pro Ile Leu Arg Gly Leu Met Ala Thr Pro Ala
    530                 535                 540
Lys Leu Asn Arg Gln Asn Gln Ile Val Val Asp Glu Ile Arg Glu Arg
545                 550                 555                 560
Leu Phe Glu Gln Val Met Arg Ile Gly Leu Asp Leu Pro Ala Leu Asn
            565                 570                 575
Met Gln Arg Ser Arg Asp His Gly Leu Pro Gly Tyr Asn Ala Trp Arg
        580                 585                 590
Arg Phe Cys Gly Leu Pro Gln Pro Ser Thr Val Gly Glu Leu Ala Thr
    595                 600                 605
Val Leu Arg Asn Leu Asp Leu Ala Gln Lys Leu Met Gln Gln Tyr Gly
    610                 615                 620
Thr Pro Asp Asn Ile Asp Ile Trp Met Gly Gly Val Ala Glu Pro Leu
625                 630                 635                 640
Glu Pro Arg Gly Arg Val Gly Gln Leu Leu Ala Cys Leu Ile Gly Thr
            645                 650                 655
Gln Phe Arg Lys Leu Arg Asp Gly Asp Arg Phe Trp Trp Glu Asn Arg
        660                 665                 670
```

-continued

```
Gly Val Phe Ser Ser Gln Gln Gln Ala Leu Ala Arg Ile Ser Leu
        675                 680                 685

Pro Arg Ile Ile Cys Asp Asn Thr Gly Ile Thr Thr Val Ser Lys Asn
690                 695                 700

Asn Ile Phe Met Ser Asn Met Phe Pro Arg Asp Phe Val Asn Cys Ser
705                 710                 715                 720

Thr Leu Pro Ala Leu Asp Leu Thr Ser Trp Arg Asp Ser Asn
                725                 730

<210> SEQ ID NO 14
<211> LENGTH: 1432
<212> TYPE: PRT
<213> ORGANISM: Caenorhabditis elegans

<400> SEQUENCE: 14

Met Lys Gln Glu Ile Ile Thr Thr Ala Ala Ser Ser Ala Val Arg Leu
1               5                   10                  15

Thr Glu Lys Leu Phe Asn Asp Thr Glu Lys Leu Met Ser Asp Lys Phe
            20                  25                  30

Asp Gly Lys Leu Gly Asn Trp Leu Lys Ser Pro Lys Thr Leu Lys Ser
        35                  40                  45

Met Ile Gln Phe Leu Pro Thr Glu Asn Thr Lys Met Lys Glu Ile Cys
50                  55                  60

Pro Val Asn Gln Ile Glu Cys Val Ile Gly Lys Tyr Arg Ser Tyr
65                  70                  75                  80

Thr Gly His Cys Asn Asn Val Lys Asn Pro Leu Asn Gly Ala Ser Tyr
                85                  90                  95

Glu Arg Leu Lys Arg Phe Leu Pro Ala Asp Tyr Ser Asp Gly Ile Ser
            100                 105                 110

Ala Pro Arg Ser Ser Lys Ser Gly Gln Pro Leu Pro Ser Ser Arg Ala
        115                 120                 125

Leu Ser Ala Leu Phe Thr Pro Ser Pro Ser Gly His Ala Thr Cys Ser
130                 135                 140

Leu Leu Ile Ala Pro Phe Leu Ser Phe Ile Tyr Asp Asp Ile Val His
145                 150                 155                 160

Val Pro Ser Asn Arg Ile Phe Lys Arg Asp Phe Tyr Gly Asn Asp Lys
                165                 170                 175

Ala Met Pro Leu Pro Cys Cys Arg Gly Asp Asn Ser His Pro Glu Cys
            180                 185                 190

Phe Glu Ile Pro Val Pro Glu Asp Asp Thr Leu Gln Ser Lys Asn Val
        195                 200                 205

Lys Cys Leu Pro Tyr Ser Arg Ser Leu Pro Val Pro Asn Pro Lys Cys
210                 215                 220

Ser Phe Gly Gln Arg Gln Gln Ala Asn Met Val Thr Ser Tyr Leu Asp
225                 230                 235                 240

Leu Ser Gln Ile Tyr Gly Ser Thr Glu Gly Ile Val Lys Lys Met Arg
                245                 250                 255

Leu His Lys Asn Gly Lys Leu Ala Leu Arg Ala Val Gly Gly Phe Asn
            260                 265                 270

Asn Gln Leu Gly Val Pro Pro Ala Asn Leu Asp Ser Ser Ile Cys Arg
        275                 280                 285

Ser Ser Thr Gly Lys Pro Cys Leu Leu Ala Gly Asn Asn Lys Ile Asn
290                 295                 300

Phe Leu Pro Thr Ser Gly Ala Ile Tyr Thr Ile Trp Met Arg Gln His
305                 310                 315                 320
```

-continued

Asn Val Ile Ala Asp Lys Leu Ala Ser Val Asn Pro His Trp Asp Asp
            325                 330                 335

Gln Lys Val Phe Glu Glu Ala Arg Arg Ile Thr Ile Ala Gln Phe Gln
            340                 345                 350

His Ile Thr Phe Asn Glu Met Val Pro Val Leu Val Gly Lys Glu Gln
            355                 360                 365

Leu Arg Val Met Gly Ile Lys Leu Gln Lys Asn Gly Tyr Asp Ser Gly
        370                 375                 380

Tyr Asp Ile Asn Ile Asp Ser Ser Ala Ser Asn Val Phe Ala Ser Ala
385                 390                 395                 400

Ala Gly Gln Phe Phe Leu Thr Leu Leu Pro Ser Gln Phe Asn Ile Glu
            405                 410                 415

Asp Lys Arg Phe Ser Thr Lys Ser Glu Ser Leu Leu Lys His Phe Asn
            420                 425                 430

Asp Pro Ala Leu Ile Tyr Glu Lys Gly Arg Ile Asp Gly Met Leu Lys
            435                 440                 445

Phe Leu Leu Asn Ala Pro Ile Glu Lys Pro Gly Leu His Ser Ser Pro
450                 455                 460

Leu Leu Arg Thr Ala Phe Gln Lys Lys Asp Ile Ala Asp Ser Val Asp
465                 470                 475                 480

Ile Ile Ala Met Val Ile Gln Met Gly Arg Asp His Gly Leu Pro Ser
            485                 490                 495

Tyr Leu Gln Trp Arg Thr Phe Cys Lys Leu Asp Asp Phe Ser Ser Phe
            500                 505                 510

Leu Ala Leu Gln Thr Ile Phe Lys Pro Ser Val Asn Ile Ser Asp Phe
            515                 520                 525

Glu Arg Leu Tyr Glu Ser Pro Glu Asp Ile Asp Val Phe Val Gly Gly
        530                 535                 540

Leu Ser Glu Gln Pro Thr Lys Gly Ser Leu Leu Gly Pro Thr Phe Ala
545                 550                 555                 560

Cys Leu Phe Ala His Gln Met Ala Gln Thr Lys Arg Gly Asp Arg Phe
            565                 570                 575

Trp Tyr Glu Asn Phe Val Ser Pro Ser Ala Phe Thr Val Asp Gln Ile
            580                 585                 590

Asp Glu Ile Arg Lys Thr Thr Met Ala Arg Ile Ile Cys Asp Asn Thr
        595                 600                 605

Asp Thr Val Thr His Val Gln His His Ala Phe Ser Leu Pro Asp Asp
610                 615                 620

Tyr Gly Asn Cys Pro Leu Ser Cys Asn Ser Thr Gly Ile Ile Gln Val
625                 630                 635                 640

Phe Asp Pro Lys Ala Phe Lys Asp Glu Glu Lys Leu Thr Ser Leu Pro
            645                 650                 655

Ile Thr Lys Glu Thr Val Glu Lys Val Ile Arg Leu Gly Leu Arg Gln
            660                 665                 670

Trp Gln Arg Tyr Glu Glu Gly Glu Gly Arg Arg Ile Ser Ala Gln Leu
        675                 680                 685

Ser Asp Ser Ser Pro Ser Ala Leu Leu Ser His Ala Leu Leu Met Ala
        690                 695                 700

Pro Lys Lys Glu Ser Ile Asp Ile Ala Arg Thr Ala Ser Val Leu Arg
705                 710                 715                 720

Glu Ala Thr Asn Ile Leu Ile Ser Gly Asn Gly Leu Asp Lys Asp Glu
            725                 730                 735

Arg Leu Pro Asp Leu Asp Ile Gly Thr Leu Gln Lys Ile Leu Pro Gln
            740                 745                 750

```
Ile Asp Val Gly Ser Val Ile Gly Asn Phe Thr Pro Phe Leu Ala Arg
            755                 760                 765
Asp Pro Leu Pro Lys Glu Gln Cys Leu Pro Glu Pro Leu Pro Cys Asp
            770                 775                 780
His Thr Ser Lys Tyr Arg Thr Tyr Ser Gly Trp Cys Asn Asn Leu Lys
785                 790                 795                 800
Asn Pro Lys Phe Gly Asn Ala Phe Thr Gln Met Arg Arg Leu Leu Asp
            805                 810                 815
Pro Ala Tyr Asp Asp Gly Phe Asp Thr Pro Arg Thr Arg Ser Val Leu
            820                 825                 830
Gly Ser Glu Leu Pro Ser Ala Arg Lys Ile Ser Asn Ile Val His Ser
            835                 840                 845
Asp Ala Pro Lys Phe His Val Lys Phe Thr His Met Leu Met Gln Phe
            850                 855                 860
Gly Gln Ile Leu Asp His Asp Met Met His Ser Pro Ile Ser Arg Gly
865                 870                 875                 880
Pro Lys Asn Thr Ile Leu Asn Cys Ser Ser Cys Asp Ser Ala Gln Thr
            885                 890                 895
Leu Ser Ile His Cys Phe Pro Ile Lys Ile Glu Ala Asn Asp Pro Phe
            900                 905                 910
Phe Pro Ser Lys His Ser Asp Gly Arg Pro Arg Cys Met Pro Phe Ala
            915                 920                 925
Arg Ser Leu Leu Ala Gln Val Ser Leu Gly Phe Arg Asn Gln Leu Asn
            930                 935                 940
Gln Leu Thr Ser Phe Leu Asp Ala Ser Thr Ile Tyr Gly Ser Thr Gln
945                 950                 955                 960
Cys Glu Ala Asn Lys Leu Arg Leu Phe Ser Gly Lys Leu Asn Phe
            965                 970                 975
Thr Asp Leu Gly Phe Asn Lys Glu Ala Leu Pro Gln Gly Asn Gln Glu
            980                 985                 990
Arg Asp Cys Arg Ser Val Leu Gln Asn Arg Gln Arg Arg Cys Phe Val
            995                1000                1005
Ala Gly Asp Glu Arg Ser Asn Glu Gln Pro Gly Leu Thr Ala Ile
            1010               1015               1020
His Asn Ile Phe Leu Arg Glu His Asn Arg Ile Ala Arg Tyr Leu
            1025               1030               1035
Lys Gln Ile Asn Asn Phe Trp Ser Asp Glu Lys Leu Phe Gln Glu
            1040               1045               1050
Ser Arg Arg Ile Asn Ile Ala Gln Leu Gln His Ile Ile Tyr Lys
            1055               1060               1065
Glu Trp Leu Pro Val Val Leu Gly Cys Gln Asn Met Glu Lys Trp
            1070               1075               1080
Gly Leu Met Pro Gln Thr Ala Gly Tyr Phe Glu Gly Tyr Asp Asp
            1085               1090               1095
Gln Cys Asp Ala Thr Ile Ser Gln Glu Met Ser Thr Ser Ala Phe
            1100               1105               1110
Arg Phe Gly His Ser Leu Ile Arg Gly Val Phe Thr Arg Met Asn
            1115               1120               1125
Asp Asn Phe Gln Asn Met Thr Asn His Val Asn Leu Thr Glu Thr
            1130               1135               1140
Phe Ser Asn Pro Ser Pro Val Tyr Asp Lys Asn Ser Gly His Met
            1145               1150               1155
Glu Ser Ile Leu Met Gly Leu Ile Gly Ala Asn Ser Met Ala Phe
```

```
                1160                1165                1170

Asp Arg His Ile Val Thr Ala Val Arg Asn His Leu Phe Ala Lys
    1175                1180                1185

Pro Gly Gly Pro Leu Thr Gly Leu Asp Leu Pro Ala Val Asn Ile
    1190                1195                1200

Gln Arg Gly Arg Asp His Gly Val Gln Gly Tyr Asn Ala Tyr Arg
    1205                1210                1215

Lys His Cys Gly Leu Arg Lys Ala Ser Ala Phe Ser Asp Leu Arg
    1220                1225                1230

Asp Val Met Asn Ser Glu Ala Val Thr Ala Leu Glu Thr Ala Tyr
    1235                1240                1245

Ala His Val Asp Asp Ile Asp Leu Phe Pro Gly Ile Met Ser Glu
    1250                1255                1260

Ser Pro Thr Arg Gly Ser Leu Val Gly Pro Thr Leu Ala Cys Leu
    1265                1270                1275

Ile Gly Glu Gln Met Gln Arg Leu Lys Lys Cys Asp Arg Phe Tyr
    1280                1285                1290

Tyr Glu Thr Ser Asp Ser Met Val Arg Phe Thr Pro Asp Gln Leu
    1295                1300                1305

Val Glu Ile Arg Lys Ala Ser Leu Ser Arg Ile Ile Cys Asp Asn
    1310                1315                1320

Ser Glu Tyr Ala Ala Asn Ile Gln Pro Asn Val Phe Leu Met Pro
    1325                1330                1335

Asp Asp Leu Thr Asn Ser Pro Met Thr Cys Ser Glu Leu Ser Glu
    1340                1345                1350

Ile Asp Leu Asn Lys Trp Val Glu Arg Asp Tyr Cys Leu Val Asp
    1355                1360                1365

Glu Arg Val Val Asn Arg Gly Lys Thr Lys Arg Ile Thr Pro Cys
    1370                1375                1380

Ile Thr Cys Thr Cys Thr Leu Glu Gly Pro Glu Cys His Ser Ile
    1385                1390                1395

Thr Ile Asp Asp Cys Ser Arg Leu Leu Arg Asp Tyr Ser Ile Thr
    1400                1405                1410

Asp Ile Gln Lys Asp Pro Val Cys Leu Ile Gln Cys Ser Gln Gln
    1415                1420                1425

Leu Lys Lys Leu
    1430

<210> SEQ ID NO 15
<211> LENGTH: 631
<212> TYPE: PRT
<213> ORGANISM: Arabidopsis reductase

<400> SEQUENCE: 15

Met Gly Phe Ser Pro Ser Ser Trp Phe Leu His Pro Gln Leu His
1               5                   10                  15

His Val Val Ser Lys Met Ser Tyr Phe Asp Ala Phe Leu Phe Tyr Ile
                20                  25                  30

Val His Leu Val Asp Lys Leu Gly Leu Trp His Arg Phe Pro Val Leu
            35                  40                  45

Leu Gly Val Ala Tyr Leu Gly Leu Arg Arg His Leu His Gln Arg Tyr
        50                  55                  60

Asn Leu Val His Val Gly Pro Ile Asn Gly Gln Gly Tyr Asp Thr Asp
65                  70                  75                  80

Glu Phe Cys Tyr Arg Thr Ala Asp Gly Lys Cys Asn His Pro Ser Asp
```

```
                    85                  90                  95
Asn Thr Ile Gly Ser Gln Gly Ser Phe Ile Gly Arg Asn Met Pro Pro
                100                 105                 110
Ser Thr Ser Gln Tyr Gly Ile Leu Asp Pro His Pro Ser Val Val Ala
                115                 120                 125
Thr Lys Leu Leu Ala Arg Lys Arg Phe Ile Asp Asn Gly Asp Gln Phe
            130                 135                 140
Asn Val Ile Ala Cys Ser Trp Ile Gln Phe Met Ile His Asp Trp Val
145                 150                 155                 160
Asp His Leu Glu Asp Thr His Gln Ile Glu Leu Glu Ala Pro Glu Glu
                165                 170                 175
Val Ala Ser Gly Cys Pro Leu Lys Ser Phe Lys Phe Leu Arg Thr Lys
                180                 185                 190
Lys Val Pro Thr Asp Asp His His Lys Ser Gly Ala Val Asn Thr Arg
                195                 200                 205
Thr Pro Trp Trp Asp Gly Ser Val Ile Tyr Gly Asn Asp Glu Thr Gly
                210                 215                 220
Met Arg Arg Val Arg Val Phe Lys Asp Gly Lys Leu Lys Ile Ser Gly
225                 230                 235                 240
Asp Gly Leu Leu Glu Arg Asp Glu Arg Gly Val Pro Ile Ser Gly Asp
                245                 250                 255
Ile Arg Asn Ser Trp Ser Gly Phe Ser Leu Leu Gln Ala Leu Phe Val
                260                 265                 270
Lys Glu His Asn Ser Val Cys Asp Met Leu Lys Glu Arg Tyr Pro Asp
                275                 280                 285
Phe Asp Asp Glu Lys Leu Tyr Arg Thr Ala Arg Leu Val Thr Ala Ala
        290                 295                 300
Val Ile Ala Lys Val His Thr Ile Asp Trp Thr Ile Glu Leu Leu Lys
305                 310                 315                 320
Thr Asp Thr Leu Thr Ala Gly Met Arg Ile Asn Trp Tyr Gly Phe Phe
                325                 330                 335
Gly Lys Lys Val Lys Asp Met Val Gly Ala Arg Phe Gly Pro Leu Phe
                340                 345                 350
Ser Gly Leu Val Gly Leu Lys Lys Pro Asn Asp His Gly Val Pro Tyr
                355                 360                 365
Ser Leu Thr Glu Glu Phe Val Ser Val Tyr Arg Met His Cys Leu Leu
            370                 375                 380
Pro Glu Thr Leu Ile Leu Arg Asp Met Asn Ser Glu Asn Val Asp Lys
385                 390                 395                 400
Glu Asn Pro Ala Ile Glu Arg Glu Ile Pro Met Thr Glu Leu Ile Gly
                405                 410                 415
Lys Lys Ala Gly Glu Lys Ala Ser Lys Leu Gly Phe Glu Gln Leu Leu
                420                 425                 430
Val Ser Met Gly His Gln Ser Cys Gly Ala Leu Thr Leu Trp Asn Tyr
            435                 440                 445
Pro Asn Trp Met Arg Asn Leu Val Ala Gln Ile Asp Gly Glu Asp
450                 455                 460
Arg Pro His Leu Ile Asp Met Ala Ala Leu Glu Ile Tyr Arg Asp Arg
465                 470                 475                 480
Glu Arg Gly Val Pro Arg Tyr Asn Glu Phe Arg Lys Asn Leu Leu Met
                485                 490                 495
Ser Pro Ile Ser Lys Trp Glu Glu Leu Thr Asp Asp Glu Glu Ala Ile
                500                 505                 510
```

-continued

```
Lys Val Leu Arg Glu Val Tyr Glu Asp Asp Ile Glu Lys Leu Asp Leu
            515                 520                 525

Asn Val Gly Leu His Ala Glu Lys Lys Ile Lys Gly Phe Ala Ile Ser
530                     535                 540

Glu Thr Ala Phe Phe Ile Phe Leu Leu Val Ala Ser Arg Arg Leu Glu
545                 550                 555                 560

Ala Asp Arg Phe Phe Thr Thr Asn Phe Asn Glu Lys Thr Tyr Thr Lys
                565                 570                 575

Glu Gly Leu Glu Trp Val Asn Thr Thr Glu Thr Leu Lys Asp Val Ile
            580                 585                 590

Asp Arg His Phe Pro Arg Leu Thr Asp Gln Trp Met Arg Cys Ser Ser
            595                 600                 605

Ala Phe Ser Val Trp Gly Ser Asp Pro Asn Pro Lys Asn Trp Val Pro
            610                 615                 620

Leu Tyr Leu Arg Ser Ala Pro
625                 630

<210> SEQ ID NO 16
<211> LENGTH: 12
<212> TYPE: DNA
<213> ORGANISM: Drosophila melanogaster

<400> SEQUENCE: 16
cctaggtgag tt                                                         12

<210> SEQ ID NO 17
<211> LENGTH: 17
<212> TYPE: DNA
<213> ORGANISM: Drosophila melanogaster

<400> SEQUENCE: 17
tttgaaactc agctagc                                                    17

<210> SEQ ID NO 18
<211> LENGTH: 14
<212> TYPE: DNA
<213> ORGANISM: Drosophila melanogaster
<220> FEATURE:
<221> NAME/KEY: misc_feature
<222> LOCATION: (9)..(9)
<223> OTHER INFORMATION: n is a, c, g, or t

<400> SEQUENCE: 18
tttyyyytnc agrt                                                       14
```

US 8,735,371 B2

COMPOSITIONS AND METHODS FOR ALTERING RNAI

CROSS REFERENCE TO RELATED APPLICATIONS

This invention is a continuation of U.S. patent application Ser. No. 11/641,937, filed Dec. 19, 2006, which claims priority to U.S. Provisional Patent Application No. 60/751,596, filed Dec. 19, 2005, each of which are herein incorporated by reference.

STATEMENT REGARDING FEDERAL FUNDING

This invention was made with government support under Grant No. R01 GM068743 awarded by the National Institutes of Health. The government has certain rights in the invention.

FIELD OF THE INVENTION

The present invention relates to compositions and methods for altering (e.g., enhancing) RNAi. In particular, the present invention provides systems and methods for identifying regulators of RNAi. For example, the present invention provides RNAi regulators (e.g., HPS1 and HPS4) and methods of altering (e.g., inhibiting) these regulators in order to alter (e.g., enhance) RNAi. The present invention also provides methods of identifying inhibitors (e.g., small molecule, nucleic acid (e.g., siRNA), and antibody) of RNAi regulators and methods of using the same (e.g., to enhance RNAi). Compositions and methods of the present invention find use in research (e.g., functional genomics), therapeutic (e.g., drug discovery and delivery) and clinical applications.

BACKGROUND OF THE INVENTION

RNA interference (RNAi) is a natural mechanism in which RNA regulates gene expression. When RNA is utilized by the RNAi mechanism, it alters (e.g., represses or silences) the expression of genes that are complementary in sequence to the regulatory RNA (See, e.g., Nakahara and Carthew, (2004) Curr Opin Cell Biol 16, 127-133). Generally, gene repression occurs via degradation of complementary mRNA transcripts, thus preventing protein product synthesis (See, e.g., Carthew (2001) Curr Opin Cell Biol 12, 244-248). A signature feature of the regulatory RNA is that it has a double helix structure. If double stranded RNA (dsRNA) is present, then it is processed into small RNA fragments 21-25 nucleotides in length by a class of RNaseIII enzymes called the Dicer family. These RNA fragments, called siRNAs, are sufficient to substitute for dsRNA in causing mRNA transcript degradation. Thus, siRNAs are thought to be the direct guides that identify mRNA substrates for degradation.

Once siRNAs are formed, they associate into a nuclease complex termed RNA-induced silencing complex (RISC) that recognizes and cleaves mRNAs. Cleavage of mRNA substrate by RISC is endonucleolytic and occurs at a central site in the region homologous to the siRNA.

RNAi has become a new and powerful approach to rational drug design (e.g., to treat diseases that involve aberrant gene expression). However, one significant drawback to RNAi is that its effect on gene expression is rarely completely potent. This limitation, observed widely, is problematic when a cessation of gene expression is desired or required. Thus, there exists a need to improve RNAi efficacy in research, clinical and therapeutic settings (e.g., to improve RNA-based treatments).

SUMMARY OF THE INVENTION

The present invention relates to compositions and methods for altering (e.g., enhancing) RNAi. In particular, the present invention provides systems and methods for identifying regulators of RNAi. For example, the present invention provides RNAi regulators (e.g., HPS1 and HPS4) and methods of altering (e.g., inhibiting) these regulators in order to alter (e.g., enhance) RNAi. The present invention also provides methods of identifying inhibitors (e.g., small molecule, nucleic acid (e.g., siRNA), and antibody) of RNAi regulators and methods of using the same (e.g., to enhance RNAi). Compositions and methods of the present invention find use in research (e.g., functional genomics), therapeutic (e.g., drug discovery and delivery) and clinical applications.

Accordingly, in some embodiments, the present invention provides a method of altering RNAi in a cell comprising administering to the cell a RNAi regulator inhibitor. In some embodiments, the RNAi regulator is HPS1 or similar agent. In some embodiments, the RNAi regulator is HPS4 or similar agent. In some embodiments, the RNAi regulator is CG6969 or similar agent. In some embodiments, the administering enhances RNAi in the cell. In some embodiments, the inhibitor is siRNA. The present invention is not limited by the type of inhibitor utilized. In some embodiments, the inhibitor is an antibody. In some embodiments, the inhibitor is a small molecule. In some embodiments, the inhibitor is dsRNA. In some embodiments, the inhibitor is shRNA. In some embodiments, the inhibitor is co-administered with a siRNA and/or miRNA specific for an aberrantly expressed gene or gene to be regulated within the cell. The present invention is not limited by the type of aberrantly expressed gene or gene to be regulated. Indeed, the expression of a variety of aberrantly expressed genes or genes to be regulated are contemplated to be treatable (e.g., lowered) using the compositions and methods of the present invention. Examples of aberrantly expressed genes include, but are not limited to, oncogenes, genes expressed by pathogenic organisms (e.g., viruses, bacteria, fungi, etc.), and other aberrantly expressed genes. A variety of oncogenes are contemplated to be suppressable including, but not limited to, abl, Bcl-2, Bcl-x1, erb, brca1, brca2, fms, gsp, hst, jun, myc, neu, raf, ras, ret, src, and trk. The present invention also contemplates that the aberrantly expressed gene may be a viral gene (e.g., any gene necessary for viral survival within a host, for example, that can silenced using the compositions and methods of the present to inhibit viral growth or replication). In some embodiments, the aberrantly expressed gene is a viral gene. In some embodiments, the cell is in vitro. In some embodiments, the cell is in vivo. In some embodiments, the inhibitor blocks expression of the RNAi regulator. In some embodiments, the inhibitor alters (e.g., decreases) the activity of the RNAi regulator. In some embodiments, administrating the inhibitor increases the rate of RISC assembly. In some embodiments, administrating the inhibitor increases RISC activity.

The present invention also provides a method of identifying an inhibitor of a RNAi regulator comprising: providing cells comprising the RNAi regulator; administering to the cells a test compound; and characterizing the ability of the test compound to alter the RNAi regulator. In some embodiments, altering the RNAi regulator inhibits expression of the RNAi regulator. In some embodiments, altering the RNAi regulator inhibits activity of the RNAi regulator. In some embodiments, the test compound is an RNA. In some embodiments, the RNA is a siRNA. In some embodiments, the RNA is a dsRNA. In some embodiments, the RNA is a shRNA. The present invention is not limited to any particular type of test compound. Indeed a variety of test compounds are contemplated to be useful in the present invention including, but not limited to, antibodies, small molecules, peptides, and peptoids. In some embodiments, the RNAi regulator is HPS1. In some embodiments, the RNAi regulator is HPS4.

The present invention also provides a method of increasing the rate of RNA-induced silencing complex (RISC) assembly in a cell comprising administering to the cell an RNAi regulator inhibitor. In some embodiments, the RNAi regulator is HPS1, HPS4 and/or CG6969. In some embodiments, the present invention provides a composition comprising a RNAi regulator or a mutant thereof (e.g., described herein) and/or nucleic acid sequence encoding the same.

DESCRIPTION OF THE DRAWINGS

FIG. 6 shows (A) the structure of the CG4966 gene. Two mRNA isoforms are generated by alternate promoter use. The isoforms only differ by the identities of their first exons, which contain 5'UTR and early coding sequence. The resulting protein products from each isoform differ in length (834 vs 858 amino acids) due to sequence differences at the amino-termini; (B) Domain structure of the B isoform of CG4966 showing the positions of nonsense mutations isolated from the genetic screen. Amino acid identity and positions are noted; all were mutated into Stop codons (X). Domains at amino and carboxy termini are shown in black and grey rectangles, respectively. These domains are completely shared between the A and B isoforms; (C) Structures of vertebrate orthologs of CG4966, showing conserved domains and the percent amino acid sequence identity between each ortholog and CG4966. Lengths of vertebrate orthologs are given in amino acids (aa)

FIG. 14 shows *drosophila* HPS4 cDNA sequence isoform RB (SEQ ID NO.:1).

FIG. 15 shows *drosophila* HPS4 cDNA sequence isoform RA (SEQ ID NO.:2).

FIG. 16 shows *drosophila* HPS1 cDNA sequence (SEQ ID NO.:3).

FIG. 17 shows the cDNA sequence of human HPS1 (SEQ ID NO.:4) and human HPS4 (SEQ ID NO.:5).

FIGS. 22A-J show CG6969 codon sequence (SEQ ID NO.: 6) and ortholog sequences (SEQ ID NOs.: 7-15). Predicted ORF sequences of CG6969 (A), human thyroid peroxidase (B), human eosinophil peroxidase (C), human myeloid peroxidase (D), human lymphoid peroxidase (E), murine myeloid peroxidase (F), mosquito peroxidase (G), canine myeloid peroxidase (H), *C. elegans* peroxidase (I), *Arabidopsis* oxidoreductase (J). The amino acids denoted with a box in (A) are those that are altered in the two RNAi-enhancing mutant alleles.

FIGS. 25A-D show CLUSTALW alignment of CG6969 (SEQ ID NO.: 6) and ortholog sequences shown as mosquito (SEQ ID NO.: 12), MPO (human) (SEQ ID NO.: 9), MPO (dog) (SEQ ID NO.: 13), MPO (mouse) (SEQ ID NO.: 11), EPX (human) (SEQ ID NO.: 8), LPO (human) (SEQ ID NO.: 10), TPO (human) (residues 1-800 of SEQ ID NO.: 7), *C. elegans* (residues 547-1432 of SEQ ID NO.: 14), and *Arabidopsis* (SEQ ID NO.: 15). Strong identity at a position is indicated with an asterisk; moderate identity is indicated with a colon; strong similarity with a period. The tyrosine residue that is altered to a stop codon in one mutant allele is highlighted. The glycine residue that is altered to a threonine in the other mutant allele is highlighted by a grey box.

DEFINITIONS

Figure 1:
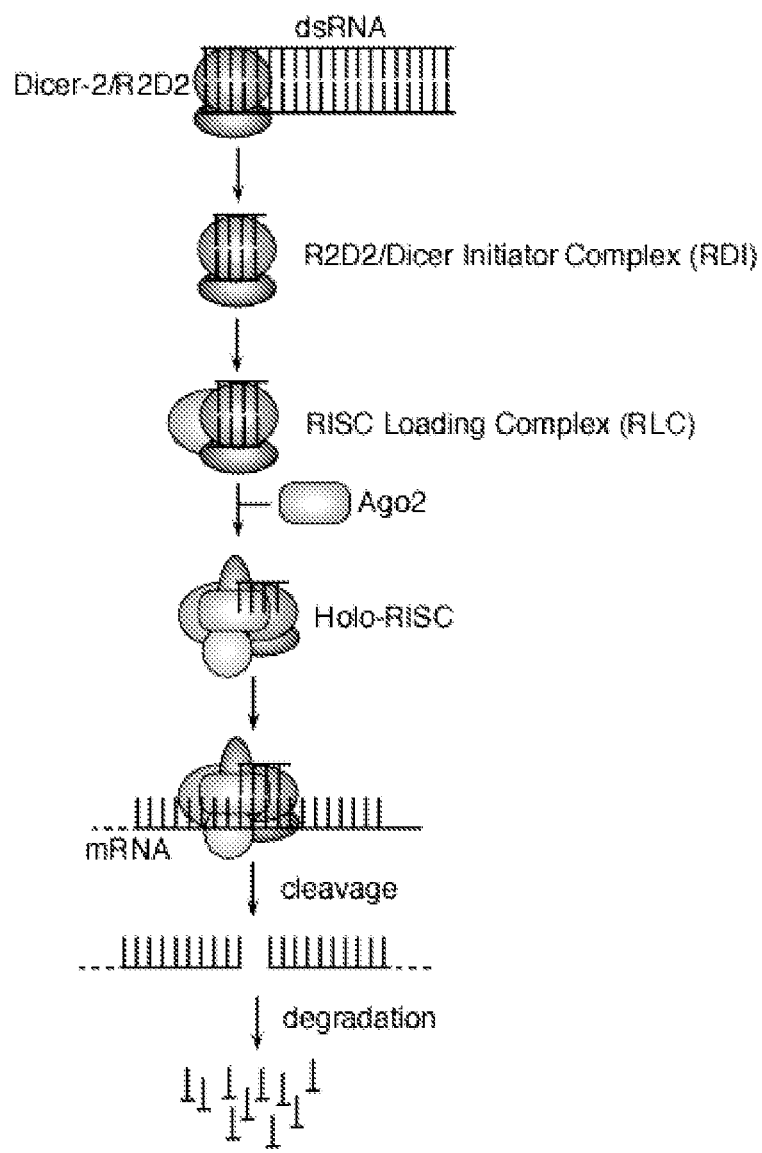
FIG. 1 shows the RNAi pathway wherein Dicer associated with R2D2 protein processes siRNA precursors, resulting RDI complex initiating siRNA assembly into RISC, and holo-RISC cleaving complementary mRNA, leading to its degradation.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (e.g., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (e.g., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the terms "specifically binding to HPS4 with low background binding" and "specifically binding to HPS1 with low background binding" refer to an antibody that binds specifically to HPS4 or HPS1 protein, respectively (e.g., in an immunohistochemistry assay) but not to other proteins (e.g., lack of non-specific binding).

As used herein, the term "subject" refers to any plant or animal (e.g., a mammal), including, but not limited to, humans, non-human primates, rodents, and the like, which is to be the recipient of a particular treatment. Typically, the terms "subject" and "patient" are used interchangeably herein in reference to a human subject, unless indicated otherwise herein.

As used herein, the terms "reagent(s) capable of specifically detecting HPS4 expression" and "reagent(s) capable of specifically detecting HPS1 expression" refer to reagents used to detect the expression of HPS4 and HPS1, respectively. Examples of suitable reagents include but are not limited to, nucleic acid probes capable of specifically hybridizing to HPS4 or HPS1 mRNA or cDNA, and antibodies (e.g., monoclonal or polyclonal antibodies of the present invention).

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "transgene" refers to a heterologous gene that is integrated into the genome of an organism (e.g., a non-human animal) and that is transmitted to progeny of the organism during sexual reproduction.

As used herein, the term "transgenic organism" refers to an organism (e.g., a non-human animal) that has a transgene integrated into its genome and that transmits the transgene to its progeny during sexual reproduction.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (e.g., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.1% SDS, 5×Denhardt's reagent (50×Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention can be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 (1989)).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 (1989)).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA can be quantified; other minor species of RNA which hybridize to the transgene probe are generally not considered in the quantification of the expression of the transgenic mRNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk—cell lines, the CAD gene that is used in conjunction with CAD-deficient cells and the mammalian hypoxanthine-guanine phosphoribosyl transferase (hprt) gene that is used in conjunction with hprt—cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to alter a RNAi regulator of the present invention. Such test compounds may function to alter a RNAi regulator, for example, by binding to proteins that generated a RNAi regulator, altering (e.g., inhibiting) RNAi regulator expression, altering (e.g., inhibiting) RNAi regulator activity or RNAi regulator presence, or have a stimulatory or inhibitory effect on, for example, the expression or activity of a RNAi regulator substrate. Test compounds comprise both known and potential therapeutic compounds. A test compound can be determined to be useful (e.g., therapeutically or for research purposes) by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

The term "RNA interference" or "RNAi" refers to the silencing or decreasing of gene expression (e.g., using siRNAs and/or miRNAs). Thus, RNAi refers to the process of sequence-specific, post-transcriptional gene silencing in animals and plants, initiated by siRNA and/or miRNA sharing homology in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the inhibition of function of the target RNA may be complete or partial.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures.

As used herein, the terms "microRNA" and "miRNA" refer to a class of gene regulatory small RNAs, typically 21-23 nt in length, that are evolutionarily conserved, small non-coding RNA molecules found in eukaryotes. miRNAs have been implicated in a wide range of functions such as cell growth and apoptosis, development, neuronal plasticity and remodeling, viral infection processes, oncogenesis, and even insulin secretion. miRNAs have also been implicated in disease (e.g., an overabundance of miRNA has been reported in cases of Fragile X Mental Retardation, whereas some cancers are associated with up- and downregulation of certain miRNA genes).

The term "target RNA molecule" refers to an RNA molecule to which at least one strand of the short double-stranded region of an siRNA is homologous or complementary or to which a miRNA possesses homology for. Typically, when such homology or complementary is about 100%, the siRNA and/or miRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA sequences.

The term "RNA function" refers to the role of an RNA molecule in a cell. For example, one function of mRNA is translation into a protein. Other RNAs are not translated into a protein, and have other functions; such RNAs include but are not limited to transfer RNA (tRNA), ribosomal RNA (rRNA), and small nuclear RNAs (snRNAs). An RNA molecule may have more than one role in a cell.

The term "inhibition" when used in reference to gene expression or RNA function refers to a decrease in the level of gene expression or RNA function as the result of some interference with or interaction with gene expression or RNA function as compared to the level of expression or function in the absence of the interference or interaction. The inhibition may be complete, in which there is no detectable expression or function, or it may be partial. Partial inhibition can range from near complete inhibition to near absence of inhibition; typically, inhibition is at least about 50% inhibition, or at least about 80% inhibition, or at least about 90% inhibition.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, miRNA binding sites, termination signals, etc.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap, Plant Mol. Biol. 24:119-127 (1994)) promoters. Such promoters have been used successfully to direct the expression of heterologous nucleic acid sequences in transformed plant tissue.

In contrast, a "regulatable" or "inducible" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (e.g., the first and second genes can be from the same species, or from different species).

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual*, 2nd ed., Cold Spring Harbor Laboratory Press, New York (1989) pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "vector" refers to nucleic acid molecules that transfer DNA segment(s) from one cell to another. The term "vehicle" is sometimes used interchangeably with "vector." A vector may be used to transfer an expression cassette into a cell; in addition or alternatively, a vector may comprise additional genes, including but not limited to genes which encode marker proteins, by which cell transfection can be determined, selection proteins, be means of which transfected cells may be selected from non-transfected cells, or reporter proteins, by means of which an effect on expression or activity or function of the reporter protein can be monitored.

The term "expression cassette" refers to a chemically synthesized or recombinant DNA molecule containing a desired coding sequence and appropriate nucleic acid sequences necessary for the expression of the operably linked coding sequence either in vitro or in vivo. Expression in vitro includes expression in transcription systems and in transcription/translation systems. Expression in vivo includes expression in a particular host cell and/or organism. Nucleic acid sequences necessary for expression in prokaryotic cell or in vitro expression system usually include a promoter, an operator (optional), and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases, referred to as a transcription template in the art, include a template DNA strand which has a polymerase promoter region followed by the complement of the RNA sequence desired. In order to create a transcription template, a complementary strand is annealed to the promoter portion of the template strand.

The term "expression vector" refers to a vector comprising one or more expression cassettes. Such expression cassettes include those of the present invention, where expression results in an siRNA transcript.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, bacterial infection, viral infection, biolistics (i.e., particle bombardment) and the like. The terms "transfect" and "transform" (and grammatical equivalents, such as "transfected" and "transformed") are used interchangeably.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

The term "host cell" refers to any cell capable of replicating and/or transcribing and/or translating a heterologous gene. Thus, a "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "antisense" when used in reference to DNA refers to a sequence that is complementary to a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "ds siRNA" refers to a siRNA molecule that comprises two separate unlinked strands of RNA which form a duplex structure, such that the siRNA molecule comprises two RNA polynucleotides.

The terms "hairpin siRNA" and "small hairpin RNA" and "shRNA" refer to a siRNA molecule that comprises at least one duplex region where the strands of the duplex are connected or contiguous at one or both ends, such that the siRNA molecule comprises a single RNA polynucleotide. The antisense sequence, or sequence which is complementary to a target RNA, is a part of the at least one double stranded region. Such "shRNA" may be a "full hairpin siRNA" that comprises a duplex or double stranded region of about 18-29 base pairs long, where the two strands are joined at one end by a linking sequence, or loop. At least one strand of the duplex region is an antisense strand, and either strand of the duplex region may be the antisense strand. The region linking the strands of the duplex, also referred to as a loop, may comprise one or more nucleotides (e.g., three nucleotides). The sequence of the loop may also a part of the antisense strand of the duplex region, and thus is itself complementary to a target RNA molecule. The "shRNA" may also be a "partial hairpin siRNA" comprising an antisense sequence (or a region or strand complementary to a target RNA) of about 18-25 bases long, and which forms less than a full hairpin structure with the antisense sequence. In some embodiments, the antisense sequence itself forms a duplex structure of some or most of the antisense sequence. In other embodiments, the siRNA comprises at least one additional contiguous sequence or region, where at least part of the additional sequence(s) is complementary to part of the antisense sequence.

The term "mismatch" when used in reference to siRNAs refers to the presence of a base in one strand of a duplex region of which at least one strand of an siRNA is a member, where the mismatched base does not pair with the corresponding base in the complementary strand, where pairing is determined by the general base-pairing rules. The term "mismatch" also refers to the presence of at least one additional base in one strand of a duplex region of which at least one strand of an siRNA is a member, where the mismatched base does not pair with any base in the complementary strand, or to a deletion of at least one base in one strand of a duplex region which results in at least one base of the complementary strand being without a base pair. A mismatch may be present in either the sense strand, or antisense strand, or both strands, of an siRNA. If more than one mismatch is present in a duplex region, the mismatches may be immediately adjacent to each other, or they may be separated by from one to more than one nucleotide. Thus, in some embodiments, a mismatch is the presence of a base in the antisense strand of an siRNA which does not pair with the corresponding base in the complementary strand of the target siRNA. In other embodiments, a mismatch is the presence of a base in the sense strand, when present, which does not pair with the corresponding base in the antisense strand of the siRNA. In yet other embodiments, a mismatch is the presence of a base in the antisense strand that does not pair with the corresponding base in the same antisense strand in a foldback hairpin siRNA.

The terms "nucleotide" and "base" are used interchangeably when used in reference to a nucleic acid sequence.

The term "strand selectivity" refers to the presence of at least one mismatch in either an antisense or a sense strand of a siRNA molecule. The presence of at least one mismatch in an antisense strand results in decreased inhibition of target gene expression.

The term "cellular destination signal" is a portion of an RNA molecule that directs the transport of an RNA molecule out of the nucleus, or that directs the retention of an RNA molecule in the nucleus; such signals may also direct an RNA molecule to a particular subcellular location. Such a signal may be an encoded signal, or it might be added post-transcriptionally.

As used herein, the term "RNAi regulator" refers to the nucleic acid (e.g., mRNA, DNA, etc.) and amino acid sequence of a protein capable of altering RNAi identified by the systems and methods of the present invention (e.g., HPS1 and HPS4). RNAi regulators comprise genes and proteins capable of altering (e.g., restricting, limiting, suppressing or enhancing) RNAi within a cell.

As used herein, the terms "host," "subject" and "patient" refer to any animal, including but not limited to, human and non-human animals (e.g. rodents, arthropods, insects (e.g., Diptera), fish (e.g., zebrafish), non-human primates, ovines, bovines, ruminants, lagomorphs, porcines, caprines, equines, canines, felines, ayes, etc.), that is studied, analyzed, tested, diagnosed or treated. As used herein, the terms "host," "subject" and "patient" are used interchangeably, unless indicated otherwise herein.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "effective amount" refers to the amount of a composition (e.g., comprising a an RNAi regulator inhibitor) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, test compound or other agent, or therapeutic treatment (e.g., compositions of the present invention) to a cell or subject (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), oral mucosa (buccal), ear, rectal, by injection (e.g., intravenously, subcutaneously, intratumorally, intraperitoneally, etc.) and the like.

As used herein, the terms "co-administration" and "co-administering" refer to the administration of at least two agent(s) (e.g., composition comprising an RNAi regulator inhibitor (e.g., siRNA) and one or more other agents—e.g., a non-RNAi regulator siRNA) or therapies to a cell or subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

DETAILED DESCRIPTION OF THE INVENTION

RNAi provides a powerful approach to rational drug design. For example, a multitude of diseases that involve aberrant gene expression may benefit from RNA-based compounds used as therapeutics. To date, many researches have utilized RNAi in multiple applications (e.g., as a tool for functional genomics). RNAi also holds great potential in therapeutic and clinical applications (e.g., in drug development and therapeutic treatments). However, one significant drawback to RNAi is that its effect on gene expression is rarely, if ever, completely potent. This limitation, observed widely, is problematic when a cessation of gene expression is desired or required. Thus, there exists a need to improve RNAi efficacy, and in the process create research and clinically useful products (e.g., research tools and therapeutics) that potentiate RNA-based treatments. Systems and methods that provide any level of enhancement in function find use (e.g., as an adjuvant) in a wide range of RNAi applications.

Rational design of therapeutic drugs against known molecular targets is a powerful means to develop effective treatment strategies for modern health. Rational design necessitates a detailed knowledge of target structure/function, which often limits this strategy. An RNA-based mechanism of gene regulation, RNA interference (RNAi), promises to become a radically new and powerful approach to rational drug design. Quite simply, for the multitude of diseases that involve aberrant gene expression, RNA-based compounds can be used as therapeutics. The advantages of this approach over other design approaches include, for example, simple nucleic acid based chemistry for drug synthesis; versatile delivery (e.g., local (e.g., gene vector or topical), or systemic (e.g., intravenous RNA or gene vector)); the ability to target any type of gene (e.g., pathogen-associated gene or endogenous gene (e.g., normal or mutant)) and combination of genes (e.g., multiplex); and extraordinary target specificity based on nucleic acid hybridization.

RNAi was discovered in 1998 as a gene silencing phenomenon in the roundworm Caenorhabditis elegans (See, e.g., Fire, et al., Nature 391, 806-811 (1998)). Later in 1998, it was established that RNAi exists in other species such as Drosophila melanogaster (See, e.g., Kennerdell and Carthew, Cell 95, 1017-1026 (1998)). A few years later, RNAi was discovered to be a potent process in mammals and humans (See, e.g., Elbashir et al., Nature 411, 494-498 (2001)).

Both large and small efforts to understand gene function have been aided by the ability to silence individual gene expression by RNAi. The potential for this type of application continues to grow. However, one of the biggest opportunities for RNAi as a technology application is in drug development. There are numerous examples where RNAi has been effective in cell-based models, including, but not limited to, for virus infection (e.g., including, but not limited to, HIV, SARS, Influenza, Hepatitis), cancer, macular degeneration, and hypercholesterolemia (See, e.g., Jacque et al., Nature 418, 435-438 (2002); Gitlin et al., Nature 418, 430-434 (2002); Brummelkamp et al., Cancer Cell 2, 243-7 (2002); Eskandarpour et al., Int J Cancer 115, 65-73 (2005); Soutschek et al., Nature 432, 173-8 (2004); Shankar et al., JAMA 293, 1367-73 (2005)). Recently, an animal model for hypercholesterolemia was effectively treated by intravenous injection of RNA-based drugs (See, e.g., Soutschek et al., Nature 432, 173-8 (2004)). Furthermore, several companies are actively testing RNA based drugs to treat human disease (e.g., macular degeneration). Thus, RNA can be used to treat a variety of human diseases and disorders.

However, one significant drawback to RNAi in many species, including humans, is that gene expression is rarely 100% repressed (See, e.g., Novina and Sharp, Nature 430, 161-4 (2004)). This limitation, observed widely, is problematic when a complete or nearly complete cessation of gene expression is desired or required. Clearly, for many research, agricultural, and therapeutic applications, partial gene silencing or low levels of silencing is unsatisfactory. Addressing the issue of RNAi performance in the marketplace necessitates addressing issues of RNAi efficacy. Thus, there exists a need to improve RNAi efficacy, and in the process create commercially useful and beneficial products that potentiate RNA-based treatments.

RNAi

RNAi is a widespread natural mechanism in which RNA regulates gene expression. When RNA is utilized by the RNAi mechanism, it represses or silences the expression of genes that are complementary in sequence to the regulatory RNA (See, e.g., Nakahara and Carthew, Curr Opin Cell Biol 16, 127-33 (2004)). Most often, gene repression occurs via degradation of complementary mRNA transcripts, thus preventing protein product synthesis (See, e.g., Carthew, et al., Curr Opin Cell Biol 13, 244-248 (2001)). A signature feature of the regulatory RNA is that it is in the form of a duplex. If double stranded RNA (dsRNA) is present, then it is processed into small RNA fragments, 21-25 nucleotides in length, by a class of RNaseIII enzymes called the Dicer family (SEE FIG. 1). Dicer enzymes cleave dsRNA molecules into fragments that are double-stranded, contain 5'-phosphorylated termini, and have 3' overhangs two nucleotides in length (See, e.g., Hannon, Nature 418, 244-251 (2002)). These RNA fragments, called short interfering (siRNAs), are sufficient to substitute for dsRNA in causing mRNA transcript degradation. Thus, siRNAs are thought to be the direct guides that identify mRNA substrates for degradation.

Once siRNAs are formed, they associate into a nuclease complex dubbed RNA-induced silencing complex (RISC) that recognizes and cleaves mRNAs (SEE FIG. 1). This ribonucleoprotein complex forms by a stepwise pathway in *Drosophila melanogaster* (See, e.g., Lee, et al. Cell 117, 83-94 (2004); Pham et al., Cell 117, 83-94 (2004)). First, siRNA associates with a heterodimer of the Dicer-2 and R2D2 proteins to form a RDI ternary complex. Second, unknown factors bind to this initiator complex to form the RISC-Loading Complex (RLC). Finally, the RLC is converted into the RNA-induced silencing complex (RISC), which is capable of binding and cleaving mRNA substrates. Conversion requires ATP and the protein Ago-2, which is also the RISC subunit directly responsible for mRNA target cleavage. The nascent siRNA is unwound during this step, and only one of the two strands is retained within RISC (See, e.g., Lee, et al. Cell 117, 83-94 (2004)). Although assembly requires these three steps, others may occur that are nevertheless not detected by current analyses. Assembly of RISC in other species, including human, likely occurs through similar mechanisms. For example, it has been shown that human Dicer forms similar complexes with siRNAs that potentially initiate RISC assembly (See, e.g., Pellino, et al., RNA 11(11): 1719-1724 (2005)).

Cleavage of mRNA substrate by RISC is endonucleolytic and occurs at a central site in the region homologous to the siRNA (SEE FIG. 1). Ago-2 catalyzes this reaction (See, e.g., Liu et al. Science 305, 1437-41 (2004); Song et al., Science 305, 1434-1437 (2004)) generating two mRNA fragments that are subsequently degraded. RISC is then able to bind and cleave other mRNA substrates with multiple turnover (See, e.g., Hutvagner et al., Science 297, 2056-2060 (2002)).

Numerous biological functions have been implicated for RNAi, including genome surveillance (e.g., the continual monitoring for expression of foreign genes and consequent silencing) (See, e.g., Carthew, et al., Curr Opin Cell Biol 13, 244-248 (2001)). As such, viruses may be a primary target for RNAi. RNAi has also been linked to suppression of transposon invasion in *C. elegans* and *D. melanogaster* (See, e.g., Ketting et al., Cell 99, 133-141 (1999); Ketting and Plasterk, Nature 404, 296-298 (2000); Pal-Bhadra et al., Mol Cell 9, 315-327 (2002)). In *C. elegans*, some RNAi-deficient strains are 'mutators' due to the increased mobility of endogenous transposons. RNAi also plays a role in the normal regulation of endogenous genes, which impacts on various cell and organism activities (See, e.g., Sontheimer and Carthew, Cell 122, 9-12 (2005)).

MicroRNAs (miRNAs) are also active in RNAi. miRNAs are evolutionarily conserved, small RNAs, typically 21-23 nt in length, that are non-coding RNA molecules found in eukaryotes. Although an understanding of the mechanism is not necessary to practice the present invention and the present invention is not limited to any particular mechanism of action, in some embodiments, miRNAs regulate gene expression post-transcriptionally at the level of translational inhibition at P-Bodies in the cytoplasm. In some embodiments, miRNAs guide mRNA cleavage similar to siRNAs. miRNA and various applications utilizing miRNA are described have been described (see, e.g., Carthew, Curr Opin Genet Dev. 2006 April; 16(2):203-8; Sarnow et al., Nat Rev Microbiol. 2006 September; 4(9):651-9; Calin and Croce, and Cancer Res. 2006 Aug. 1; 66(15):7390-4; Lee and Dutta, Curr Opin Investig Drugs. 2006 June; 7(6):560-4, each of which is hereby incorporated by reference in its entirety).

The use of either siRNAs or shRNAs or miRNAs holds great promise for research (e.g., to assay mammalian gene function) and therapeutic applications on a scale heretofore unimaginable. Yet, as described above, an inherent limitation to RNAi in many species is that typically, gene expression is only partially repressed (See, e.g., Novina and Sharp, Nature 430, 161-4 (2004)).

Systems and Methods of Identifying RNAi Regulators

One model system used is *Drosophila melanogaster*. This species has a powerful arsenal of genetic tools to discover gene function. Its RNAi mechanism is similar, if not identical, to mammalian RNAi. To date, every RNAi factor found in *Drosophila* has a similar function in mammalian RNAi. Finally, the most powerful biochemical assays for RNAi have been developed using extracts from *Drosophila* tissues. For all of these reasons, those of skill in the art appreciate that RNAi genes (e.g., genes involved in any of the stepwise processes of RNAi described above) in *Drosophila* can be identified and thoroughly characterized for use in understanding their mammalian counterparts.

Systems and methods utilized by the present invention to discover RNAi regulator genes have used saturation mutagenesis and find mutant variants (e.g., recessive mutants) that exhibit altered RNAi. A high-throughput screen that saturates the genome with mutations is contemplated to be an efficient and extensive means to identify such genes. A component for conducting this type of screen is the ability to induce a uniform RNAi response. Moreover, thousands of animals should be screened, which necessitates inducing RNAi on a large scale. In *Drosophila*, this limitation was overcome by enforced transcription of a double-stranded RNAi molecule, usually as an inverted repeat sequence that forms a hairpin structure in vivo (See, e.g., Kennerdell and Carthew, Nat Biotechnol 18, 896-898 (2000)). This concept can be adapted to mammalian cells using expression vectors that express short hairpin RNAs (shRNAs) (See, e.g., Miyagishi and Taira, Nat Biotechnol 20, 497-500 (2002); Paddison et al., Proc Natl Acad Sci USA 99, 1443-1448 (2002); Paul et al., Nat Biotechnol 20, 505-508 (2002)).

To target a reporter gene for RNAi, the white gene was chosen based on several criteria. The white gene encodes an ABC transporter required cell-autonomously to pigment the adult compound eye (See, e.g., Mackenzie et al., Genetica 108, 239-52 (2000)). A white$^+$ eye is dark red in color while a null white mutant is completely white. This phenotype is easily scored. Loss of white has no impact on viability or fertility. Finally, mutant alleles with reduced activity can be ordered by a phenotypic series: red, orange, white. A semi-quantitative relationship exists between expression level and phenotype such that partially reduced expression results in an intermediate phenotype (See, e.g., Mackenzie et al., Biochim Biophys Acta 1419, 173-85. (1999)). One exon of the white gene was repeated in a tail-to-tail orientation separated by an intron (See Example 1, and FIG. 3A). The tail-to-tail repeat was placed into a transformation vector and transformed into white$^+$ flies. Transformant lines with one copy of the white RNAi transgene exhibited an orange eye color (partial silencing), whereas transformants bearing two copies of the transgene were almost identical to white mutants (complete silencing) (See Example 1, FIG. 3B-E).

The screen is based on a strategy to create flies that are heterozygous but in which the compound eye is composed of cells homozygous mutant for one of the five major chromosomal arms (See, e.g., Lee, et al. Cell 117, 83-94 (2004)). The mutagenized flies also contained one copy of the white RNAi transgene. These flies ordinarily exhibit an orange eye color, due to partial silencing of white (See Example 1, FIG. 3D). Using the systems and methods of the present invention, it is possible to screen for mutant flies in which the eye color was changed from orange to red, indicating a loss of silencing (See Example 1, FIG. 3B-E). The effectiveness of the genetic screen was validated by finding mutant alleles in the two Dicer genes (See, e.g., Lee, et al. Cell 117, 83-94 (2004); Pham et al., Cell 117, 83-94 (2004)), Ago-2 (See, e.g., Liu et al. Science 305, 1437-41 (2004)), and R2D2 (See, e.g., Liu et al., Science 301, 1921-5 (2003)), all of which are known RNAi factors.

It was contemplated that RNAi inhibitors could be discovered using this strategy. It was reasoned that all organisms might contain factors that normally restrict or limit the potency of RNAi, as different species within the same genus can exhibit radically different RNAi responsiveness and mutant variants of the nematode *C. elegans* display enhanced RNAi responsiveness in neurons and other tissues (See, e.g., Simmer et al., Curr Biol 12, 1317 (2002); Kennedy et al., Nature 427, 645-9 (2004)). Therefore, the systems and methods of the present invention were generated in order to identify such inhibitory genes by finding mutations that enhanced RNAi in *Drosophila*. For example, in some embodiments, these mutant flies have their eye color changed from yellow to white (complete silencing), despite carrying only a single white inverted-repeat transgene. The screen was conducted on three autosomal arms representing 60% of the genome. Enhancer mutations were isolated that displayed white eyes (See Examples 1-2, and FIG. 3C). Once the mutant stocks were established, they were retested for their ability to enhance the phenotype induced by RNAi against a totally different gene called Csk. If mutants also enhanced the Csk (RNAi) phenotype, it indicated that the mutants are general enhancers of RNAi and do not affect unrelated phenomena such as white hairpin RNA transcription or pigment metabolism. In some embodiments, these mutants are examined further. For example, complementation analysis can be performed to classify mutations as allelic.

Thus, the present invention provides systems and methods for identifying regulators of RNAi (e.g., inhibitors of RNAi). In some embodiments, an F1 genetic mosaic screen is used to identify RNAi regulators (e.g., See Example 1). The present invention is not limited to the F1 genetic mosaic screen of Example 1. Those skilled in the art will readily appreciate that various modifications and variations of the described F1 genetic mosaic screen system, and methods of using the same, may be used without departing from the scope and spirit of the invention. The present invention has identified multiple regulators of RNAi (e.g., activators and inhibitors) using the above described systems and methods.

For example, in some embodiments, the present invention provides HPS4 and similar agents as a regulator (e.g., inhibitor) of RNAi (See, e.g., Example 2). In some embodiments, the present invention provides HPS1 and similar agents as a regulator (e.g., inhibitor) of RNAi (See, e.g., Examples 2 and 4). In some embodiments, the present invention provides CG6969 and similar agents as a regulator (e.g., inhibitor) of RNAi (See, e.g., Example 9). In some embodiments, the present invention provides compositions and methods for enhancing (e.g., augmenting and/or increasing the efficacy) of RNAi. For example, in some embodiments, the present invention provides a method of enhancing RNAi (e.g., augmenting and/or enhancing gene silencing) comprising altering (e.g., inhibiting or suppressing) the expression and/or activity of an RNAi regulator (e.g., HPS4 and/or HPS1 and/or CG6969). Although an understanding of the mechanism is not necessary to practice the present invention and the present invention is not limited to any particular mechanism of action, in some preferred embodiments, altering (e.g., inhibiting) the expression and/or activity of HPS1 and/or HPS4 and/or CG6969 increases the rate of holo-RISC complex activity, thereby enhancing RNAi. The present invention is not limited to any particular method or composition for altering (e.g., inhibiting) the expression and/or activity of HPS1, HPS4, CG6969 or other RNAi regulator identified by the methods provided herein. Indeed, a variety of methods are contemplated to be useful for altering (e.g., inhibiting) the expression and/or activity of RNAi regulators including, but not limited to, antibodies, small molecules, siRNA and/or miRNA (e.g., specific for HPS1 and/or HPS4 and/or CG6969), and methods of using the same (e.g., antibody or small molecule based inhibition of HPS1 and/or HPS4 activity or RNAi).

The ability to inhibit gene function by RNAi using siRNAs and/or miRNAs synthesized in host cells and/or administered to cells is contemplated to have broad application. For example, in some embodiments, this approach facilitates studies of gene function in transfectable cell lines. In other embodiments, this approach is adaptable to situations for which delivery of in vitro synthesized siRNAs by transfection may not be practical, such as primary cell cultures, studies in intact animals, and gene therapy (ex vivo and in vivo).

Previous results with siRNA suggest that intracellular expression of siRNA against a wide variety of targets will be effective at reducing or eliminating expression of the RNAi regulator targets (e.g., HPS1, HPS4, or other RNAi regulator identified using the systems and methods disclosed herein). In some embodiments of the present invention, an expression cassette is used in combination with different recombinant DNA vectors to target different cell populations. It is contemplated that either one or more than one expression cassettes are inserted in a vector (the cassettes are relatively small); the siRNA encoded by the expression cassette is directed either to the same target (different stretches of RNA on the same target RNA) or to entirely different targets (e.g., multiple RNAi regulators). It is further contemplated that this method of expressing siRNAs from various expression gene cassettes is useful in both experimental and therapeutic applications. Experimental applications include the use of the compositions and methods of the present invention to the field of reverse genetic analysis of genes found in the human genome sequence. Therapeutic applications include the use of the compositions and methods of the present invention in any setting in which gene silencing is contemplated to be useful by those of skill in the art (e.g., including, but not limited to, as antiviral agents, antibacterial agents, or as means to silence undesirable genes such as oncogenes).

Inhibition of RNAi Regulator Expression and/or Activity for Altering (e.g., Enhancing) RNAi Experiments conducted using systems and methods of the present invention identified several RNAi regulators (e.g., HPS1, HPS4 and CG6969). Thus, in preferred embodiments, the present invention provides a method of enhancing RNAi comprising altering (e.g., enhancing or inhibiting) RNAi regulator expression and/or activity. In other preferred embodiments, the present invention provides a method of enhancing RNAi in a cell (e.g., enhancing the silencing (e.g., suppressing the expression) of a target gene (e.g., a non-RNAi regulator gene)) comprising providing an inhibitor of RNAi regulator (e.g., HPS1 and/or HPS4 and/or CG6969) expression and/or activity under conditions such that RNAi in the cell is enhanced (e.g., the inhibition of expression of the target gene is enhanced). Thus, in some preferred embodiments, the present invention provides inhibitors (e.g., siRNAs, antibodies, small molecules, and the like) for use as adjuvants in altering (e.g., boosting or enhancing) RNAi performance within a cell. In still other preferred embodiments, the present invention provides a method of treating a subject receiving an RNA based treatment (e.g., RNAi of a target gene (e.g., comprising administration of a miRNA to the subject (e.g., for the treatment of cancer or hypercholesterolemia))) comprising providing to the subject an inhibitor of an RNAi regulator (e.g., HPS1 and/or HPS4 and/or CG6969) under conditions such that the RNA based treatment (e.g., miRNA) is enhanced (e.g., in some embodiments, target gene expression (e.g., a non-RNAi regulator gene (e.g., an oncogene or aberrantly expressed gene)) is silenced or repressed to a greater extent than in the absence of the RNAi regulator inhibitor). In some embodiments, the target gene is silenced (e.g., gene expression is inhibited) greater than 90%. In some embodiments, the target gene is silenced greater than 95%. In some embodiments, the target gene is silenced greater than 98%. In some embodiments, the target gene is silenced greater than 99%. In some embodiments, silencing is increased 5%, 10%, 100%, 300% or more in the presence of an RNAi regulator inhibitor compared to the expression in its absence.

In preferred embodiments, the present invention provides a method of enhancing RNAi in a cell comprising altering RNAi regulator expression and/or activity in the cell. In some embodiments, altering RNAi regulator expression and/or activity comprises reducing RNAi regulator expression and/or activity. In some embodiments, altering RNAi regulator expression and/or activity comprises providing to the cell a composition comprising an RNAi regulator inhibitor. The present invention is not limited by the type of RNAi regulator inhibitor used to inhibit RNAi regulator activity and/or expression for enhancing RNAi in a cell. Indeed, any compound, pharmaceutical, small molecule or agent (e.g., siRNA) that can alter RNAi regulator expression and/or activity is contemplated to be useful in the methods of the present invention. Examples of inhibitors of RNAi regulator expression and/or activity that find use in enhancing RNAi in cells (e.g, for delivering to and/or providing—e.g., expressing within cells) include, but are not limited to, dominant-negative RNAi regulator or derivative thereof, antisense nucleic acids (including, but not limited to, siRNAs described herein, ribozymes and triple-helix-forming oligonucleotides), anti-RNAi regulator antibodies (e.g., antibodies described herein, as well as intracellular single chain Fv antibodies, See, e.g., Chen, Mol. Med. Today 3:160-167, 1997; Spitz et al., Anti-cancer Res. 16:3415-3422, 1996; Indolfi et al., Nat. Med. 2:634-635, 1996; Kijima et al., Pharmacol. Ther. 68:247-267, 1995, each of which is herein incorporated by reference), small molecule inhibitors (See, e.g., Nature Cell Biology 7, 493-500, 2005, herein incorporated by reference), and RNAi regulator inhibitors identified by the methods of U.S. Pat. No. 6,348,311, and U.S. Pat. App. Nos. 20030157577, 20040014701, 20040002492, 20050054657, and 20050148020, each of which is incorporated herein by reference in its entirety.

In some embodiments, altering RNAi regulator expression and/or activity comprises providing to a cell RNAi regulator specific siRNAs. In some embodiments, the siRNAs reduce expression of one or more RNAi regulators (e.g., HPS1 and/or HPS4 and/or CG6969). In some embodiments, altering RNAi regulator expression and/or activity comprises providing to the cell an antibody specific for a RNAi regulator. In some embodiments, the antibody reduces activity of a RNAi regulator in the cell. In some embodiments, altering RNAi regulator expression and/or activity in the cell sensitizes the cell to therapeutic treatment. In some embodiments, sensitizing the cell to therapeutic treatment permits the cell to undergo treatment-induced cell death. In some embodiments, altering RNAi regulator expression and/or activity works in concert with another treatment (e.g., siRNA and/or miRNA) thereby providing beneficial treatment to a subject.

In some embodiments, the present invention also provides a method of treating a subject with symptoms of a disease (e.g., symptoms associated with cancer, or symptoms associated with any disease caused in part by aberrant gene expression) comprising providing a composition comprising an inhibitor of a RNAi regulator; and administering the composition to the subject under conditions such that the symptoms are reduced (e.g., in combination with a therapeutic RNA molecule).

In some embodiments, the present invention also provides a method of treating a subject with aberrant gene expression (e.g., overexpression of a cancer gene (e.g., an oncogene (e.g., including, but not limited to, abl, Bcl-2, Bcl-x1, erb, brca1, brca2, fms, gsp, hst, jun, myc, neu, raf, ras, ret, src, and trk))) comprising providing a composition comprising an inhibitor of a RNAi regulator; and administering the composition to the subject under conditions such that the RNAi regulator expression and/or activity is altered. In preferred embodiments, the composition comprising an inhibitor of a RNAi regulator is co-administered with one or more inhibitors (e.g., siRNAs and/or miRNAs) that target (e.g., for repression of gene expression) a gene that is aberrantly expressed In some embodiments, the present invention provides methods and compositions suitable for therapy (e.g., drug, prodrug, pharmaceutical, or gene therapy) to alter RNAi regulator gene expression, production, or function (e.g., to inhibit RNAi regulator expression and/or activity). In some embodiments, even the smallest amount of regulation (e.g., inhibition of RNAi regulator expression and/or activity) finds use in enhancing an RNAi therapy (e.g., a siRNA and/or miRNA therapy).

In some embodiments, the present invention provides compositions comprising expression cassettes comprising a nucleic acid encoding an inhibitor of a RNAi regulator (e.g., siRNAs, peptides and the like), and vectors comprising such expression cassettes. The methods described below are generally applicable across many species. Any of the vectors and delivery methods disclosed herein can be used for modulation of RNAi regulator activity (e.g., in a therapeutic setting). As disclosed herein, the therapeutic methods of the invention are optimally achieved by targeting the therapy to the affected cells. Means for targeting delivery of various treatments, such as radiation or chemotherapy, are described below. However, in another embodiment, a RNAi regulator inhibitor can be targeted to cells (e.g., using vectors described herein in combination with well-known targeting techniques, for expression of RNAi regulator modulators).

Furthermore, any of the therapies described herein can be tested and developed in animal models. Thus, the therapeutic aspects of the invention also provide assays for RNAi regulator function.

In some embodiments, viral vectors are used to introduce RNAi regulator inhibitors (e.g., siRNAs, proteins or fragments thereof, etc,) to cells. The present invention further provides a method for altering responsiveness of a cell to treatment (e.g., a cancer cell) comprising altering the levels of a RNAi regulator in the cell (e.g., through inhibiting RNAi regulator expression using RNAi). The art knows well multiple methods of altering the level of expression of a gene or protein in a cell (e.g., ectopic or heterologous expression of a gene). The following are provided as exemplary methods of introducing RNAi regulator inhibitors, and the invention is not limited to any particular method.

RNA Based Inhibitors of RNAi Regulators

In some embodiments, the present invention relates to compositions comprising siRNA. For example, the present invention provides siRNA comprising nucleotide sequence that is complementary to a RNAi regulator (e.g., HPS1 and/or HPS4 and/or CG6969 or other RNAi regulator identified by the systems and methods of the present invention, See, e.g., Example 5), recombinant nucleic acid comprising a vector and nucleic acid sequence for expressing RNAi regulator siRNA, pharmaceutical compositions comprising RNAi regulator siRNA, kits comprising such compositions, and methods of using the same in research and/or therapeutic applications.

The present invention discloses siRNA, wherein the siRNA comprises a sense RNA strand and an antisense RNA strand, wherein the sense and the antisense RNA strands form an RNA duplex (e.g., dsRNA), and wherein the duplex comprises a complementary nucleotide sequence that is complementary to at least a part of RNAi regulator mRNA sequence or equivalent sequences, and wherein the complementary nucleotide sequence is less than 25 nucleotides in length, as well as compositions and methods for inhibiting the expression of a RNAi regulator in a cell using the dsRNA. The present invention also discloses compositions and methods for modifying levels of RNAi regulator (e.g., in order to enhance RNAi within a cell). siRNA/dsRNA and/or miRNA of the present invention directs the sequence-specific degradation of RNAi regulator mRNA through RNA interference (RNAi).

In some embodiments, compositions of the present invention comprise dsRNA that hybridizes to RNAi regulator mRNA. For example, in some embodiments, the dsRNA of the invention comprises an RNA strand comprising a complementary nucleotide sequence having a region which is less than 25 nucleotides in length and is complementary to at least a portion of RNAi regulator RNA transcripts. The use of these dsRNAs enables the targeted degradation of RNAi regulator mRNA. Very low dosages of these dsRNA can specifically and efficiently mediate RNAi, resulting in significant inhibition of expression of RNAi regulator (See, e.g., Example 5). The dsRNA of the present invention not only reduce the level of RNAi regulator, they also enhance RNAi inhibition of expression of a target gene (e.g., an aberrantly expressed gene or other gene within a cell (See, e.g., Examples 3-4). Thus, the present invention encompasses these dsRNAs and compositions comprising dsRNA and their use for specifically silencing a RNAi regulator. Moreover, the dsRNAs of the invention have no apparent effect on neighboring normal cells. Thus, the methods and compositions of the present invention comprising these dsRNAs are useful for treating cellular proliferative and/or differentiation disorders, such as cancer.

The following detailed description discloses how to make and use the siRNA/dsRNA/miRNA of the present invention and compositions containing dsRNA to inhibit the expression of RNAi regulator. In some embodiments, The pharmaceutical compositions of the present invention comprise a dsRNA having an RNA strand comprising a complementary nucleotide sequence that is less than 25 nucleotides in length and is complementary to at least a portion of a RNAi regulator RNA transcript of RNAi regulator, together with a pharmaceutically acceptable carrier. The pharmaceutical composition may comprise a combination of dsRNAs having regions complementary to a plurality of sites within a RNAi regulator. The compositions of the present invention can be used in combination with other known therapeutic agents (e.g., siRNA and/or chemotherapeutic agents).

Accordingly, certain aspects of the present invention relate to pharmaceutical compositions comprising the dsRNA of the present invention, or vectors containing the same, together with a pharmaceutically acceptable carrier, methods of using the compositions to inhibit expression of a RNAi regulator, and methods of using the pharmaceutical compositions to treat diseases caused by expression (e.g., aberrant expression) of a target gene.

A. Pharmaceutical Compositions Comprising dsRNA

1. Double-Stranded Ribonucleic Acid (dsRNA)

In one embodiment, the invention relates to a RNA duplex/double-stranded ribonucleic acid (dsRNA) having a nucleotide sequence which is substantially identical to at least a portion of a RNAi regulator. The dsRNA comprises two RNA strands that are sufficiently complementary to hybridize to form the duplex structure. One strand of the dsRNA comprises the nucleotide sequence that is substantially identical to a portion of the target gene (the "sense" strand), and the other strand (the "complementary" or "antisense" strand) comprises a complementary nucleotide sequence that is complementary to an RNA transcript of the target gene. The complementary region is between 19 and 24, preferably between 21 and 23, and most preferably 22 nucleotides in length. The dsRNA is less than 30 nucleotides, preferably less than 25 nucleotides, and most preferably between 21 and 24 nucleotides in length. The dsRNA can be synthesized by standard methods known in the art, e.g., by use of an automated DNA synthesizer, such as are commercially available from Biosearch, Applied Biosystems, Inc, etc.

In one embodiment, at least one end of the dsRNA has a single-stranded nucleotide overhang of 1 to 7, preferably 1 or 2 nucleotides. dsRNAs having at least one nucleotide overhang have unexpectedly superior inhibitory properties than their blunt-ended counterparts. dsRNA having only one overhang has proven particularly stable and effective in vivo, as well as in a variety of cells, cell culture mediums, blood, and serum. Preferably, the single-stranded overhang is located at the 3'-terminal end of the complementary (antisense) RNA strand or, alternatively, at the 3'-terminal end of the second (sense) strand. The dsRNA may also have a blunt end, preferably located at the 5'-end of the complementary (antisense) strand. Such dsRNAs have improved stability and inhibitory activity, thus allowing administration at low dosages, e.g., less than 5 mg/kg body weight of the recipient per day. Preferably, the complementary strand of the dsRNA has a nucleotide overhang at the 3'-end, and the 5'-end is blunt. In another embodiment, one or more of the nucleotides in the overhang is replaced with a nucleoside thiophosphate.

In yet another embodiment, the dsRNA is chemically modified for improved stability, e.g., enhanced resistance to degradation and/or strand dissociation. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. In one embodiment, the linker is a hexa-ethylene glycol linker. In this case, the dsRNAs are produced by solid phase synthesis and the hexa-ethylene glycol linker is incorporated according to standard methods (See, e.g., Williams, D. J., and K. B. Hall, Biochem. (1996) 35:14665-14670). In a preferred embodiment, the 5'-end of the complementary (antisense) RNA strand and the 3'-end of the second (sense) RNA strand are chemically linked via a hexa-ethylene glycol linker. In yet another preferred embodiment, the dsRNA is linked via a single stranded nucleic acid forming a loop or hairpin structure.

In one embodiment, the invention relates to a pharmaceutical composition comprising a dsRNA, as described in the preceding section, and a pharmaceutically acceptable carrier, as described below. The pharmaceutical composition comprising the dsRNA is useful for treating a disease or disorder associated with the expression of a target gene (e.g., aberrant expression of an oncogene).

In another embodiment, the invention relates to a pharmaceutical composition comprising at least two dsRNAs, designed to target different regions of a RNAi regulator, and a pharmaceutically acceptable carrier. A composition comprising a plurality of dsRNA that target multiple regions of a RNAi regulator may provide improved efficiency of treatment as compared to compositions comprising only a single dsRNA. In addition, a composition may be generated that includes a dsRNA specific for a RNAi regulator as well as a dsRNA specific for a target gene(s) (e.g., an oncogene). The multiple dsRNAs may be combined in the same pharmaceutical composition, or formulated separately. If formulated individually, the compositions containing the separate dsRNAs may comprise the same or different carriers, and may be administered using the same or different routes of administration. Moreover, the pharmaceutical compositions comprising the individual dsRNAs may be administered substantially simultaneously, sequentially, or at preset intervals throughout the day or treatment period. The present invention contemplates use of RNAi regulator specific dsRNAs of the present invention in combinatorial use with dsRNA for any gene or combination of genes.

2. Recombinant Nucleic Acids Comprising a Vector and Nucleic Acid Sequence for Expressing dsRNA In some embodiments, the dsRNA of the invention can be obtained using a number of techniques known to those of skill in the art. For example, the dsRNA can be chemically synthesized or recombinantly produced using methods known in the art, such as the *Drosophila* in vitro system described in U.S. published application 2002/0086356 of Tuschl et al., the entire disclosure of which is herein incorporated by reference.

In some embodiments, the dsRNA of the invention are chemically synthesized using appropriately protected ribonucleoside phosphoramidites and a conventional DNA/RNA synthesizer. The dsRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK).

In preferred embodiments, dsRNA is expressed from recombinant circular or linear DNA plasmids using any suitable promoter. Suitable promoters for expressing dsRNA of the invention from a plasmid include, for example, the U6 or H1 RNA pol III promoter sequences and the cytomegalovirus promoter. Selection of other suitable promoters is within the skill in the art (e.g., use of regulatable or tissue-specific promoters). The recombinant plasmids of the invention can also comprise inducible or regulatable promoters for expression of the dsRNA in a particular tissue or in a particular intracellular environment.

dsRNA of the invention can be expressed from a recombinant plasmid either as two separate, complementary RNA molecules, or as a single RNA molecule with two complementary regions.

Selection of plasmids suitable for expressing dsRNA of the invention, methods for inserting nucleic acid sequences for expressing the dsRNA into the plasmid, and methods of delivering the recombinant plasmid to the cells of interest are within the skill in the art (See, e.g., Tuschl, T. (2002), Nat. Biotechnol, 20: 446-448; Brummelkamp T R et al. (2002), Science 296: 550-553; Miyagishi M et al. (2002), Nat. Biotechnol. 20: 497-500; Paddison P J et al. (2002), Genes Dev. 16: 948-958; Lee N S et al. (2002), Nat. Biotechnol. 20: 500-505; and Paul C P et al. (2002), Nat. Biotechnol. 20: 505-508, the entire disclosures of which are herein incorporated by reference).

In one embodiment, a plasmid expressing a dsRNA of the invention comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. Such a plasmid can be used in producing a recombinant adeno-associated viral vector for expressing a dsRNA of the invention.

The dsRNA expressed from recombinant plasmids can either be isolated from cultured cell expression systems by standard techniques, or can be expressed intracellularly. Any viral vector capable of accepting the coding sequences for the dsRNA molecule(s) to be expressed can be used, for example vectors derived from adenovirus (AV); adeno-associated virus (AAV); retroviruses (e.g, lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors which express different capsid protein serotypes are within the skill in the art (See, e.g., Rabinowitz J E et al. (2002), J Virol 76:791-801, the entire disclosure of which is herein incorporated by reference).

Selection of recombinant viral vectors suitable for use in the invention, methods for inserting nucleic acid sequences for expressing the dsRNA into the vector, and methods of delivering the viral vector to the cells of interest are within the skill in the art. (See, e.g., Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and GenScript siRNA Construct Builder, www.GenScript.com) the entire disclosures of which are herein incorporated by reference.

Preferred viral vectors are those derived from lentivirus, AV or AAV. In a particularly preferred embodiment, the siRNA of the invention is expressed from a single sequence inserted into a plasmid (e.g., pRNAT-U6.1/Hygro from GenScript).

Suitable AV vectors for expressing the dsRNA of the invention, a method for constructing the recombinant AV vector, and a method for delivering the vector into target cells, are described in Xia H et al. (2002), Nat. Biotech. 20: 1006-1010. Suitable AAV vectors for expressing the siRNA of the invention, methods for constructing the recombinant AAV vector, and methods for delivering the vectors into target cells are described in Samulski R et al. (1987), J. Virol. 61: 3096-3101; Fisher K J et al. (1996), J. Virol., 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

In some embodiments, the present invention employs compositions comprising oligomeric antisense compounds, particularly oligonucleotides (e.g., those identified in the drug screening methods described herein), for use in modulating the function of nucleic acid molecules encoding a RNAi regulator, ultimately modulating the amount of a RNAi regulator expressed. This is accomplished by providing antisense compounds that specifically hybridize with one or more nucleic acids encoding a RNAi regulator (e.g., HPS1 or HPS4). The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of a RNAi regulator. In the context of the present invention, "modulation" means either an increase (stimulation) or a decrease (inhibition) in the expression of a gene. For example, in preferred embodiments, expression is inhibited to enhance the RNAi based gene silencing in a cell.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a RNAi regulator (e.g., HPS1 and/or HPS4 and/or CG6969 or other RNAi regulator identified by the systems and methods disclosed herein). The targeting process also includes determination of a site or sites within this gene for the antisense interaction to occur such that the desired effect (e.g., detection or modulation of expression of the protein) will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG that have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (e.g., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (e.g., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (e.g., from about 8 to about 30 linked bases), although both longer and shorter sequences may find use with the present invention. Particularly preferred antisense compounds are antisense oligonucleotides, even more preferably those comprising from about 12 to about 25 nucleobases, or even more preferably, about 22 nucleobases (e.g., 21-24 nucleobases).

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (e.g., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference in its entirety. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O(($CH_2$)$_n$O)$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON(($CH_2$)$_n$$CH_3$))$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2$$CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2$$CH_2$O$CH_3$, also known as 2'-O-(2-methoxyethyl) or 2'-MOE) (Martin et al., Helv. Chim. Acta 78:486 (1995)) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit (e.g., a nucleotide in the case of an oligonucleotide compound). These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

In some embodiments, the present invention provides a method of treating cells comprising altering responsiveness of the cells to treatment comprising making the cells either more or less responsive (e.g., sensitive) to the treatment. In some embodiments, making the cells more or less responsive (e.g., sensitive) to treatment comprises altering the level of RNAi regulator expression and/or activity in the target cell. The present invention further provides a method of customizing cells for treatment by altering RNAi regulator expression and/or activity in the cells. In some embodiments, altering the level of RNAi regulator in the target cell comprises introducing siRNA and/or miRNA to the target cell (e.g., that inhibit RNAi regulator expression)

While it is conceivable that an RNAi regulator inhibitor (e.g., siRNA, miRNA or peptide) may be delivered directly to a HCMV infected cell, some embodiments involve providing a nucleic acid encoding an RNAi regulator inhibitor to a cell. Following this provision, RNAi regulator inhibitors are synthesized by the transcriptional and translational machinery of the cell. In some embodiments, additional components useful for transcription or translation may be provided by the expression construct comprising RNAi regulator inhibitor sequence.

In some embodiments, the present invention provides methods for in vitro synthesis of RNAi regulator inhibitors (e.g., siRNA, proteins or portions thereof) by in vitro transcription; such methods provide efficient and economical alternatives to chemical synthesis, and the RNAi regulator inhibiors so synthesized can be used to transfect cells. In some embodiments, a siRNA construct (e.g., ds siRNA) can be designed to silence a RNAi regulator, inserted into at least one expression cassette, and transfected into the cell in which the target gene (e.g., RNAi regulator) is expressed. In some embodiments, the present invention provides a method of enhancing RNAi comprising inhibiting a RNAi regulator (e.g, using RNAi). Furthermore, the present invention provides research applications wherein the effect of the lack of or disappearance of the RNAi regulator in the transfected cell is assessed; such results leading to elucidation of the function of the gene.

In some embodiments, research applications are in vivo in cells or tissues (e.g., as when cultured cells or tissues are transfected with either synthetic siRNA or siRNA expression constructs, as described above). In other embodiments, research applications are in vivo (e.g., as when organisms such as mammals are transfected with siRNA expression constructs, as described in further detail below).

In some embodiments, the nucleic acid encoding RNAi regulator inhibitors (e.g., protein or siRNA) may be stably integrated into the genome of the cell. In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on, among other things, the type of expression construct employed.

The ability of certain viruses to infect cells or enter cells via receptor-mediated endocytosis, and to integrate into host cell genome and express viral genes stably and efficiently have made them attractive candidates for the transfer of foreign genes into mammalian cells. In some embodiments, vectors of the present invention are viral vectors (e.g., phage or adenovirus vectors).

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein.

The expression vector may comprise a genetically engineered form of adenovirus. Knowledge of the genetic organization or adenovirus, a 36 kb, linear, double-stranded DNA virus, allows substitution of large pieces of adenoviral DNA with foreign sequences up to 7 kb (See Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 map units (m.u.)) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (E1A and E1B; Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical adenovirus vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus growth and manipulation is known to those of skill in the art, and exhibits broad host range in vitro and in vivo. This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recombinant adenovirus and adeno-associated virus (see below) can both infect and transduce non-dividing human primary cells.

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference in their entireties.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994).

AAV is a dependent parvovirus in that it requires coinfection with another virus (either adenovirus or a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome or from a recombinant plasmid, and a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and an expression plasmid containing the wild type AAV coding sequences without the terminal repeats, for example pIM45 (McCarty et al., 1991; incorporated herein by reference). The cells are also infected or transfected with adenovirus or plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions or cell lines containing the AAV coding regions and some or all of the adenovirus helper genes could be used (Yang et al., 1994; Clark et al., 1995). Cell lines carrying the rAAV DNA as an integrated provirus can also be used (Flotte et al., 1995).

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These 4contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and pre-surface coding sequences.

In certain further embodiments, the vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

In still further embodiments of the present invention, the nucleic acids to be delivered (e.g., nucleic acids encoding RNAi regulator inhibitors) are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

In various embodiments of the invention, nucleic acid sequence encoding RNAi regulator inhibitors is delivered to a cell as an expression construct. In order to effect expression of a gene construct, the expression construct is delivered into a cell. As described herein, one mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA or plasmids (e.g., vectors comprising nucleic acid sequences of the present invention). Transfer of the construct may be performed by any of the methods mentioned which physically or chemically permeabilize the cell membrane. Some of these techniques may be successfully adapted for in vivo or ex vivo use, as discussed below.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

In certain embodiments of the present invention, the expression construct is introduced into the cell via electroporation. Electroporation involves the exposure of a suspension of cells (e.g., bacterial cells such as E. coli) and DNA to a high-voltage electric discharge.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

In other embodiments of the present invention, the expression construct is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells have been transfected with a neomycin marker gene (Chen and Okayama, 1987), and rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and erythroleukemia cells (Gopal, 1985).

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Further embodiments of the present invention include the introduction of the expression construct by direct microinjection or sonication loading. Direct microinjection has been used to introduce nucleic acid constructs into *Xenopus* oocytes (Harland and Weintraub, 1985), and LTK⁻ fibroblasts have been transfected with the thymidine kinase gene by sonication loading (Fechheimer et al., 1987).

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

Still further expression constructs that may be employed to deliver nucleic acid construct to target cells are receptor-mediated delivery vehicles. These take advantage of the selective uptake of macromolecules by receptor-mediated endocytosis that will be occurring in the target cells. In view of the cell type-specific distribution of various receptors, this delivery method adds another degree of specificity to the present invention.

Certain receptor-mediated gene targeting vehicles comprise a cell receptor-specific ligand and a DNA-binding agent. Others comprise a cell receptor-specific ligand to which the DNA construct to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique.

In other embodiments, the DNA delivery vehicle component of a cell-specific gene targeting vehicle may comprise a specific binding ligand in combination with a liposome. The nucleic acids to be delivered are housed within the liposome and the specific binding ligand is functionally incorporated into the liposome membrane. The liposome will thus specifically bind to the receptors of the target cell and deliver the contents to the cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the DNA delivery vehicle component of the targeted delivery vehicles may be a liposome itself, which will preferably comprise one or more lipids or glycoproteins that direct cell-specific binding. For example, Nicolau et al. (1987) employed lactosyl-ceramide, a galactose-terminal asialganglioside, incorporated into liposomes and observed an increase in the uptake of the insulin gene by hepatocytes. It is contemplated that the tissue-specific transforming constructs of the present invention can be specifically delivered into the target cells in a similar manner.

Genetic Therapies

The present invention contemplates the use of any genetic manipulation for use in modulating the expression of RNAi regulator. Examples of genetic manipulation include, but are not limited to, gene knockout (e.g., removing the RNAi regulator from the chromosome using, for example, recombination), expression of antisense constructs with or without inducible promoters, and the like. Delivery of nucleic acid construct to cells in vitro or in vivo or ex vivo may be conducted using any suitable method (e.g., using the methods described herein). A suitable method is one that introduces the nucleic acid construct into the cell such that the desired event occurs (e.g., expression of an antisense construct).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into cells or tissue using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

Pharmaceutical Compositions

The present invention further provides pharmaceutical compositions (e.g., comprising RNAi regulator inhibitors described herein). The pharmaceutical compositions of the present invention may be administered in a number of ways depending upon whether local or systemic treatment is desired and upon the area to be treated. For example, administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral, anal, or parenteral, although the present invention is not limited to these routes of administration. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

In some embodiments, the invention provide pharmaceutical compositions containing (a) one or more RNAi regulator inhibitors (e.g., antisense compounds) and (b) one or more other therapeutic agent (e.g. siRNA targeting a non-RNAi regulator gene). The two or more combined agents (e.g., a siRNA targeting a non-RNAi regulator gene and an RNAi regulator inhibitor (e.g., siRNA, peptide, small molecule, antibody, or the like) may be used together or sequentially.

Dosing is dependent on severity and responsiveness of the disease state (e.g., severity of symptoms caused by aberrant expression of a gene (e.g., an oncogene)) to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the a drug in bodily fluids or tissues. Following successful treatment, it may be desirable to have the subject undergo maintenance therapy to prevent the recurrence of the disease state, wherein, for example, a pharmaceutical or drug comprising a RNAi regulator inhibitor (e.g., siRNA) and one or more other agents (e.g., a siRNA specific for a non-RNAi regulator gene) is administered in maintenance doses, ranging from 0.01 µg to 100 g per kg of body weight, once or more daily, to once every 20 years.

Antibodies

The present invention further provides methods of generating antibodies for detecting and/or inhibiting a RNAi regulators (e.g. HPS1, HPS4, CG6969, or other RNAi regulator identified by the systems and methods of the present invention). For example, in some embodiments, the present invention provides monoclonal or polyclonal antibodies that specifically bind to an isolated polypeptide comprised of at least five amino acid residues of HPS1 or HPS4. These antibodies find use in the therapeutic methods described herein.

An antibody against a RNAi regulator of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a RNAi regulator of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a RNAi regulator of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, HPS1 and/or HPS4 and/or CG6969 protein (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

In some embodiments, antibodies (e.g., monoclonal antibodies) are humanized. Such humanized antibodies find particular use in the cancer immunotherapies described below. Humanized antibodies are altered in order to make them less immunogenic to humans, e.g., by constructing chimeric antibodies in which a mouse antigen-binding variable domain is coupled to a human constant domain. Humanized antibodies are typically human antibodies in which some CDR residues and possibly some FR residues are substituted by residues from analogous sites in rodent antibodies. Methods for humanizing antibodies are well known in the art and include but are not limited to, those disclosed in U.S. Pat. Nos. 6,054,297, 4,816,567, 6,180,377, 5,871,907, 5,585,089, and 6,180,370, each of which is herein incorporated by reference in its entirety.

Drug Screening

In some embodiments, the present invention provides drug screening assays (e.g., to screen for agents (e.g., small molecules, proteins, etc.) that can inhibit a RNAi regulator's function. The screening methods of the present invention utilize a RNAi regulator of the present invention. For example, in some embodiments, the present invention provides methods of screening for compounds that alter (e.g., increase or decrease) the expression of a RNAi regulator. In some embodiments, candidate compounds are antisense agents (e.g., oligonucleotides) directed against a RNAi regulator (See, e.g., Example 5). In other embodiments, candidate compounds are antibodies. In some embodiments, the candidate compound is a small molecule.

In one screening method, candidate compounds are evaluated for their ability to alter RNAi regulator presence, activity or expression by contacting a compound with a cell (e.g., an cell expressing a RNAi regulator or capable of generating a RNAi regulator) and then assaying for the effect of the candidate compounds on the presence or expression of a RNAi regulator. In some embodiments, the effect of candidate compounds on expression or presence of a RNAi regulator (e.g., HPS1 and/or HPS4 and/or CG6969) is assayed for by detecting the level of RNAi regulator present within the cell.

In other embodiments, the effect of candidate compounds on expression or presence of a RNAi regulator is assayed by measuring the level of polypeptide encoded by the RNAi regulator. The level of polypeptide expressed can be measured using any suitable method, including but not limited to, those disclosed herein.

Specifically, the present invention provides screening methods for identifying modulators, (e.g., candidate or test compounds or agents (e.g., proteins, peptides, peptidomimetics, peptoids, small molecules or other drugs)) that bind to proteins that generated RNAi regulators of the present invention, have an inhibitory (or stimulatory) effect on, for example, RNAi regulator expression, RNAi regulator activity or RNAi regulator presence, or have a stimulatory or inhibitory effect on, for example, the expression or activity of a RNAi regulator substrate. Compounds thus identified can be used to modulate the activity of target gene products either directly or indirectly in a therapeutic protocol, to elaborate the biological function of the target gene product, or to identify compounds that disrupt normal target gene interactions. Compounds that inhibit or enhance the activity, expression or presence of RNAi regulators find use in the treatment of cancer or other diseases that are characterized by aberrant gene expression (e.g., other proliferative disorders).

In one embodiment, the invention provides assays for screening candidate or test compounds that are substrates of a RNAi regulator. In another embodiment, the invention provides assays for screening candidate or test compounds that bind to or modulate the activity of a RNAi regulator.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364: 555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that contains or is capable of generating a RNAi regulator (e.g., HPS1 and/or HPS4) is contacted with a test compound, and the ability of the test compound to modulate the RNAi regulator's presence, expression or activity is determined. Determining the ability of the test compound to modulate RNAi regulator presence, expression or activity can be accomplished by monitoring, for example, changes in enzymatic activity or downstream products (e.g., rate or amount of holo-RISC assembly formation).

The ability of the test compound to modulate RNAi regulator binding to a compound (e.g., a RNAi regulator substrate) can also be evaluated. This can be accomplished, for example, by coupling the compound (e.g., the substrate) with a radioisotope or enzymatic label such that binding of the compound (e.g., the substrate) to a RNAi regulator can be determined by detecting the labeled compound (e.g., substrate) in a complex.

Alternatively, the RNAi regulator can be coupled with a radioisotope or enzymatic label to monitor the ability of a test compound to modulate RNAi regulator binding to a substrate in a complex. For example, compounds (e.g., substrates) can be labeled with $^{125}I$, $^{35}S$, $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a RNAi regulator substrate) to interact with a RNAi regulator with or without the labeling of any of the interactants can be evaluated. For example, a microphysiometer can be used to detect the interaction of a compound with a RNAi regulator without the labeling of either the compound or the RNAi regulator (See, e.g., McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and RNAi regulators.

In yet another embodiment, a cell-free assay is provided in which a RNAi regulator is contacted with a test compound and the ability of the test compound to bind to the RNAi regulator is evaluated.

Cell-free assays involve preparing a reaction mixture of the target gene protein and the test compound under conditions and for a time sufficient to allow the two components to interact and bind, thus forming a complex that can be removed and/or detected.

The interaction between two molecules (e.g., a RNAi regulator and a compound) can also be detected, e.g., using fluorescence energy transfer (FRET) (See, e.g., Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determining the ability of the RNAi regulator to bind to a target molecule can be accomplished using real-time Biomolecular Interaction Analysis (BIA) (See, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize RNAi regulators, an anti-RNAi regulator antibody or its target molecule to facilitate separation of complexed from non-complexed forms of one or both of the molecules, as well as to accommodate automation of the assay. Binding of a test compound to a RNAi regulator or interaction of a RNAi regulator with a target molecule in the presence and absence of a candidate compound, can be accomplished in any vessel suitable for containing the reactants. Examples of such vessels include microtiter plates, test tubes, and micro-centrifuge tubes.

For example, in one embodiment, a fusion protein can be provided which adds a domain that allows one or both of the molecules to be bound to a matrix. For example, a glutathione-S-transferase/target fusion protein can be adsorbed onto glutathione Sepharose beads (Sigma Chemical, St. Louis, Mo.) or glutathione-derivatized microtiter plates, which are then combined with the test compound or the test compound and either the non-adsorbed target protein or RNAi regulator, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of RNAi regulator binding or activity determined using standard techniques. Other techniques for immobilizing either RNAi regulator molecule (e.g., nucleic acid or protein) or a target molecule on matrices include using conjugation of biotin and streptavidin. Biotinylated biomarker or target molecules can be prepared from biotin-NHS(N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with RNAi regulator or target molecules but which do not interfere with binding of the RNAi regulator to its target molecule. Such antibodies can be derivatized to the wells of the plate, and unbound target or RNAi regulator trapped in the wells by antibody conjugation. Methods for detecting such complexes, in addition to those described above for the GST-immobilized complexes, include immunodetection of complexes using antibodies reactive with the biomarker or target molecule, as well as enzyme-linked assays which rely on detecting an enzymatic activity associated with the RNAi regulator or target molecule.

Alternatively, cell free assays can be conducted in a liquid phase. In such an assay, the reaction products are separated from unreacted components, by any of a number of standard techniques, including, but not limited to: differential centrifugation (See, e.g., Rivas and Minton, Trends Biochem Sci 18:284-7 (1993)); chromatography (gel filtration chromatography, ion-exchange chromatography); electrophoresis (See, e.g., Ausubel et al., eds. Current Protocols in Molecular Biology 1999, J. Wiley: New York.); and immunoprecipitation (See, e.g., Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 (1998); Hageand Tweed J. Chromatogr. Biomed. Sci. Appl 699:499-525

(1997)). Further, fluorescence energy transfer may also be conveniently utilized, as described herein, to detect binding without further purification of the complex from solution.

The assay can include contacting the RNAi regulator with a known compound that binds the RNAi regulator to form an assay mixture, contacting the assay mixture with a test compound, and determining the ability of the test compound to interact with a RNAi regulator, wherein determining the ability of the test compound to interact with a RNAi regulator includes determining the ability of the test compound to preferentially bind to RNAi regulator, or to modulate the activity of a target molecule, as compared to the known compound.

To the extent that RNAi regulators can, in vivo, interact with one or more cellular or extracellular macromolecules, such as proteins, inhibitors of such an interaction are useful. A homogeneous assay can be used to identify inhibitors.

For example, a preformed complex of the target gene product and the interactive cellular or extracellular binding partner product is prepared such that either the target gene products or their binding partners are labeled, but the signal generated by the label is quenched due to complex formation (See, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, RNAi regulators can be used as a "bait" in a two-hybrid assay or three-hybrid assay (See, e.g., U.S. Pat. No. 5,283,317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent W0 94/10300; each of which is herein incorporated by reference), to identify proteins that bind to or interact with RNAi regulators ("RNAi regulator-binding proteins" or "RNAi regulator-bp"). Such RNAi regulator-bps can be activators or inhibitors of signals by the RNAi regulators or targets as, for example, downstream elements of a biomarker-mediated signaling pathway (e.g. holo-RISC activity).

Modulators of RNAi regulator presence can also be identified. For example, a cell or cell free mixture can be contacted with a candidate compound and the presence of RNAi regulator evaluated relative to the level of RNAi regulator in the absence of the candidate compound. When presence of RNAi regulator is greater in the presence of the candidate compound than in its absence, the candidate compound is identified as a stimulator of RNAi regulator accumulation. Alternatively, when presence of RNAi regulator is less (i.e., statistically significantly less) in the presence of the candidate compound than in its absence, the candidate compound is identified as an inhibitor of RNAi regulator accumulation. The level of RNAi regulator presence can be determined by methods described herein for detecting RNAi regulator.

A modulating agent can be identified using a cell-based or a cell free assay, and the ability of the agent to modulate the activity of a RNAi regulator can be confirmed in vivo, e.g., in an animal such as an animal model for a disease (e.g., an animal with cancer or cells from a cancer resulting from aberrant gene expression or cells from a cancer cell line).

This invention further pertains to novel agents identified by the above-described screening assays. Accordingly, it is within the scope of this invention to further use an agent identified as described herein (e.g., a RNAi regulator modulating agent, an antisense RNAi regulator nucleic acid molecule, a siRNA molecule, a RNAi regulator specific antibody, or a RNAi regulator-binding substrate) in an appropriate animal model (such as those described herein) to determine the efficacy, toxicity, side effects, or mechanism of action, of treatment with such an agent. Furthermore, novel agents identified by the above-described screening assays can be used (e.g., for treatments as described herein).

Research Applications

The compositions and methods of the present invention are applicable to the field of reverse genetic analysis, by gene silencing. In some embodiments, the present invention provides methods for in vitro synthesis of siRNA (e.g., either ds siRNA or hairpin siRNA, by in vitro transcription). Such methods provide efficient and economical alternatives to chemical synthesis, and the siRNAs so synthesized can be used to transfect cells. In other embodiments, a siRNA construct (e.g., ds siRNA) can be designed to silence a RNAi regulator of the present invention (See, e.g., Examples 2-4), inserted into at least one expression cassette, and transfected into the cell in which the target gene is expressed. The effect of the lack of or disappearance of RNAi regulator in the transfected cell can then be assessed; such results often lead to elucidation of the function of the gene.

In some embodiments, research applications are in vivo in cells or tissues, as when cultured cells or tissues are transfected with either synthetic siRNA or siRNA expression constructs, as described above. In other embodiments, research applications are in vivo, as when organisms such as mammals are transfected with siRNA expression constructs, as described in further detail herein.

EXPERIMENTAL

The following examples are provided in order to demonstrate and further illustrate certain preferred embodiments and aspects of the present invention and are not to be construed as limiting the scope thereof.

Example 1

Systems and Methods to Identify RNAi Regulators (e.g., Inhibitors)

Several observations provided a basis to examine whether organisms might contain factors that normally restrict or limit the potency of RNAi. First, different species within the same genus exhibit radically different RNAi responsiveness. Second, mutant variants of the nematode *C. elegans* display enhanced RNAi responsiveness (See, e.g., Kennedy et al., (2004) Nature 427, 645-649). Thus, an approach was taken to genetically identify inhibitory factors (e.g., RNAi regulators) in a tractable model system, identify homologues of such regulators in other species, and determine whether these factors have a universal function as RNAi regulators (e.g., inhibitors). A further goal was to determine whether blocking (e g inhibiting expression and/or function) of these regulators during and RNAi application would enhance the strength of the RNAi response.

A strategy to discover RNAi regulatory genes was to use saturation mutagenesis and identify recessive mutant variants that exhibit stronger RNAi than normal. It was determined that a genetic screen that saturates the genome with mutations would be the most extensive means to identify the genes of interest. An essential requirement for conducting this type of screen is the ability to induce a uniform and consistent RNAi response in mutagenized animals. Moreover, to allow saturation mutagenesis, thousand of animals needed to be screened, necessitating inducing RNAi on a large scale. Injection, soaking, or bombardment of *Drosophila* was unsatisfactory in both scale and uniformity.

A transgenic approach was more feasible. The underlying assumption of transgenic RNAi is that organisms synthesize dsRNA themselves and induce self-silencing. This requires that the gene encoding a dsRNA trigger is in trans to the target gene. In *Drosophila*, P-element mediated transformation is a simple means to introduce a transgene into the genome. Thus, it has the potential to work in the whole organism and to be stably inherited within a purebred stock. This design was explored by making the transgene as an inverted repeat, thereby producing a hairpin RNA product (See, e.g., Kennerdell and Carthew (2000) Nat Biotechnol 18, 896-898).

A snapback transgene against lacZ was designed. Part of the lacZ coding region was inserted as an inverted repeat into a transformation vector. When this was done, the sapback construct cell-autonomously inhibited expression of a reporter lacZ gene in many tissues at a variety of developmental stages.

Despite its successes, one of the problems with the strategy was that the silencing effect was variable. Affected individuals exhibited a spectrum of RNAi-induced phenotypes. Such non-uniformity meant that any screen would pick out many false-positives and miss many potential mutants. These problems, in part, inspired the generation of the systems and methods of the present invention.

Figure 2:
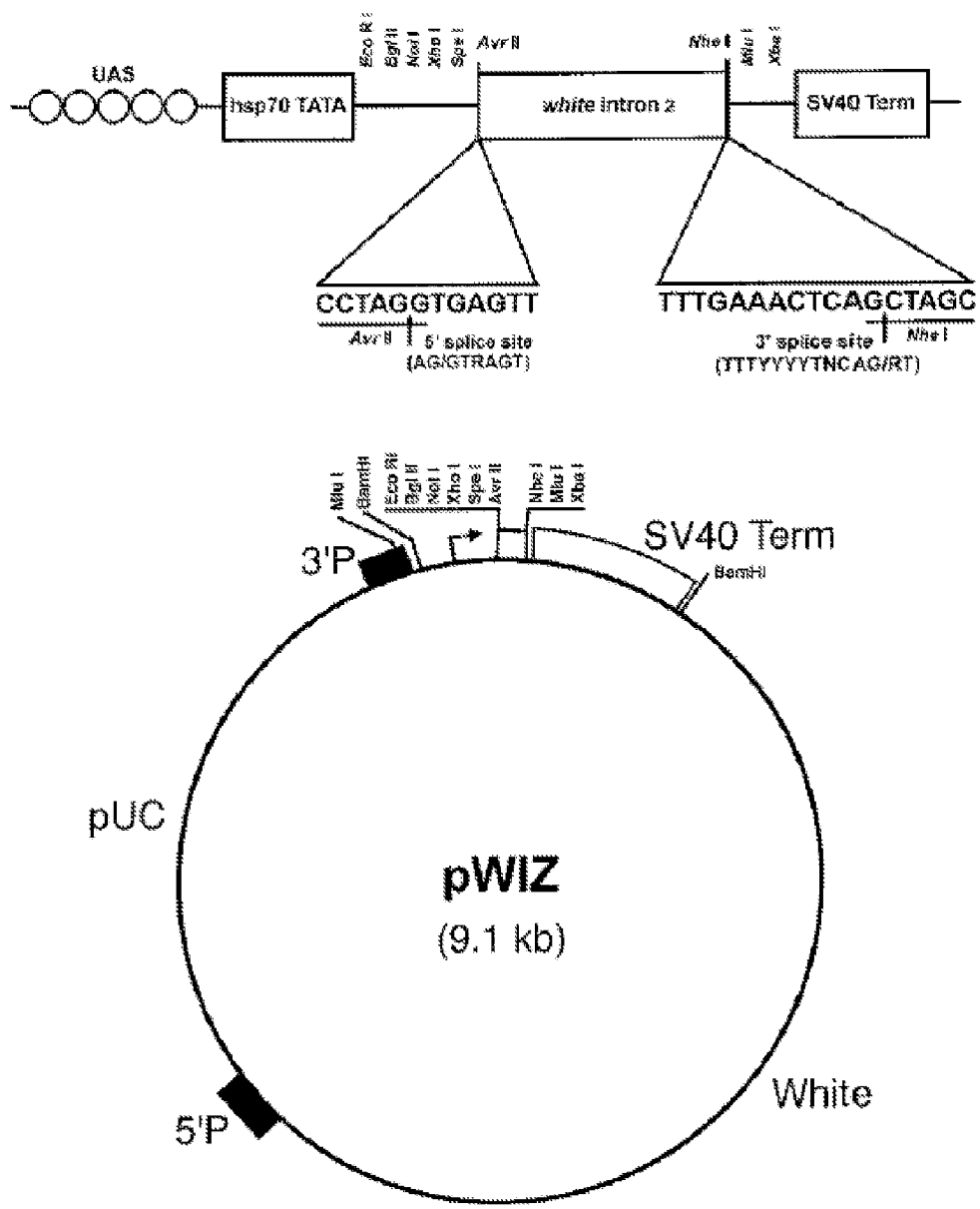
FIG. 2 (SEQ ID NOS: 16-18) depicts the vector pWIZ described in Example 1.

A modular RNAi transgene vector was constructed that expresses spliced hairpin RNA (See, e.g., Lee and Carthew (2003) Methods 30, 322-329). The vector, called pWIZ for White Intron Zipper, is designed so that gene fragments can be subcloned upstream and downstream of a 74-nt intron of the white gene (See FIG. 2). The intron bears all features of a consensus *Drosophila* intron and it can be spliced in heterologous tissues. Insertion of any fragment upstream and downstream of the intron maintains the 5' and 3' splice sites.

The intron-based approach was used to target a reporter gene for screening. The white gene was chosen as an RNAi target. The white gene encodes an ABC transporter required cell-autonomously to pigment the adult compound eye (See, e.g., Mackenzie et al., (2000) Genetica 108, 239-252). A white$^+$ eye is dark red in color while a null white mutant is completely white. This phenotype is easily scored under low magnification with a stereomicroscope, affording easy and rapid phenotype screening. Loss of white has no impact on viability or fertility. Additionally, mutant alleles with reduced activity can be ordered by a phenotypic series: red, brown, orange, yellow, white. A semiquantitative relationship exists between expression level and phenotype such that partially reduced expression results in an intermediate phenotype (See, e.g., Mackenzie et al., (1999) Biochim Viophys Acta 1419, 173-185).

Figure 3:
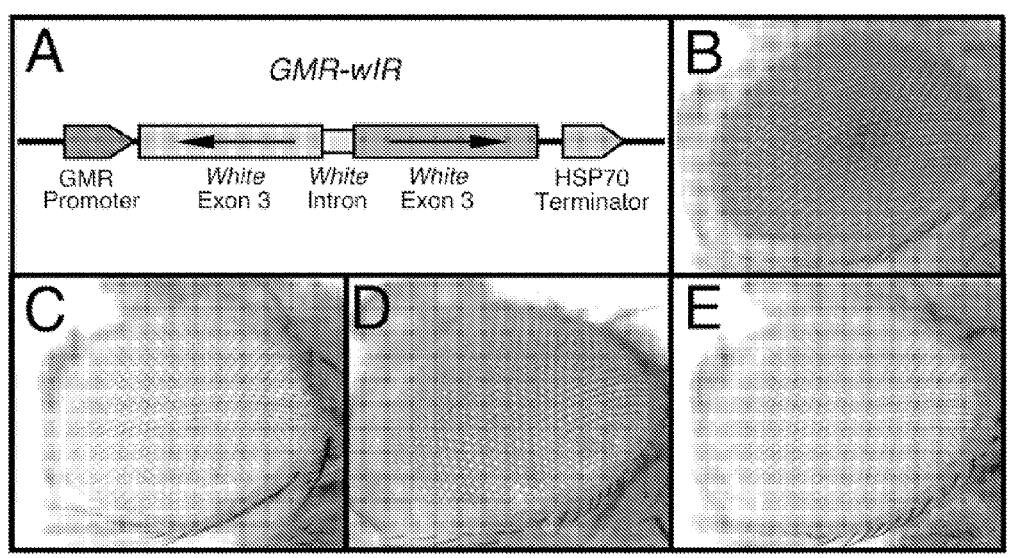
FIG. 3 shows (A) the white RNAi transgene; (B) a white+ eye; (C) a white mutant eye; (D) an eye in a white+ animal carrying one copy of the white RNAi transgene; (E) an eye in a white+ animal carrying two copies of the white RNAi transgene.

The third exon of the white gene was placed in a tail-to-tail orientation separated by the 74 nucleotide white intron (See FIG. 3). The tail-to-tail repeat was placed into the pGMR transformation vector. pGMR drives transgene expression specifically in the adult compound eye by virtue of the eye-specific GMR promoter. White$^+$ flies were then transformed with the vector and transformants that had a white loss-of-function phenotype were selected (See FIG. 3). Seven transformant lines were generated exhibiting a yellow eye color with one copy of the transgene (e.g., partial silencing). Transformants bearing two copies of the transgene were virtually indistinguishable from null white mutants (e.g., complete silencing). Importantly, all individual flies from each line exhibited a uniform eye color phenotype indicating strong expressivity and penetrance of the RNAi effect. This meant that screening for eye color variants of such flies would minimize the likelihood of picking out false-positives or missing relevant mutants.

The simplest way to screen for RNAi mutants to isolate recessive mutants that are viable and fertile, but are defective (e.g., enhanced or inhibited) for RNAi. This approach has been used for all heretofore RNAi genetic screens in various models systems.

The present invention provides a new strategy based upon the suspicion that much of the RNAi mechanism has critical links to other processes that are essential for viability or fertility. Thus, if true, many mutants that perturb RNAi would be recessive lethal or sterile and would be missed in a screen for viable mutants. This suspicion is based on the observation that mutations in genes such as Dicer and Ago1 produce lethal and/or sterile phenotypes (See, e.g., Grishok et al., (2001) cell 106, 23-24; Kataoka et al., (2001) Genes Cells 6, 313-325). Thus, a F1 genetic mosaic screen was devised that allowed the identification of recessive mutations of this class.

The F1 genetic mosaic screen is based on a strategy to create flies that are heterozygous but in which the compound eye is composed of cells homozygous mutant for one of the five major chromosomal arms. This screen can detect homozygous mutations that perturb RNAi of white in the compound eye. The screen is outlined in FIG. 4.

Figure 4A:
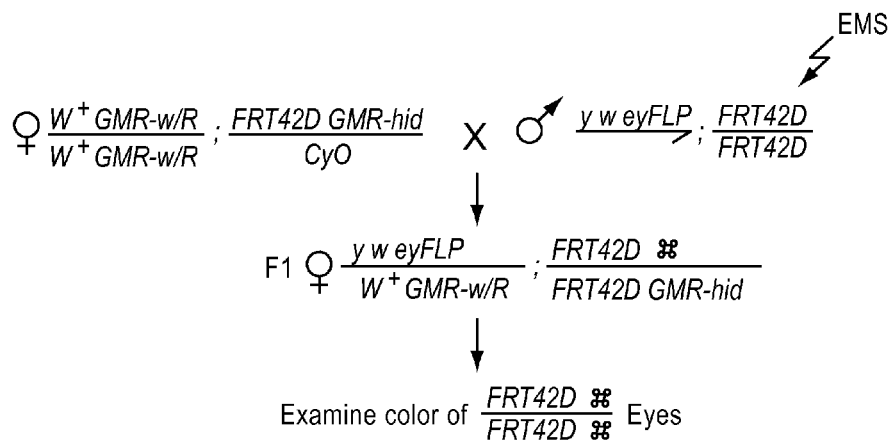
FIGS. 4A and 4B show a schematic of the F1 genetic mosaic screen.
Figure 4B:
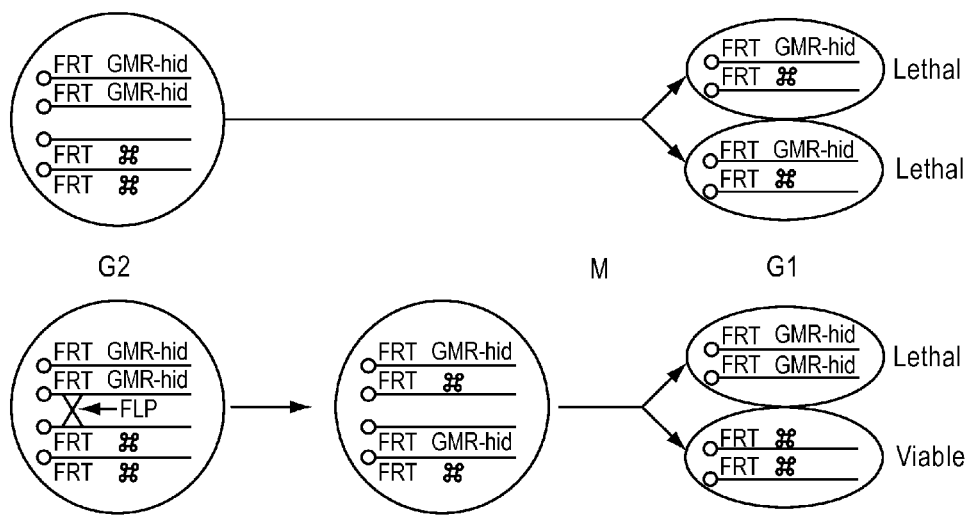
Figure 5:
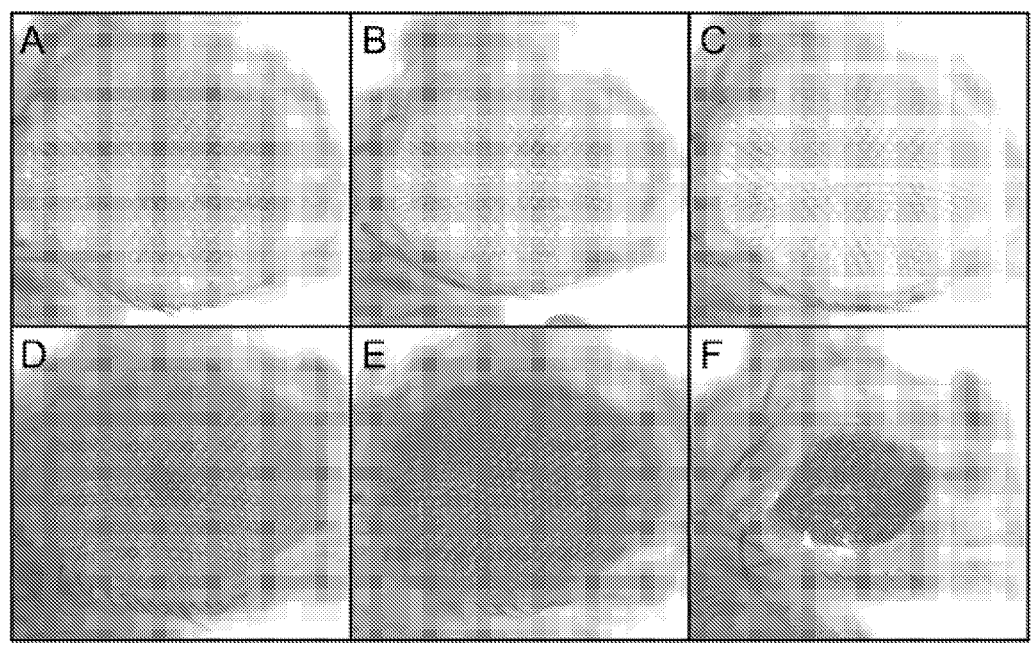
FIG. 5 shows (A) a fly with normal CG4966 gene; (B) a fly with a mutant allele of CG4966; (C) a fly with a different mutant allele of CG4966; (D) a normal eye with smooth surface; (E) a fly with a Csk RNAi transgene, showing a mildly rougher surface due to weak RNAi against Csk; (F) a fly with Csk RNAi transgene and mutant for CG4966, showing a much rougher and smaller eye.

Following ethyl-methane-sulfonate (EMS) mutagenesis, homozygous mutant clones were generated in F1 progeny using the FLP-FRT system to induce site-specific mitotic recombination. To restrict recombination to the eye, FLP recombinase was expressed under control of the eyeless promoter (eyFLP), which is exclusively active throughout the proliferative phase of eye development (See, e.g., Newsome et al., (2000) Development 127, 851-860). eyFLP—induced recombination is so efficient that virtually no heterozygous eye tissue remains by the end of the proliferative phase. The wild-type FRT chromosome was marked with the cell-death transgene GMR-hid, which kills retinal cells during metamorphosis (e.g., post-proliferative) due to the eye-specific GMR promoter driving the apoptotic hid gene (See, e.g., Stowers and Schwarz (1999) Genetics 152, 1631-1639). The fates of the three possible genotypes of retinal cells are shown in FIG. 4. Any retinal cell possessing even one copy of GMR-hid will die, leaving only retinal cells homozygous for the mutagenized chromosome. Since the remaining cells compensate in number for the missing ones by further division, the size and morphology of eyes engineered in this fashion are normal.

The F1 progeny of mutagenized flies also contained one copy of the white hairpin transgene on the X chromosome. These flies ordinarily exhibit a yellow eye color, due to partial silencing of white (See FIG. 3). Mutant flies were searched for in which the eye color was changed from yellow to white (e.g., complete silencing). Genes that normally inhibit white RNAi would be detected by such enhancer mutations that generate a white eye phenotype.

The screen was conducted on three autosomal chromosome arms representing 60 percent of the genome (See, e.g., Lee et al., (2004) Cell 117, 83-94). Hundreds of enhancer mutations were isolated that displayed white eyes. Once stocks of these mutants were established, they were retested for their ability to enhance the phenotype induced by RNAi against a totally different gene, Csk. If mutants also enhanced the Csk (RNAi) phenotype, it indicated that the mutants are general enhancers of RNAi and are not impacting unrelated phenomena such as white hairpin RNA transcription or pigment metabolism. The great majority of the original mutants identified were not RNAi enhancers based on this criteria, and these mutants were discarded. The remaining mutants were tested further (e.g., See Examples 2-5, below).

Example 2 dHPS4 is an RNAi Inhibitor

One complementation group identified on chromosome 2R contained five mutant alleles. All alleles in various trans-heterozygous combinations enhanced the RNAi phenotypes of white and Csk to comparable degrees (See FIG. 4). The mutant phenotypes were highly specific for RNAi. No other abnormalities were apparent. This indicates that the affected gene has a highly specific function in RNAi inhibition.

The chromosomal position of the mutant locus was mapped by SNP and deficiency mapping as previously described (See, e.g., Lee, et al. Cell 117, 83-94 (2004)). This narrowed the interval containing the locus to approximately 22 kb. Within the interval, a total of six annotated genes were identified from the sequenced genome. The genes from mutant and parental wild-type chromosomes were sequenced. It was determined that all five mutant alleles contained changes in the coding sequence of CG4966. Each of the changes independently generated nonsense mutations, resulting in predicted protein products that were smaller than normal. The positions of the mutations are outlined in FIG. 6. These data provide that the RNAi inhibitor gene identified from the screen corresponds to CG4966.

No motifs or functional protein domains were recognizable in the predicted protein sequence of CG4966. However, when the CG4966 (e.g., isoforms RB and RA, SEQ ID NOS. 1 (FIG. 14) and 2 (FIG. 15), respectively) sequence was compared to genes in other species, significant similarity was observed to a gene found in various insect and vertebrate genomes (See FIG. 6). Strikingly, the human ortholog of CG4966 is the Hermansky-Pudlak syndrome 4 (HPS4) gene (See, e.g., Suzuki, T. et al. Nat Genet. 30, 321-4 (2002), See FIG. 17). Hermansky-Pudlak syndrome (HPS) is a rare group of autosomal recessive diseases whose manifestations include oculocutaneous albinism, bleeding, and lysosomal ceroid storage (See, e.g., Huizing et al., Traffic 1, 823-35 (2000)). The bleeding problems of HPS result from platelet dysfunction and lead to easy bruising, nose bleeds, and extended bleeding. Its etiology has been related to defects in 7 genes: HPS1 to HPS7. The mouse HPS4 ortholog called light ear has similar complex phenotypes when it is mutated (See, e.g., Suzuki, T. et al. Nat Genet. 30, 321-4 (2002)).

Interestingly, human HPS1 and its mouse ortholog pale ear exhibit identical phenotypes to HPS4 (See, e.g., Oh, J. et al. Nat Genet. 14, 300-6 (1996); Feng et al., Hum Mol Genet. 6, 793-7 (1997)) and HPS1 protein forms a complex with HPS4 protein in the cytosol (See, e.g., Chiang, et al. J Biol Chem 278, 20332-7 (2003); Martina et al., J Biol Chem 278, 29376-84 (2003); Nazarian et al., Proc Natl Acad Sci USA 100, 8770-5 (2003)). In addition, the HPS1 protein is absent in tissues of HPS4 mutant mice (See, e.g., Suzuki, T. et al. Nat Genet. 30, 321-4 (2002)). These results indicate that the HPS4 and HPS1 proteins function in the same pathway.

Figure 7:
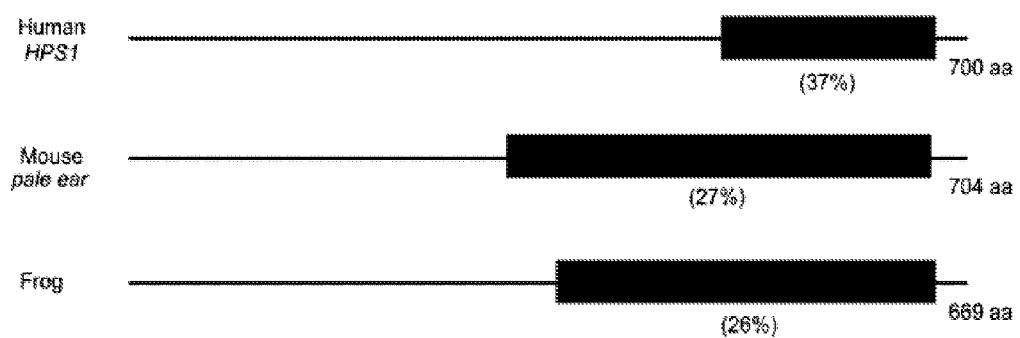
FIG. 7 shows the domain structures of vertebrate orthologs of CG12855, including HPS1 and pale ear. The percent amino acid sequence identity between each ortholog and CG12855 are shown. Lengths of vertebrate orthologs are given in amino acids (aa). CG12855 is 596 amino acids in length.

A BLAST search of the *Drosophila* genome for orthologs to human HPS1 revealed the gene CG12855 on chromosome 2R. It bears 37% identity over a 190 amino acid region encompassing the C-terminal portion of each protein (See FIG. 7). This region exhibits the strongest sequence conservation between HPS1 and various vertebrate genomes.

Figure 8:
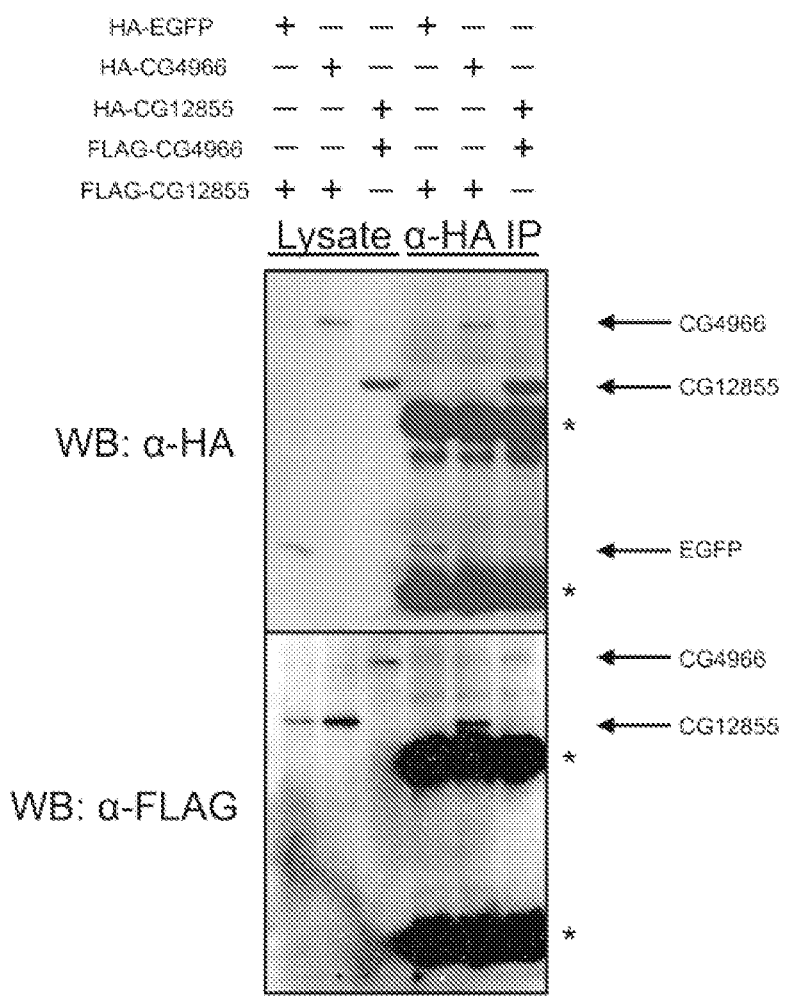
FIG. 8 shows co-immunoprecipitation of CG4966 and CG12855 proteins from *Drosophila* S2 cells.

To confirm that CG12855 (SEQ ID NO.:3 (FIG. 16)) and CG4966 (SEQ ID NOS.:1 and 2 (FIGS. 14 and 15)) correspond to the fly homologs of human HPS1 (SEQ ID NO.:4 (FIG. 17)) and human HPS4 (SEQ ID NO.:5 (FIG. 17)), respectively, epitope-tagged versions of each *Drosophila* protein was co-expressed in S2 cells. The co-expressing cells were harvested, and the potential association between the proteins was analyzed by co-immunoprecipitation (See FIG. 8). When HA-tagged CG4966 protein was immunoprecipitated and blotted for the presence of FLAG-tagged CG12855, a protein with the predicted size for CG12855 was observed. Control immunoprecipitations done in the absence of HA-CG4966 failed to co-immunoprecipitate FLAG-CG12855. Immunoprecipitation of CG12855 also resulted in the co-IP of CG4966 (See FIG. 8). Thus, the two proteins specifically associate with each other in vivo. On the basis of conserved protein structure and association, CG4966 has been named dHPS4, and CG12855 has been named dHPS1.

Example 3 dHPS4 Inhibits Assembly of Holo-RISC

Figure 9:
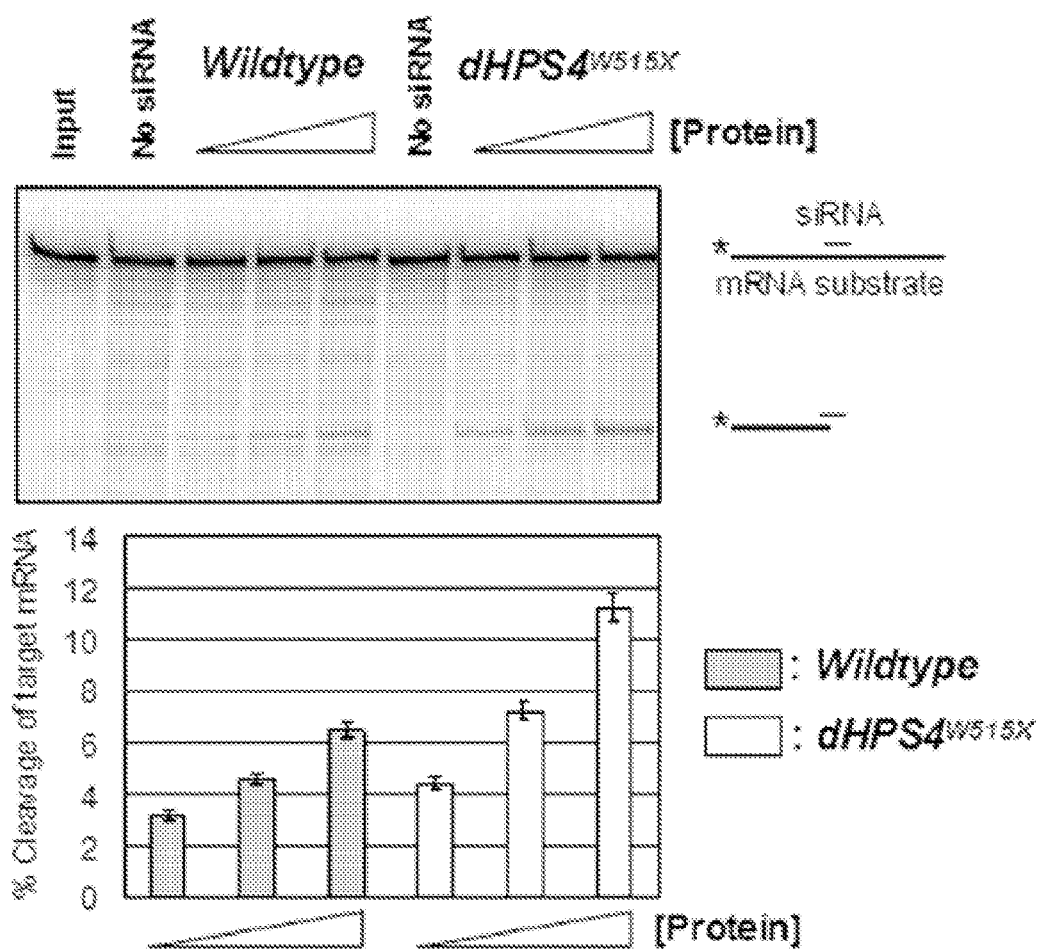
FIG. 9 shows that extracts from the dHPS4 mutant show greater siRNA-directed mRNA cleavage activity than normal. The top panel shows the products of a cleavage reaction after incubation of extract with ATP and siRNA. The lower panel shows that this effect is quantitative when measured and reproduced.
Figure 10:
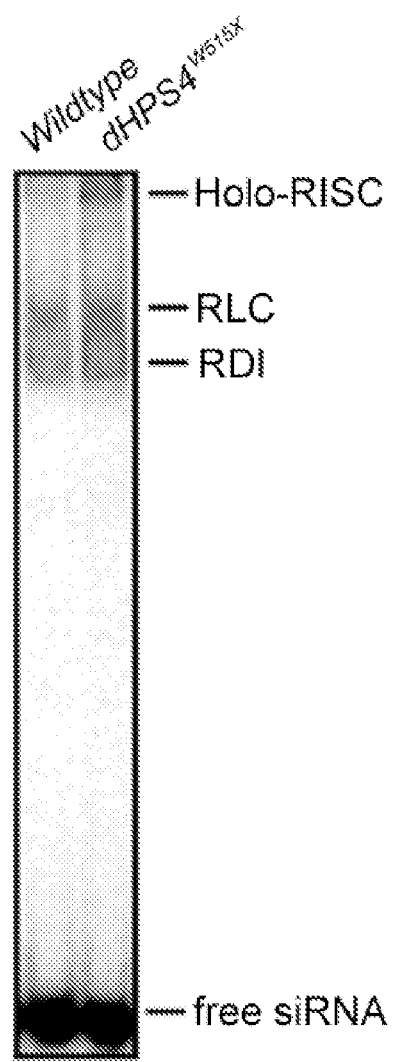
FIG. 10 shows that extract from the dHPS4 mutant shows greater accumulation of Holo-RISC.

Next, the biochemical role for dHPS4 (e.g., in inhibiting RNAi) was examined by preparing extracts from wildtype and dHPS4 mutant tissues. Extracts were tested for different steps in the RNAi pathway. Formation of siRNA from dsRNA was completely normal in mutant extracts. In contrast, cleavage of mRNA targets directed by siRNAs was significantly enhanced in mutant extracts (See FIG. 9). Thus, the present invention provides that a normal role for dHPS4 is to attenuate siRNA-guided target destruction. The affected steps were further characterized by resolving RISC and pre-RISC complexes by native gel electrophoresis (See, e.g., Pham et al., Cell 117, 83-94 (2004)). Mutant extracts had normal levels of the R2D2/Dicer-2 Initiator Complex (RDI) and RISC Loading Complex (RLC) (See FIG. 10). However, levels of holo-RISC were much higher than normal, indicating that dHPS4 specifically reduces holo-RISC abundance. It is unlikely that dHPS4 does so by modification of the siRNA since the apparent sizes of the siRNA strands are unaffected. Although an understanding of the mechanism is not necessary to practice the present invention and the present invention is not limited to any particular mechanism of action, in some embodiments, the present invention demonstrates that dHPS4 reduces holo-RISC levels by altering (e.g., inhibiting) the activity of the holo-RISC complex or one or more proteins in the reaction.

Example 4

Loss of dHPS4 Results in Three-fold Stronger RNAi Activity than Normal

Figure 11:
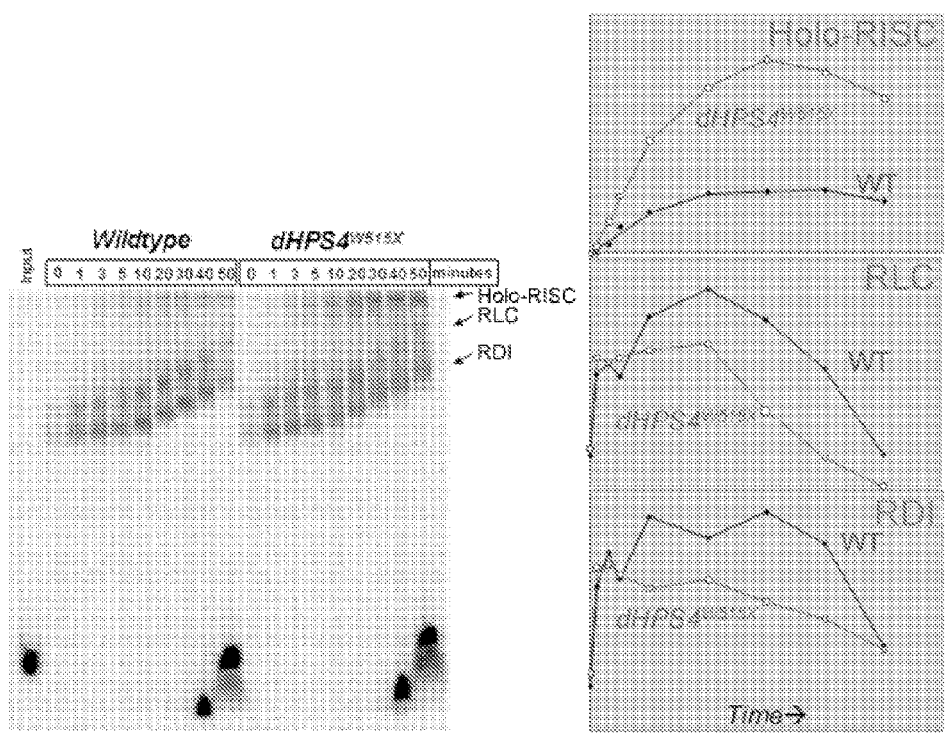
FIG. 11 shows that the step between intermediate and holo-RISC complexes is enhanced in the dHPS4 mutant. The left panel shows a time course of complex formation after labeled siRNA is added to protein extract. The right panel shows the quantitation of complex abundance over time.

To determine if dHPS4 slows down the rate of holo-RISC formation or if it accelerates the rate of holo-RISC turnover, a kinetic analysis of RISC assembly was performed. Mutant extracts displayed a three-fold increase in the rate of holo-RISC formation from the RLC, which is comparable to the overall enhanced rate of holo-RISC activity at steady state (See FIG. 11). Thus, the present invention provides that dHPS4 attenuates the rate of holo-RISC formation.

Figure 12:
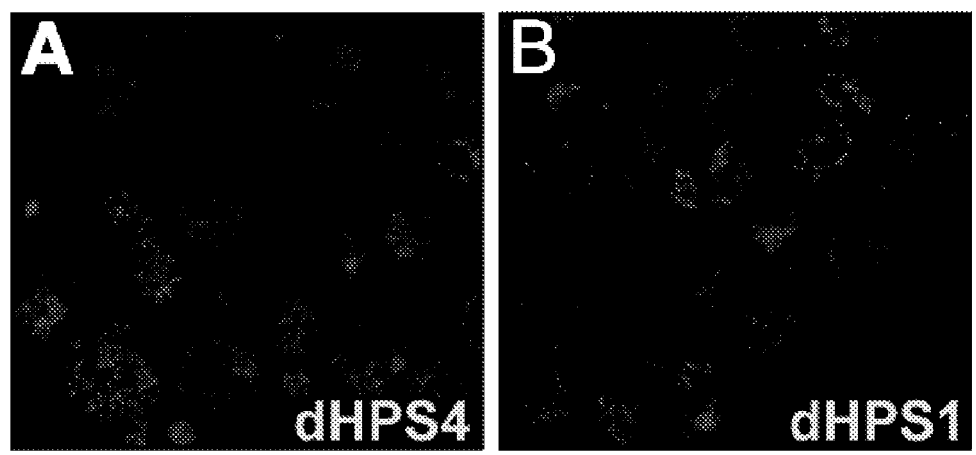
FIG. 12 shows that dHPS1 and dHPS4 proteins co-localize in the cytosol of *Drosophila* S2 cells. Epitope-tagged expression vectors were transfected into S2 cells, and HA-tagged proteins were visualized by immunofluorescence after 24 hours expression. Cells were counterstained for DNA. Cells expressed dHPS4 (A) or dHPS1 (B)

Both dHPS1 and dHPS4 are co-localized to the cytoplasm of S2 cells (See FIG. 12), as are their human counterparts in human cell culture (See, e.g., Nazarian et al., Proc Natl Acad Sci USA 100, 8770-5 (2003)). Interestingly, a two-hybrid analysis revealed association between dHPS4 and two *Drosophila* translation factors: rpS3 and Waclaw, a GTP-binding translation elongation factor (See, e.g., Giot, et al. Science 302, 1727-36 (2003)). Although an understanding of the mechanism is not necessary to practice the present invention and the present invention is not limited to any particular mechanism of action, in some embodiments, since holo-RISC appears to be associated with 80S ribosomes (See, e.g., Pham et al., Cell 117, 83-94 (2004)), the present invention provides that dHPS4 may interact with RISC through the ribosome.

Example 5

Altering dHPS4 Expression and/or Activity Enhances RNAi

The present invention provides methods of enhancing RNAi by altering (e.g., disabling or repressing the synthesis of) HPS4 and/or HPS1. For example, the present invention provides that dHPS4 physically associates with dHPS1 protein, and that mutation of the HPS1 gene results in the identical phenotype to a HPS4 mutant. Thus, the present invention contemplates a method of enhancing RNAi potency via inhibiting the interaction between HPS4 and HPS1 (e.g., using a small molecule or antibody to inhibit HPS4 and/or HPS1 activity of function, or, inhibiting expression of HPS4 or HPS1 (e.g., using RNAi)).

Example 6

Biochemistry of Human RNAi

Figure 13:
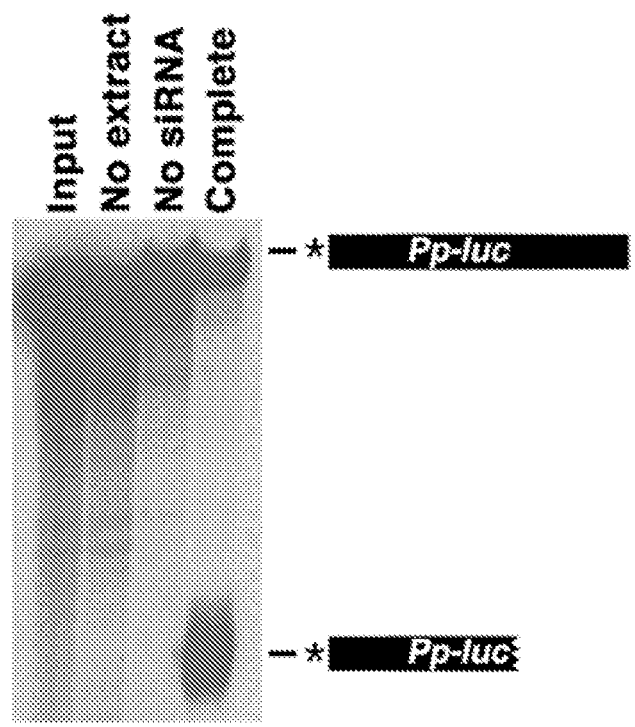
FIG. 13 shows mRNA cleavage reaction with human HeLa extract with the 5' cleavage product of RNAi reaction indicated as the smaller labeled species.

As described above, many of the studies on HPS4 have been done in the *Drosophila* model system. However, the ability to study the biochemistry of RNAi in humans has also been established. Extracts from HeLa cells are competent for RNAi in vitro (See FIG. 13), and these extracts have been used to identify complexes that interact with siRNAs and that may play a role in RISC assembly (See, e.g., Pellino, et al., 11: 1719-1724 (2005)).

Example 7

Subcellular Localization of dHPS1 and dHPS4

Figure 18:
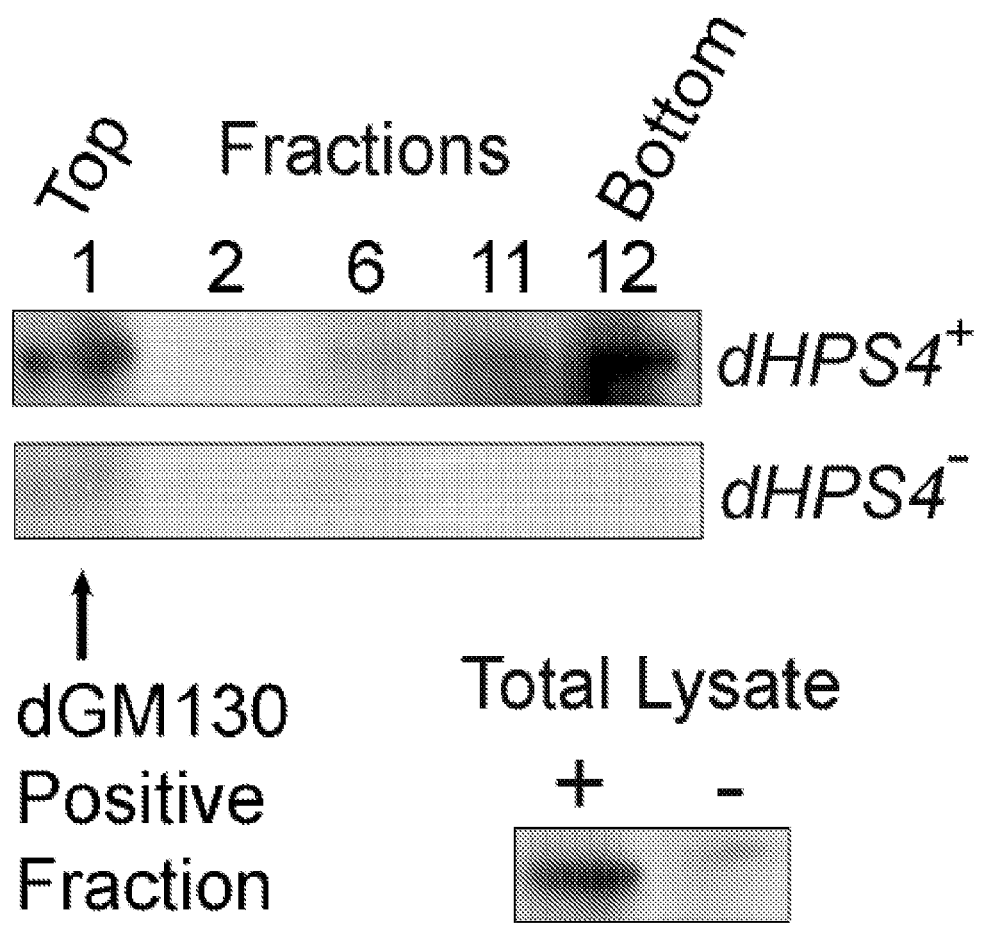
FIG. 18 shows OPTIPREP gradient centrifugation of head extract from wildtype or HPS4 mutant adults. Membranes and associated molecules float to the top of the gradient, as evident by the specific localization of the Golgi protein GM130 to the top fraction as determined by Western blot. Bottom fractions contain high molecular weight membrane-free molecules. Aliquots of each fraction were probed with anti-HPS4 antibody. Antibody specificity for HPS4 protein is seen by Western blot of a parallel gradient from a HPS4 mutant.

Epitope-tagged dHPS1 and dHPS4 were found in the cytoplasm of S2 cells, particularly in punctate structures. These structures are not P-bodies since they do not label with Decapping Protein. Rather, they appear to be trafficking vesicles since human HPS4 and HPS1 localize to the Golgi and recycling endosomes. Two-hybrid analysis revealed association between dHPS4 and the vesicle trafficking protein Syntaxin16. Although an understanding of the mechanism is not necessary to practice the present invention and the present invention is not limited to any particular mechanism of action, in some embodiments, dHPS4 alters the RISC assembly mechanism by recruiting RISC factors to vesicle compartments that are recalcitrant to RISC assembly. Supporting evidence for such a model comes from the observation that human Ago2 and Dicer are frequently localized to Golgi and endosomes of secretory cells such as neurons and pancreatic cells. Thus, in some embodiments, HPS4 promotes Ago2 localization, providing less Ago2 protein for RISC assembly. OPTIPREP gradient ultracentrifugation was used to separate *Drosophila* extract into membrane-associated and free fractions. By Western blot, about half of the *Drosophila* HPS4 protein co-sediments with membranes to the top of the gradient along with the Golgi marker protein GM130 (See FIG. 18). The majority of Ago2 protein also co-sediments with membranes from *Drosophila* extract.

Example 8

Characterization of dHPS4 Activity in the miRNA Pathway In Vivo

It has been shown that dHPS4 represses the siRNA pathway, which is important for a multitude of RNAi applications in research, agriculture, and medical therapeutics. However, the present invention is not limited to the siRNA pathway. Indeed, as described below, the present invention also provides compositions and methods for the manipulation of the miRNA pathway (e.g., for use in commercial applications (e.g., medical (e.g., therapeutic), agriculture, and research applications (e.g., miRNA therapeutics under development to treat cancer and hypercholesterolemia)).

In order to determine whether one or more of the repressors HPS4 and HPS1 play a role in the miRNA pathway, dHPS4 mutants were tested for their effect on miRNA pathway activity. Experiments conducted during the development of the present invention demonstrated that dHPS4 inhibits miRISC activity.

In order to assay miRNA pathway activity in vivo, a transgene indicator was created. GFP was expressed under an eye-specific promoter and linked to the 3'UTR of the Bearded gene (See FIG. 19A). The indicator relies on the fact that if miRNAs interact with the 3'UTR, this will be "indicated" by reduced GFP fluorescence. The UTR contains natural miRNA-binding sites for miR-2, -4, -7, -11, and -79, and it is naturally regulated by these miRNAs in the fly. This UTR was chosen rather than one with artificial miRNA sites for several reasons. First, its broad spectrum generally ensures a greater likelihood of detection of mutants affecting miRNAs. Second, the 3'UTR confers strong responsiveness to Dcr-1 in the developing eye.

Figure 19:
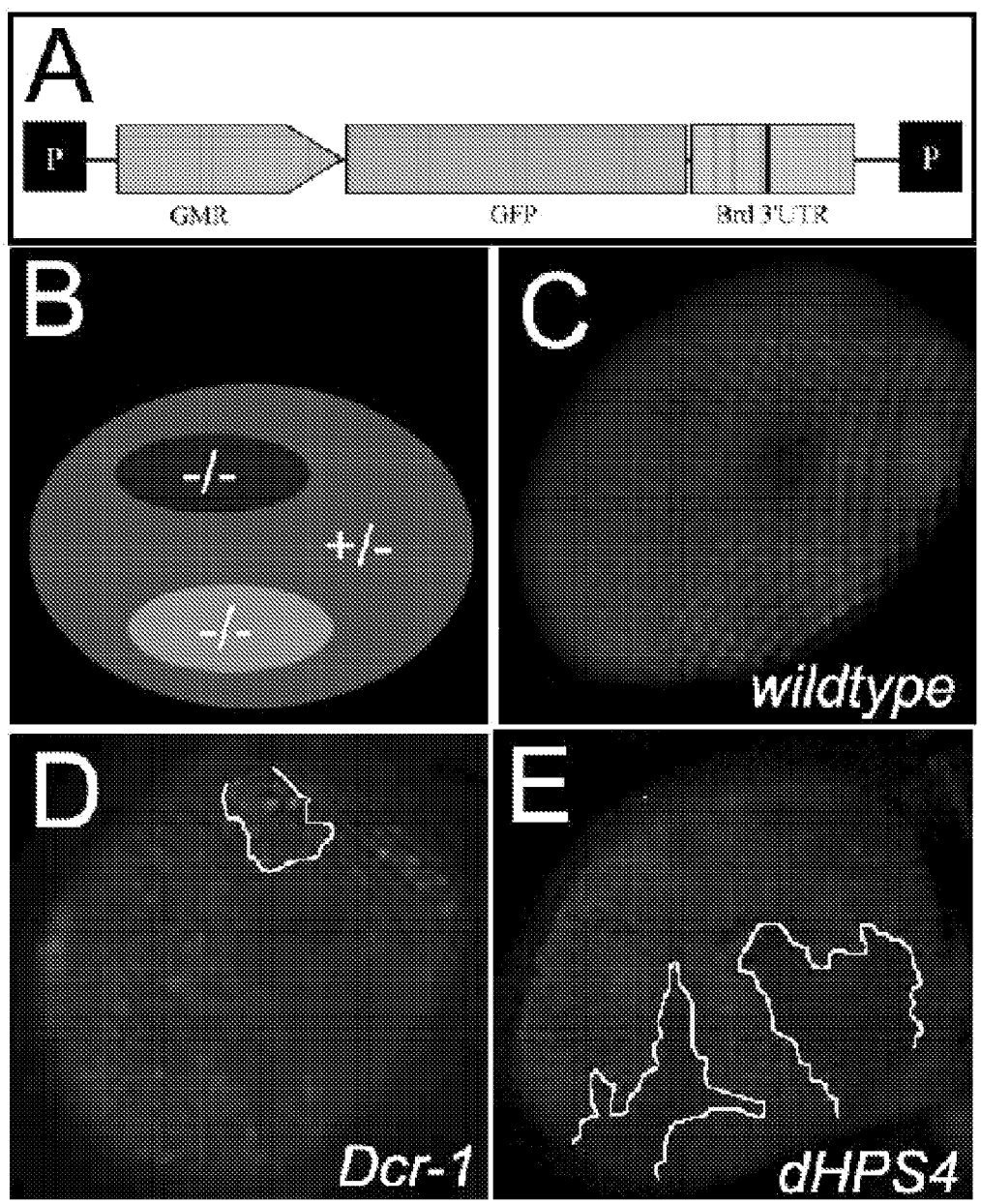
FIG. 19 shows HPS4 mutants exhibit enhanced miRNA pathway activity in vivo. (A) Structure of the construct GMR-GFP-BRD used to express GFP in adult eyes. GFP expression is driven in the eye by the GMR promoter and is controlled by the 3' UTR from the Brd gene, which harbors four miRNA binding sites. Three sites (light bars) share a common seed sequence, distinct from the fourth site (dark bar). (B) Schematic drawing of an eye from a GMR-GFP-BRD adult that is genetically mosaic due to FLP/FRT recombination. Clones that are homozygous for a mutation in a miRNA pathway gene (−/−) could express higher or lower levels of GFP compared to the surrounding wild type tissue (+/+), resulting in mosaic fluorescence. (C-E) Eyes of a adults expressing GMR-GFP-BRD. Clones are highlighted with their boundaries marked with yellow lines. (C) An eye with no clones. (D) An eye with Dcr-1 mutant clones (circled). (E) An eye with two HPS4 mutant clones.
Figure 20:
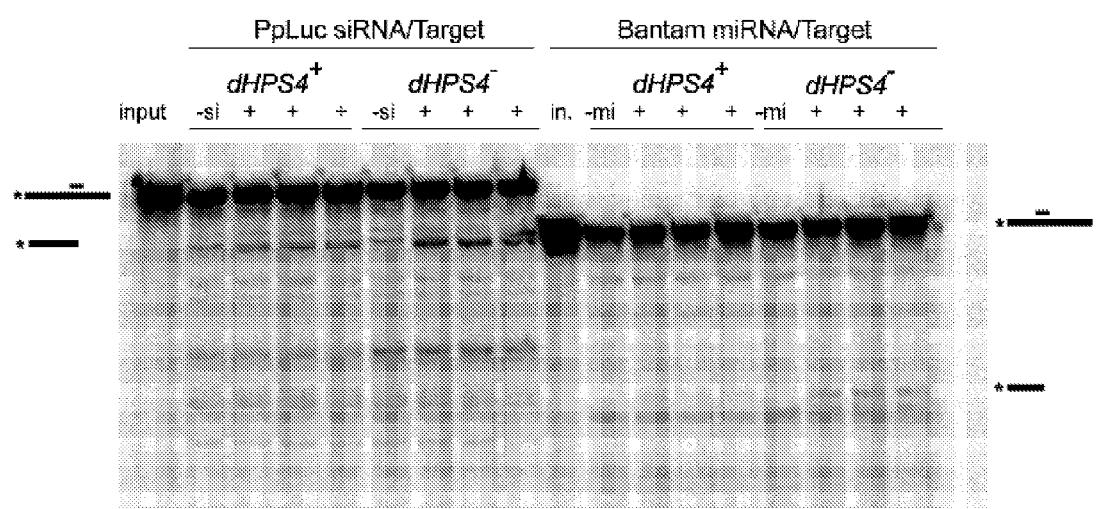
FIG. 20 shows HPS4 mutants exhibit enhanced miRNA silencing in vitro. 5'-labeled mRNA was incubated with wildtype or HPS4 mutant head extract. Reactions were supplemented with either a Pp-luciferase siRNA (+si) or a bantam miRNA (+mi). Reactions as indicated contained no siRNA or miRNA. Target mRNAs contained perfectly complementary sequence to their cognate siRNA or miRNA at the indicated positions. When a miRNA can bind with perfect complementarity to its target, cleavage of the target ensues. This is detected by the presence of the 5'-labeled cleavage product as indicated.

GFP expression is easily scored in unpigmented adult eyes, affording easy and rapid phenotype testing (See FIG. 19B). Clones of eye cells that are homozygous mutant for a particular gene of interest were generated using the eyFLP/FRT system to induce site-specific mitotic recombination. The mosaic flies also contain one copy of the GFP indicator transgene. Clones within eyes that were more or less fluorescent than normal were examined. Genes that activate the miRNA pathway can be detected by mutations that generate brighter fluorescence, while repressor genes are detected by mutations that generate less fluorescence. Dcr-1 mutants were used to demonstrate a functioning system. Indeed, Dcr-1 mutant eye clones were readily detected with brighter fluorescence—the small clone size reflected a growth defect of the mutant. (See FIG. 19C). HPS4 mutant clones showed weaker fluorescence than normal, indicating that HPS4 is also a miRNA pathway repressor (See FIG. 19D).

The ability of HPS4 to represses the miRNA pathway was further evaluated by testing its activity in vitro. Pre-diced duplex miRNA or pre-miRNA was added to dHPS4 mutant or wildtype extract, and miRISC activity was detected by cleavage of a complementary substrate mRNA. Unlike the case with siRNAs, assembly of such miRNA duplexes into miRISC is Dicer2-independent. Comparison of miRISC activity from normal and dHPS4 mutant extracts indicate that the presence of dHPS4 inhibits miRISC activity in vitro (FIG. D3). Thus, in some embodiments, the present invention provides that inhibition of repressors of RNAi (e.g., HPS4 and/or HPS1) can be used to enhance the performance of the miRNA pathway.

Example 9

Identification and Characterization of the RNAi Repressor CG6969

Figure 21:
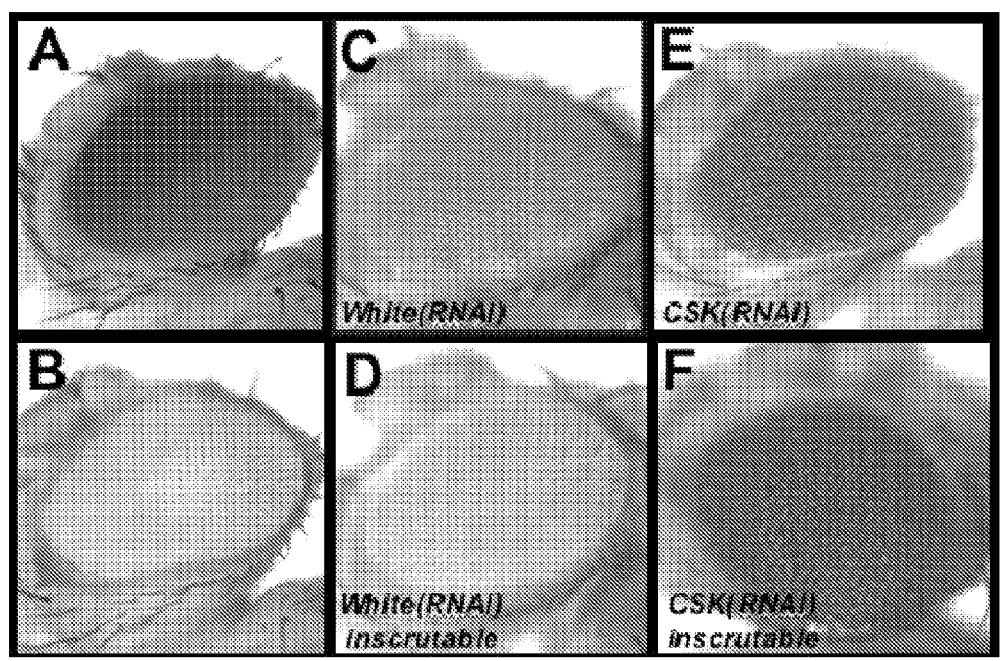
FIG. 21 shows CG6969 mutants exhibit stronger RNAi in vivo. (A) The bright red eye of a normal adult *Drosophila*. (B) The white eye of a fly missing its white gene. (C) The pale orange eye due to partial silencing of the white gene by transgenic RNAi. (D) The complete silencing (white eye) of the white gene by transgenic RNAi in an CG6969 mutant fly. (E) The weakly disordered patterning of facet lenses in a fly that has partial RNAi silencing of the CSK kinase gene. (F) Patterning of facet lenses is more disordered due to stronger RNAi silencing of CSK in a CG6969 mutant fly.

The screen of the *Drosophila* chromosome 3R led to the isolation of two mutations that failed to complement each other. The mutations generated stronger RNAi activity as measured by white (RNAi) when homozygous mutant and when in trans-heterozygous combination (See FIG. 21). The two mutations map to the same chromosomal locus, and thus are alleles of the same gene. To verify that the mutations affected the siRNA pathway, the mutants' effects on RNAi against the Csk gene were characterized. Indeed, both mutations enhanced the rough-eye phenotype of Csk(RNAi) (See FIG. 21). The mutant flies were viable and fertile. The only detectable phenotype that they exhibit is enhanced RNAi.

The gene's location was mapped by SNP analysis to an interval from 94B1 to 94C3. The location was further narrowed to a smaller interval. This was done by more extensive SNP analysis. 200 or more recombinant lines with third chromosomes were collected that are composite of the mutant FRT chromosome and a wild-type polymorphic chromosome. These were genotyped for known SNPs in the relevant interval. The mutants were then crossed with 17 DrosDel deletions that are present in the interval to narrow the mutation further. Phenotyping was done by assaying white(RNAi). Using these methods, the interval was narrowed to 27 kb, from 18499K to 18526K. This interval includes seven annotated genes. The genes were sequenced from the non-mutagenized parental animal and the two different mutant animals. Sequence polymorphisms were searched for in coding regions of the genes. One gene, CG6969, contained single nucleotide polymorphisms in the mutant animals when compared to wildtype. The sequence change in one mutant generates a premature stop codon in the CG6969 open reading frame at position 524. The sequence change in the other mutant generates a glycine to threonine codon change at position 686 in the open reading frame. This glycine residue is invariant in paralogous and orthologous proteins related to CG6969, indicating that it is functionally important for the protein's function (See FIG. 22). Thus, based on these criteria, CG6969 was identified as an RNAi repressor.

Figure 23:
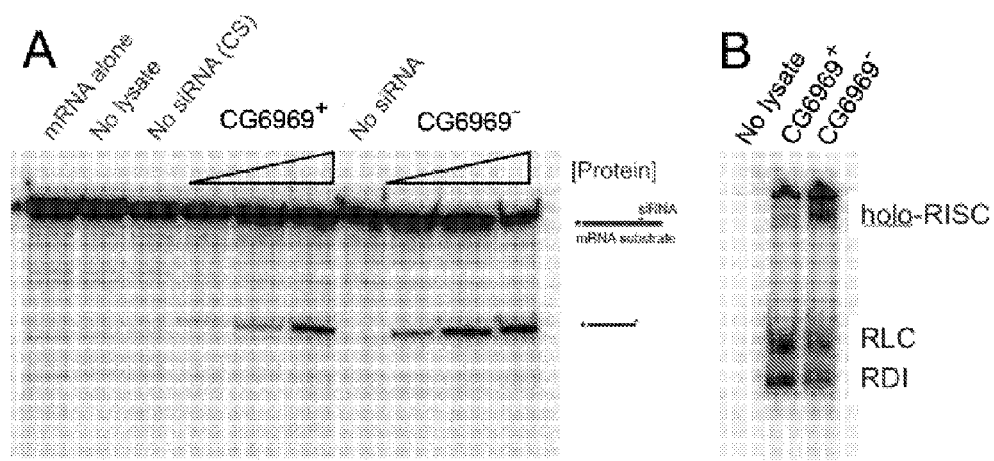
FIG. 23 shows CG6969 mutants exhibit stronger RNAi in vitro. (A) Target mRNA cleavage programmed by siRNA is stronger in embryo extract from a CG6969 trans-heterozygous mutant compared to wildtype control. Shown is a titration of extract protein. (B) Native gel electrophoresis of labeled siRNA complexes formed with embryo extracts from CG6969 wildtype or mutant animals. Level of holo-RISC complex is higher in the mutant extract when compared to levels of other complexes such as RDI and RLC.
Figure 24:
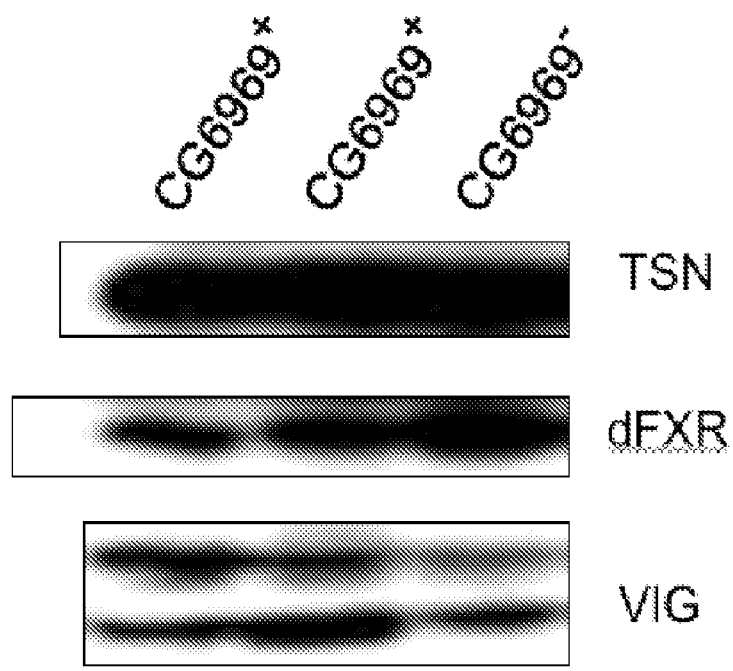
FIG. 24 shows Western blot analysis of RISC subunit abundance from extract derived from two different wildtype (CG6969+) sources of embryos and from extract derived from CG6969 trans-heterozygous mutant embryos. Probed were antibodies against VIG, dFXR, and TSN proteins.

Biochemical analysis was performed on the CG6969 mutants to determine which step in the siRNA pathway depended upon the gene product. From this analysis, it appeared that holo-RISC activity is repressed by CG6969 (See FIG. 23). Moreover, the inhibition of holo-RISC activity correlated with a reduction in holo-RISC abundance when holo-RISC was assembled in vitro. In contrast, the abundance of RISC assembly intermediate complexes RDI and RLC were not reduced by CG6969. To determine if CG6969 reduced holo-RISC by down-regulating abundance of RISC subunits, their abundance was examined by Western blot. CG6969 did not affect the levels of known holo-RISC subunits such as Ago2, TSN, VIG, and dFXR (See FIG. 24). Thus, although an understanding of the mechanism is not necessary to practice the present invention and the present invention is not limited to any particular mechanism of action, in some embodiments, CG6969 represses the siRNA pathway at the same step as HPS4. Thus, the present invention provides a peroxidase that acts as an inhibitor of the siRNA pathway. Given the virtually complete conservation of RNAi mechanisms between insect and human, it is contemplated that peroxidase participation in RNAi will be regulated similarly in both species.

CG6969 protein structure was characterized. Using the software PROSITE and PFAM, it was determined that CG6969 contained a transmembrane domain at its amino-terminus and a peroxidase domain at its carboxy-terminus (See FIG. 25). Animal peroxidases reduce hydrogen peroxide and donate free oxygen to small-molecule acceptors such as glutathione, alcohol, or chloride. Besides being important regulators of redox potential, peroxidases also play important roles in innate immune defense. The defense strategies that animal hosts use to combat infection include pathogen recognition, phagocytosis, cytoskeleton remodeling, coagulation, melanization, and generation of reactive oxygen species (ROS). In mammals, one of the earliest innate immune responses involves the generation of sufficient amounts of ROS to combat the pathogen, as well as concurrent elimination of residual ROS in order to protect the host. Failure to balance synthesis and elimination of ROS can lead to many chronic epithelial inflammatory diseases in humans. Peroxidases fulfill an antioxidant function in general by reducing ROS. However, in granulocytic immune cells such as eosinophils, peroxidases help generate highly reactive species such as HOBr that carry out widespread chemical oxidation of pathogens. Alignment of CG6969 with related peroxidases from other species did not reveal an unambiguous homolog. Rather, CG6969 is most highly related to a few human peroxidases in the immune system that include MPO, LPO, and EPX (See FIG. 28). These peroxidases also contain an amino-terminal transmembrane domain. Thus, in some embodiments, CG6969 plays an active role in immune defense mechanisms.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of enhancing the potency of RNAi silencing of an aberrantly expressed gene in a cell comprising co-administering to the cell an siRNA specific for HPS1 or CG6969 with a siRNA and/or miRNA specific for the aberrantly expressed gene such that said aberrantly expressed gene is silenced by said siRNA and/or miRNA specific for said aberrantly expressed gene to a greater extent than when said siRNA specific for HPS1 or CG6969 is absent.

2. The method of claim 1, wherein said siRNA specific for HPS1 or CG6969 is specific for HPS1.

3. The method of claim 1, wherein said siRNA specific for HPS1 or CG6969 is specific for CG6969.

4. The method of claim 1, wherein said aberrantly expressed gene is an oncogene.

5. The method of claim 1, wherein said aberrantly expressed gene is a gene expressed by a pathogenic organism.

6. The method of claim 1, wherein said cell is in vitro.

7. The method of claim 1, wherein said cell is in vivo.

* * * * *